(12) United States Patent
Krumm et al.

(10) Patent No.: US 11,236,057 B2
(45) Date of Patent: Feb. 1, 2022

(54) AROMATIC SURFACTANTS

(71) Applicant: REGENTS OF THE UNIVERSITY OF MINNESOTA, Minneapolis, MN (US)

(72) Inventors: Christoph Krumm, Saint Paul, MN (US); Kristeen Joseph, Minneapolis, MN (US); Dae Sung Park, Minneapolis, MN (US); Mahesh Mahanthappa, Minneapolis, MN (US); Paul J. Dauenhauer, Sunderland, MA (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

(21) Appl. No.: 15/773,991

(22) PCT Filed: Nov. 7, 2016

(86) PCT No.: PCT/US2016/060775
§ 371 (c)(1),
(2) Date: May 4, 2018

(87) PCT Pub. No.: WO2017/079719
PCT Pub. Date: May 11, 2017

(65) Prior Publication Data
US 2018/0327375 A1 Nov. 15, 2018

Related U.S. Application Data

(60) Provisional application No. 62/403,305, filed on Oct. 3, 2016, provisional application No. 62/252,200, filed on Nov. 6, 2015.

(51) Int. Cl.
| | | |
|---|---|---|
| *C07D 307/46* | (2006.01) |
| *C07D 307/64* | (2006.01) |
| *C07D 307/36* | (2006.01) |
| *C07D 307/40* | (2006.01) |
| *C07D 207/333* | (2006.01) |
| *C07D 207/337* | (2006.01) |
| *C07D 213/30* | (2006.01) |
| *C07D 213/50* | (2006.01) |
| *C07D 307/20* | (2006.01) |
| *C07D 307/42* | (2006.01) |
| *C07D 333/16* | (2006.01) |
| *C07D 333/32* | (2006.01) |

(52) U.S. Cl.
CPC ....... *C07D 307/46* (2013.01); *C07D 207/333* (2013.01); *C07D 207/337* (2013.01); *C07D 213/30* (2013.01); *C07D 213/50* (2013.01); *C07D 307/20* (2013.01); *C07D 307/36* (2013.01); *C07D 307/40* (2013.01); *C07D 307/42* (2013.01); *C07D 307/64* (2013.01); *C07D 333/16* (2013.01); *C07D 333/32* (2013.01)

(58) Field of Classification Search
None
See application file for complete search history.

(56) References Cited

U.S. PATENT DOCUMENTS

| | | | |
|---|---|---|---|
| 2,411,567 A | 11/1946 | Fisher | |
| 4,233,333 A * | 11/1980 | Trummlitz | C07D 307/64 426/548 |
| 4,284,614 A * | 8/1981 | Ore | C01B 25/225 423/10 |
| 4,308,215 A | 12/1981 | Vaughan | |
| 4,477,382 A | 10/1984 | Goel | |
| 4,845,240 A * | 7/1989 | Hibino | C07D 493/04 549/252 |
| 6,187,981 B1 | 2/2001 | Marinangeli | |
| 2011/0071056 A1 | 3/2011 | Saini | |
| 2015/0150768 A1 * | 6/2015 | West | A61K 8/4973 424/65 |
| 2018/0327375 A1 | 11/2018 | Krumm | |
| 2018/0327376 A1 | 11/2018 | Park | |

FOREIGN PATENT DOCUMENTS

| | | | |
|---|---|---|---|
| EP | 245835 | * | 11/1987 |
| EP | 0268820 A2 | | 6/1988 |
| WO | WO 2005051936 A1 | | 6/2005 |
| WO | WO 2009140309 | * | 11/2009 |
| WO | WO 2015084813 A1 | | 6/2015 |
| WO | WO 2016028845 A1 | | 2/2016 |
| WO | WO 2017079718 A1 | | 5/2017 |
| WO | WO 2017079719 A1 | | 5/2017 |

OTHER PUBLICATIONS

Epstein. Analytical Biochemistry, 1982, 1991(2), 304-312 (Year: 1982).*
Czerniawski. Polish Journal of Chemistry, 1993, 67(9), 1687-93, stn record thereof, entered STN Feb. 27, 1995 (Year: 1995).*
International Patent Application No. PCT/US16/60774, filed Nov. 7, 2016; International Search Report / Written Opinion dated Apr. 6, 2017; 21 pages.
International Patent Application No. PCT/US16/60774, filed Nov. 7, 2016; International Preliminary Report on Patentability dated May 17, 2018; 12 pages.

(Continued)

*Primary Examiner* — Noble E Jarrell
(74) *Attorney, Agent, or Firm* — Mueting Raasch Group

(57) ABSTRACT

Disclosed are compounds of the Formula 1 wherein A is an aromatic moiety; H is a hydrophobic group comprising a main alkyl chain having from about 3 to about 26 carbon atoms and comprising a $C_2$ or greater alkyl chain branched from the main alkyl chain; and K is a hydrophilic group.

(I)

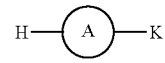

7 Claims, 44 Drawing Sheets

(56) References Cited

OTHER PUBLICATIONS

International Patent Application No. PCT/US16/60775, filed Nov. 7, 2016; International Search Report / Written Opinion dated Apr. 25, 2017; 32 pages.
International Patent Application No. PCT/US16/60775, filed Nov. 7, 2016; International Preliminary Report on Patentability dated May 17, 2018; 17 pages.
Abid, "Application of the Phase Transfer Catalysis to the Synthesis of New Furanic Polyesters" Jan. 2005 *Journal de la Societe Chimique de tunisie*: 1-9.
Adamkeiwicz, "α-Regioselective Aqueous Mukaiyama Aldol Reaction of 2-(Trimethylsilyloxy)furan with Pyruvates: α-Regioselective Aqueous Mukaiyama Aldol Reaction of 2-(Trimethylsilyloxy)furan with Pyruvates" Oct. 2016 *European Journal of Organic Chemistry*, 5 pages.
ASTM D2281-10. Standard test method for evaluation of wetting agents by the skein test; ASTM International, West Conshohocken, PA, 2010. Online: https://www.astm.org/Standards/D2281.htm (Accessed Oct. 9, 2018). DOI: 10.1520/D2281-10, www.astm.org.
Augustin, "Nano- and micro-structured assemblies for encapsulation of food ingredients" Apr. 2009 *Chem. Soc. Rev.*, 38(4):902-912.
Bajpai, "Laundry Detergents: An Overview" 2007 *J. Oleo Sci*, 56:327-340.
Bardach, "Detergents: Effects on the chemical senses of the fish *Ictalurus natalis* (le Sueur)" Jun. 1965 *Science*, 148:1605-1607.
Biermann, "Oils and Fats as Renewable Raw Materials in Chemistry" Apr. 2011 *Angew. Chem., Int. Ed.*, 50:3854-3871.
Boethling, "Designing small molecules for biodegradability" Jun. 2007 *Chem. Rev.*, 107:2207-2227.
Briggs, "Quality of rivers of the United States, 1975 water year; based on the National Stream Quality Accounting Network (NASQAN); US Geological Survey," 1977. (pdf in two parts).
Cao, "Alkylation of benzene with dodecene. The activity and selectivity of zeolite type catalysts as a function of the porous structure" Aug. 1999 *Appl. Catal. A*, 184:231-238.
Ceresana (Market Intelligence. Consulting.) Online: http://www.ceresana.com/en/market-studies/chemicals/surfactants/ceresana-market-study-surfactants.html. Accessed Oct. 9, 2018. 3 pages.
Chang, "Ultra-selective cycloaddition of dimethylfuran for renewable p-xylene with H-BEA " 2014 *Green Chem.*, 16:585-588.
Chao, "HC(4)-alkyl substituted furanyl cyclobutenediones as potent, orally bioavailable CXCR2 and CXCR1 receptor antagonists 11" Jul. 2007 Bioorganic & Medicinal Chemistry Letters, Pergamon, Amsterdam, NL, 17(13):3778-3783.
Clayden, Organic Chemistry $2^{nd}$ Ed., *Electrophilic aromatic substitution*, Oxford, New York, 2012, pp. 493-494, cover page, title page and table of contents.
Corma, "Delaminated zeolites: Combining the benefits of zeolites and mesoporous materials for catalytic uses" 1999 *J. Catal.*, 186:57-63.
Corma, Chemical routes for the transformation of biomass into chemicals Jun. 2007 *Chem. Rev.*, 107:2411-2502.
Faba, "Aqueous-phase furfural-acetone aldol condensation over basic mixed oxides" 2012 *Appl. Catal. B*, 113-114:201-211.
Faba, "Performance of bifunctional Pd/MxNyO (M= Mg, Ca; N= Zr, Al) catalysts for aldolization-hydrogenation of furfural-acetone mixtures" 2011 *Catal. Today*, 164(1):451-456.
Falbe, *Surfactants in Consumer Products*; Springer-Verlag: Heidelberg Germany, 1987. Cover page, title page and table of contents.
Fendler, "Polymerized surfactant vesicles: Novel membrane mimetic systems" Mar. 1984 *Science*, 223:888-894.
Gassama, "Sulfonated surfactants obtained from furfural" 2013 *Green Chem.*, 15:1558-1566.
Green, "Diels-Alder cycloaddition of 2-methylfuran and ethylene for renewable toluene" 2015 *Appl. Catal. B*, 180:487-496.
Guo, "Highly active and recyclable Sn-MWW zeolite catalyst for sugar conversion to methyl lactate and lactic acid" 2013 *ChemSusChem.*, 6:1352-1356.
Jordan, "Biodegradation of ionic liquids: a critical review" 2015 *Chem. Soc. Rev.*, 44:8200-8237.
Kocal, "Production of linear alkylbenzenes" Nov. 2001 *Appl. Catal. A*, 221:295-301.
Kore, "Synthesis of industrially important aromatic and heterocyclic ketones using hierarchical ZSM-5 and Beta zeolites" Mar. 2015 *Applied Catalysis A: General*, 493:129-141.
Kraus, "A direct synthesis of renewable sulfonate-based surfactants" 2013 *Surfact. Deterg.*, 16:317-320.
Ma, "Positional isomers of linear sodium dodecyl benzene sulfonate: Solubility, self-assembly, and air/water interfacial activity" Oct. 2006 *Langmuir*, 22:8646-8654.
Maduskar, "Quantitative carbon detector (QCD) for calibration-free, high-resolution characterization of complex mixtures" 2015 *Lab Chip*, 15(2):440-447.
Maneedaeng, "Modeling of precipitation phase boundaries in mixed surfactant systems using an improved counterion binding model" 2012 *J. Surfactants Deterg.*, 15:523-531.
Manojlović, "The Krafft Temperature of Surfactant Solutions" 2012 *Thermal Science*, 16:S631-S640.
Marshall, "Total Synthesis of the Pseudopterane(±)-Kallolide B" 1995 *J Org Chem.*, 60:796-797.
Marshall, "Total Synthesis of the Pseudopterane (-)-Kallolide B, the Enantiomer of Natural ( + )-Kallolide B" 1996 *J Org Chem.*, 61:5729-5735.
Mestres, "A green look at the aldol reaction" 2004 *Green Chem.*, 6:583-603.
Mihelj, "Temperature-dependent IR spectroscopic and structural study of 18 crown-6 chelating ligand in the complexation with sodium surfactant salts and potassium picrate" 2014 *Spectrochim Acta A Mol Biomol Spectrosc.*, 24(124):12-20.
Modler, "Linear Alkylate Sulfonates" 1996 CEH Marketing Research Report, SRI International.
National Center for Biotechnology Information, National Library of Medicine, National Institutes of Health, Accession No. 1002972-47-5, Bethesda, MD [retrieved on Feb. 9, 2017], 1 pg.
National Center for Biotechnology Information, National Library of Medicine, National Institutes of Health, Accession No. 1135302-36-1, Bethesda, MD [retrieved on Feb. 9, 2017], 1 pg.
National Center for Biotechnology Information, National Library of Medicine, National Institutes of Health, Accession No. 1268022-52-1, Bethesda, MD [retrieved on Feb. 9, 2017], 1 pg.
National Center for Biotechnology Information, National Library of Medicine, National Institutes of Health, Accession No. 1368050-97-8, Bethesda, MD [retrieved on Feb. 9, 2017], 1 pg.
National Center for Biotechnology Information, National Library of Medicine, National Institutes of Health, Accession No. 1368322-89-7, Bethesda, MD [retrieved on Feb. 9, 2017], 1 pg.
National Center for Biotechnology Information, National Library of Medicine, National Institutes of Health, Accession No. 1369346-21-3, Bethesda, MD [retrieved on Feb. 9, 2017], 1 pg.
National Center for Biotechnology Information, National Library of Medicine, National Institutes of Health, Accession No. 1487002-28-7, Bethesda, MD [retrieved on Feb. 9, 2017], 1 pg.
National Center for Biotechnology Information, National Library of Medicine, National Institutes of Health, Accession No. 1547109-89-6, Bethesda, MD [retrieved on Feb. 9, 2017], 1 pg.
National Center for Biotechnology Information, National Library of Medicine, National Institutes of Health, Accession No. 1552249-05-4, Bethesda, MD [retrieved on Feb. 9, 2017], 1 pg.
National Center for Biotechnology Information, National Library of Medicine, National Institutes of Health, Accession No. 1690924-09-4, Bethesda, MD [retrieved on Feb. 9, 2017], 1 pg.
National Center for Biotechnology Information, National Library of Medicine, National Institutes of Health, Accession No. 1692327-84-6, Bethesda, MD [retrieved on Feb. 9, 2017], 1 pg.
National Center for Biotechnology Information, National Library of Medicine, National Institutes of Health, Accession No. 1692517-27-3, Bethesda, MD [retrieved on Feb. 9, 2017], 1 pg.
National Center for Biotechnology Information, National Library of Medicine, National Institutes of Health, Accession No. 1693868-96-0, Bethesda, MD [retrieved on Feb. 9, 2017], 1 pg.

(56) References Cited

OTHER PUBLICATIONS

National Center for Biotechnology Information, National Library of Medicine, National Institutes of Health, Accession No. 1694149-44-4, Bethesda, MD [retrieved on Feb. 9, 2017], 1 pg.
National Center for Biotechnology Information, National Library of Medicine, National Institutes of Health, Accession No. 1695029-38-9, Bethesda, MD [retrieved on Feb. 9, 2017], 1 pg.
National Center for Biotechnology Information, National Library of Medicine, National Institutes of Health, Accession No. 1697631-65-4, Bethesda, MD [retrieved on Feb. 9, 2017], 1 pg.
National Center for Biotechnology Information, National Library of Medicine, National Institutes of Health, Accession No. 1699160-40-1, Bethesda, MD [retrieved on Feb. 9, 2017], 1 pg.
National Center for Biotechnology Information, National Library of Medicine, National Institutes of Health, Accession No. 1702812-08-5, Bethesda, MD [retrieved on Feb. 9, 2017], 1 pg.
National Center for Biotechnology Information, National Library of Medicine, National Institutes of Health, Accession No. 1780282-51-0, Bethesda, MD [retrieved on Feb. 9, 2017], 1 pg.
National Center for Biotechnology Information, National Library of Medicine, National Institutes of Health, Accession No. 1781752-49-5, Bethesda, MD [retrieved on Feb. 9, 2017], 1 pg.
National Center for Biotechnology Information, National Library of Medicine, National Institutes of Health, Accession No. 1781764-76-8, Bethesda, MD [retrieved on Feb. 9, 2017], 1 pg.
National Center for Biotechnology Information, National Library of Medicine, National Institutes of Health, Accession No. 1781768-58.8, Bethesda, MD [retrieved on Feb. 9, 2017], 1 pg.
National Center for Biotechnology Information, National Library of Medicine, National Institutes of Health, Accession No. 1782779-50-3, Bethesda, MD [retrieved on Feb. 9, 2017], 1 pg.
National Center for Biotechnology Information, National Library of Medicine, National Institutes of Health, Accession No. 1782604-69-6, Bethesda, MD [retrieved on Feb. 9, 2017], 1 pg.
National Center for Biotechnology Information, National Library of Medicine, National Institutes of Health, Accession No. 1784189-65-6, Bethesda, MD [retrieved on Feb. 9, 2017], 1 pg.
National Center for Biotechnology Information, National Library of Medicine, National Institutes of Health, Accession No. 654683-71-3, Bethesda, MD [retrieved on Feb. 9, 2017], 1 pg.
National Center for Biotechnology Information, National Library of Medicine, National Institutes of Health, Accession No. 853018-15-2, Bethesda, MD [retrieved on Feb. 9, 2017], 1 pg.
National Center for Biotechnology Information, National Library of Medicine, National Institutes of Health, Accession No. 1697380-32-7, Bethesda, MD [retrieved on Feb. 9, 2017], 1 pg.
Newsam, "The zeolite cage structure" Mar. 1986 *Science*, 231:1093-1099.
Nowak, "The remobilization of metals from iron oxides and sediments by metal-EDTA complexes" 2001 *Water, Air, Soil Pollut.*, 125:243-257.
Opietnik, "Mild Friedel-Crafts Acylation of Furan with Carboxylic Acids and the Heterogeneous Catalyst Couple AlPW12O40/Mg(OH)2" 2016 Current Organic Chemistry, 16:2739-2744.
Park, "Tunable Oleo-Furan Surfactants by Acylation of Renewable Furans" Nov. 2016 *ACS Cent Sci.*, 2(11):820-824.
Park, "An effective one-pot conversion of acid chlorides to aldehydes and ketones" Jun. 2013 *Tetrahedron Letters*, 54(24):3199-3203.
Ravindar, "A Highly Efficient Access to Spiroketals, Mono-unsaturated Spiroketals, and Furans: Hg(II)-Catalyzed Cyclization of Alkyne Diols and Triols" 2011 *Organic Chemistry Letters*, 13(12):3178-3181.
Roberts, "Optimisation of the linear alkyl benzene sulfonation process for surfactant manufacture" 2003 *Org. Process Res. Dev.*, 7:172-184.
Rodriguez, "Kinetics of precipitation of surfactants. I. Anionic surfactants with calcium and with cationic surfactants" 2001 *J. Surfactants Deterg.*, 4:1-14.

Rodriguez, "Precipitation in solutions containing mixtures of synthetic anionic surfactant and soap. I. Effect of sodium octanoate on hardness tolerance of sodium dodecyl sulfate" 1998 *J. Surfactants Deterg.*, 1:321-328.
Rodriquez, "An Efficient Asymmetric Synthesis of Prostaglandin E1" Jan. 1999 *European Journal of Organic Chemistry, Wiley—V C H Verlag Gmbh & Co. KGAA*, DE, 2655-2662.
Rosen, *Surfactants and interfacial phenomena*, 3rd ed.; Wiley-Interscience: New Jersey, 2004. Cover page, title page and table of contents.
Rust, "Surfactants—A Market Opportunity Study Update," United Soybean Board, Omni Tech International, LTD, 2008.
Scamehorn, "Precipitation of mixtures of anionic surfactants. In *Mixed surfactant systems*" 1992 ACS Symposium Series, American Chemical Society: Washington DC, 1992; 501:392-401.
Scheibel, "The evolution of anionic surfactant technology to meet the requirements of the laundry detergent industry" 2015 *J. Surfactants Deterg.*, 7(4):319-328.
Schramm, "Surfactants and their applications" 2003 Marangoni, *Annu. Rep. Prog. Chem.*, Sect. C, 99:3-48.
Schulte, "Thiophene und Selenophene aus a-Propinyl-carbonyl-Verbindungen" 1968 *Chem Ber.*, 101:1540-1552.
Scott, "The biodegradation of surfactants in the environment" 2000 *Biochim. Biophys. Acta, Biomembr.*, 1508:235-251.
Scully, "The Sulfonation of Furan and Furan Homologs. Preparation of Furansulfonamides" 1954 *Org. Chem.*, 19(6):894-901.
Setzkorn, "An evaluation of the river die-away technique for studying detergent biodegradability" 1964 *Am. Oil Chem. Soc.*, 41:826-830.
Shea, "Reversal of cation-induced reduction in glyphosate activity with EDTA" 1984 *Weed Sci.*, 32:802-806.
Shirke, "Modular Assembly of Furotropones and Benzofurotropones, and Study of Their Physicochemical Properties" 2015 *J Org Chem.*, 80:4893-4903.
Showell, *Handbook of detergents, part D: Formulation*; vol. 128, CRC Press Taylor & Francis Group: Florida, 2006. Cover page, title page and table of contents.
Smith, "y-Selective directed catalytic asymmetric hydroboration of 1,1-disubstituted alkenes" 2012 *Chem Commun.*, 48:12180-12182.
Smyth, "Toward a clean alternative to Friedel-Crafts acylation: In situ formation, observation, and reaction of an acyl bis(trifluoroacetyl)phosphate and related structures" 1998 *J. Org. Chem.*, 63:8946-8951.
Snatzke: "Circular dichroism-XLVI" Jan. 1971 Tetrahedron, Elsevier Science Publishers, Amsterdam, NL, 15(27):3645-3653.
Sorrenti, "Amphiphiles in aqueous solution: well beyond a soap bubble." Nov. 2013 *Chem. Soc. Rev.*, 42:8200-8219.
Tago, "Selective production of isobutylene from acetone over alkali metal ion-exchanged BEA zeolites" 2011 *Catal. Today*, 164:158-162.
Tedder, "The use of trifluoroacetic anhydride and related compounds in organic syntheses" 1955 *Chem. Rev.*, 55:787-827.
Tius, "A Synthesis of 2-Alkyl-3-Furioc Acids" 1985 *Tetrahed. Letters*, 26(31):3635-3638.
Tsai, "Development of a green LAB process: alkylation of benzene with 1-dodecene over mordenite" 2003 *Green Chem.*, 5:404-409.
Vautier-Giongo, "Estimate of the Ionization Degree of Ionic Micelles Based on Krafft Temperature Measurements" 2003 *Phys. Chem. B*, 107:5398-5403.
Vlachy, "Role of surfactant headgroup on the counterion specificity in the micelle-to-vesicle transition through salt addition" 2008 *J. Colloid Interface Sci.*, 319:542-548.
Watry, "Comparison of the adsorption of linear alkanesulfonate and linear alkylbenzenesulfonate surfactants at liquid interfaces" 2000 *J. Am. Chem. Soc.*, 122:875-883.
Zimmerman, "Design of hard water stable emulsifier systems for petroleum and bio-based semi-synthetic metalworking fluids" 2003 *Environ. Sci. Technol.*, 37:5278-5288.
Bel'skii, "Catalytic Hydrogenation and Hydrogenolysis of Furan Compounds" 1963 Russ. Chem. Rev., 32(6):307-321.
Cheng, "Production of targeted aromatics by using Diels-Alder classes of reactions with furans and olefins over ZSM-5" 2012 *Green Chem.*, 14:3114-3125.

(56) References Cited

OTHER PUBLICATIONS

Mukaiyama, 1982 *Org. Reactions*, Chap. 3, "The Directed Aldol Reaction," pp. 203-331.

Reddy, "Vapour phase acylation of furan and pyrrole over zeolites" 1998 *Catalysis Letts.*, 54:95-100.

Scully, "The sulfonation of furan and furan homologs. Preparation of furano sulfonamides" 1954 *J. Org. Chem.*, 19(6):894-901.

Bartoli, "SiO 2—Supported CeCl 3 . 7H 2 O-NaI Lewis Acid Promoter: Investigation into the Garcia Gonzalez Reaction in Solvent-Free Conditions [bottom]" Aug. 2007 Journal of Organic Chemistry, 72(16):6029-6036.

D'Auria, "Synthesis of 4-ylidenebutenolides and 4-oxo-2-enoic acid methyl esters from 5-methoxy-2-furyl carbinols" Jan. 1980 Tetrahedron, 36(20-21):3071-3074.

El Dessouky, "Radiolysis of 1-(2-furanyl)-1-pentanone in the presence of atmospheric oxygen" Oct. 1985 Journal of Radioanalytical and Nuclear Chemistry, 92(1):51-57.

Gensler, "1,4-Diketones from skipped acetylenes" Oct. 1978 Journal of Organic Chemistry, 43(21):4081-4085.

Kawabe, "Studies on Alkylated Furan Derivatives. Ill. Synthesis and Antimicrobial Activity of 5-Alkyl-2-furamide and 5-Alkyl-N-alkyl-2-furamide", 1960 Yakugaku Zasshi, 80(1960):58-62.

Nazorova, "610 Khimiya Geterotsiklicheskikh Soedinenii Letters to the Editor Organolithium Compounds of Pyromucic Acid and of Furyural Acetals" Jan. 1967 Dictionary of Organic Compounds [Russian Translation], 3(4):610.

Ohta, "The birch reduction of heterocyclic compounds V Birch reduction of 2- and 5-acylfuran-3-carboxylic acids and reductive elimination of 2-arylmethoxymethyl)furan-3-carboxylic acids" Jul. 2000 Journal of Heterocyclic Chemistry, 37(4);751-755.

Piao, "Synthesis of 9-(5-pentyl-2-furyl)nonanoic acid" Jan. 1999 Chinese Chemical Letters, Elsevier, Amsterdam, NL, 10(9):737-738.

Ragan, "Investigation of Methods for Seven-Membered Ring Synthesis: A Practical Synthesis of 4-Oxo-5,6,7,8-tetrahydro-4H-cyclohepta[b]furan-3-carboxylic Acid" Jul. 2001 *Org. Proc. Res. Dev.*, 5(5):498-507.

Robinson, "Directive Effects in Acylation of Methyl Furan-2-carboxylate" Dec. 1966 Journal of Organic Chemistry, 31(12):4252-4252.

Scholz, "*Friedel-Crafts-Reaktion* von 2-Methylfuran mit gesattigten und cx,p-ungesattigten Saureanhydriden . . . " *Liebigs Ann. Chem.*, 1935-1950.

Park et al., "Tunable Oleo-Furan Surfactants by Acylation of Renewable Furans," *ACS Cent. Sci.*, 2016; 2:820-824.

* cited by examiner

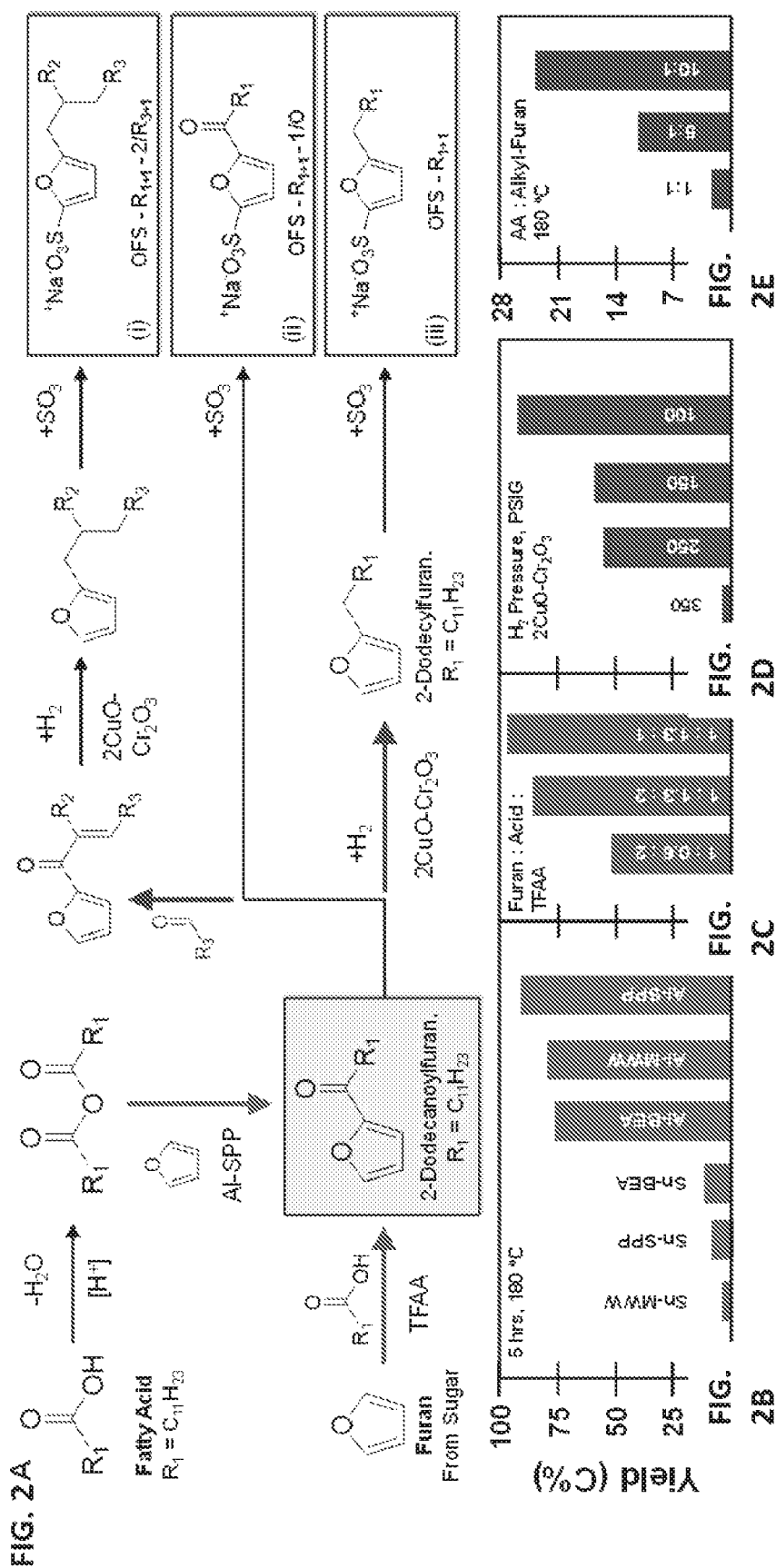

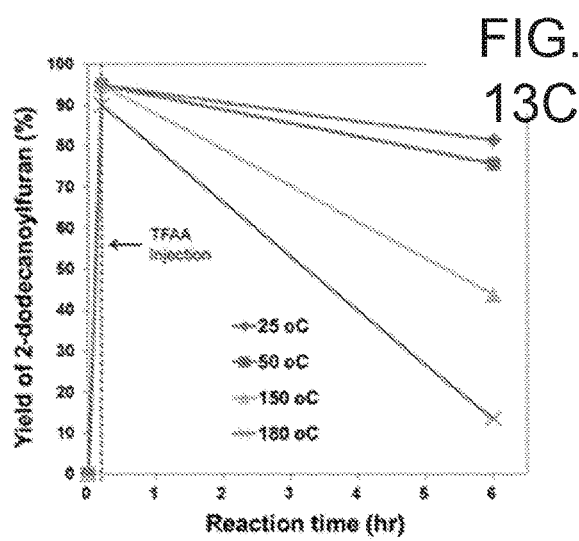
FIG. 13C
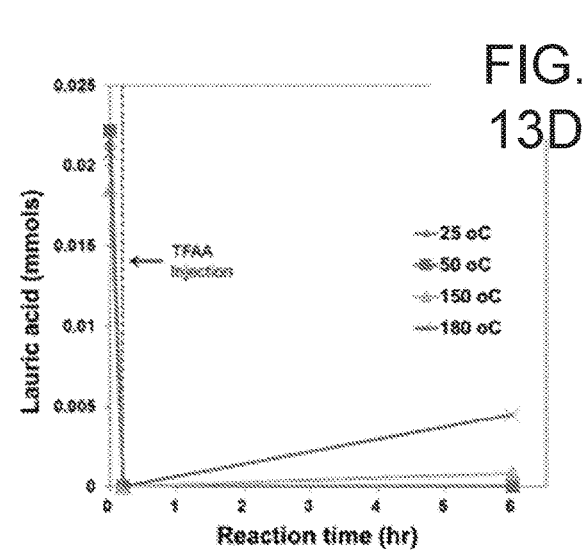
FIG. 13D
FIG. 13E
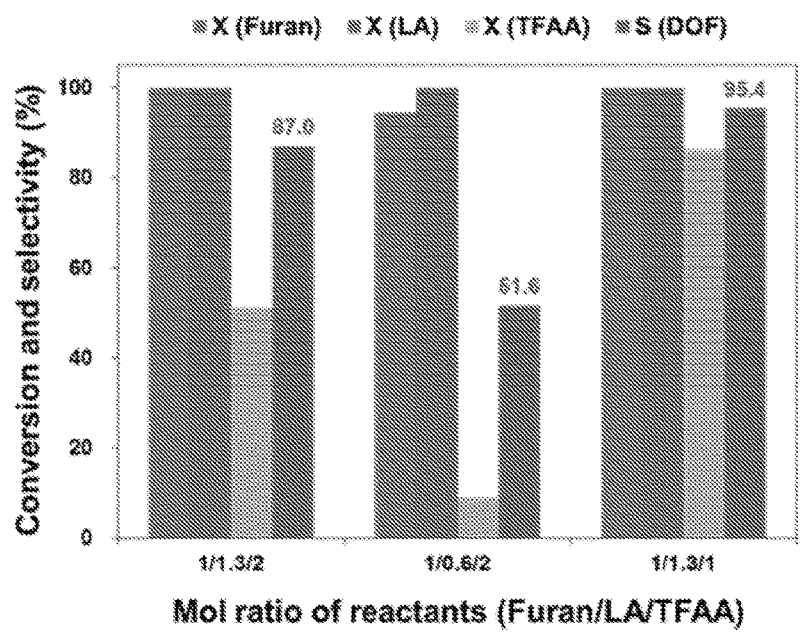

FIG. 13F
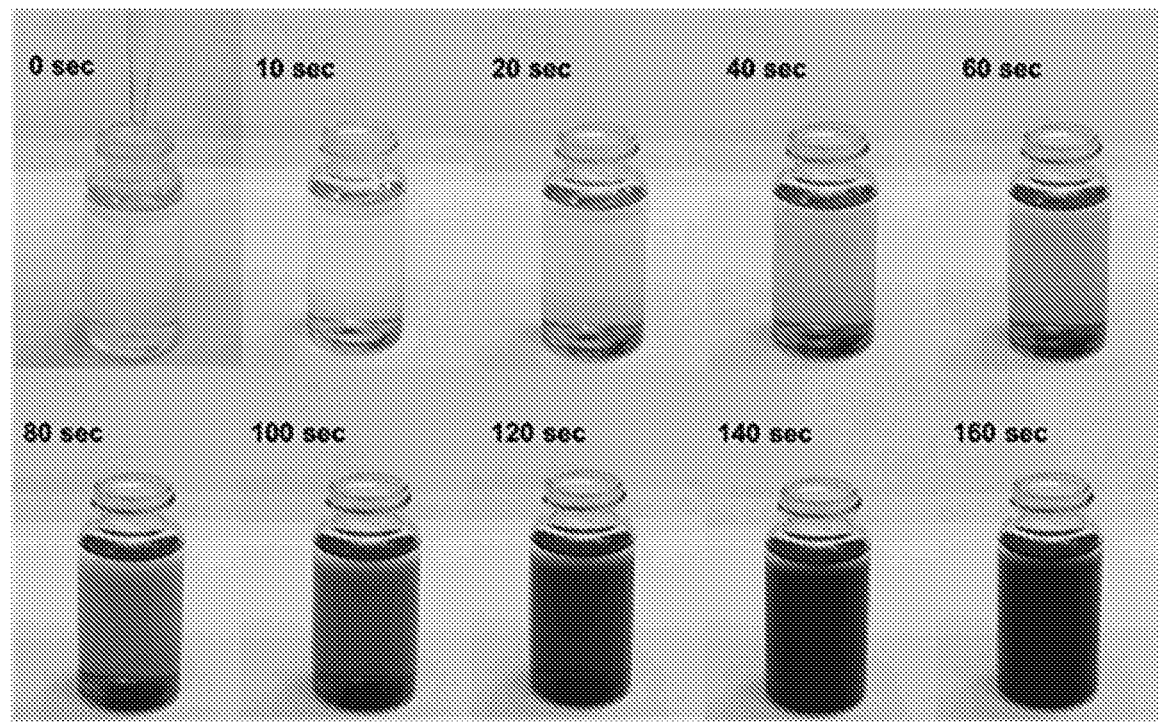
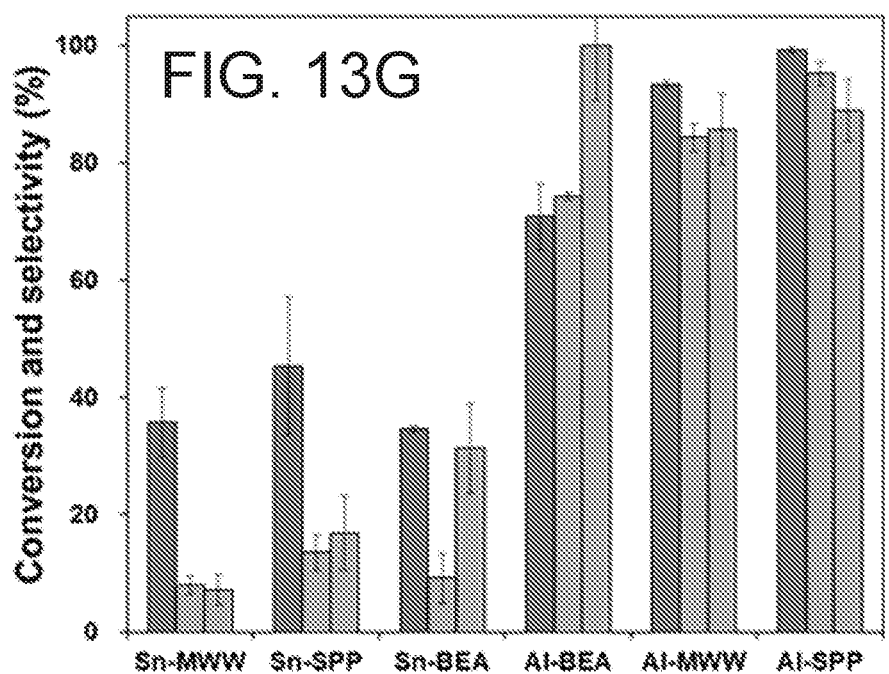

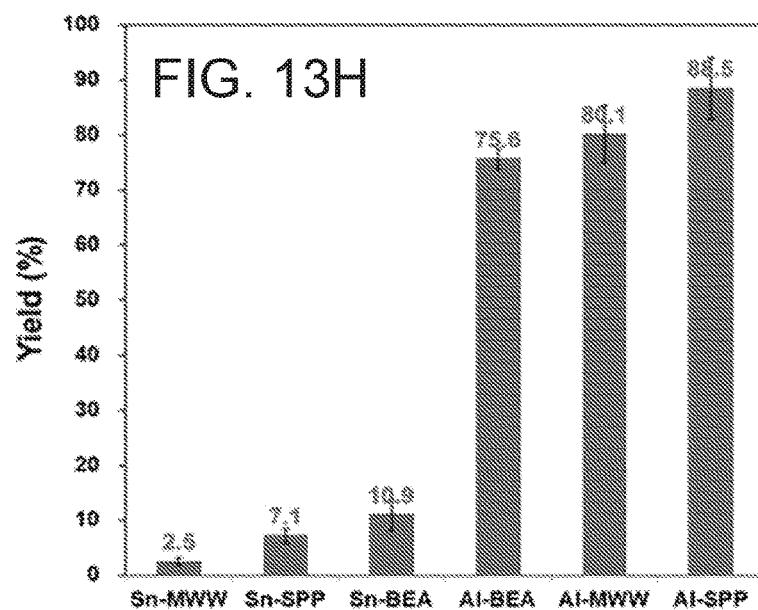
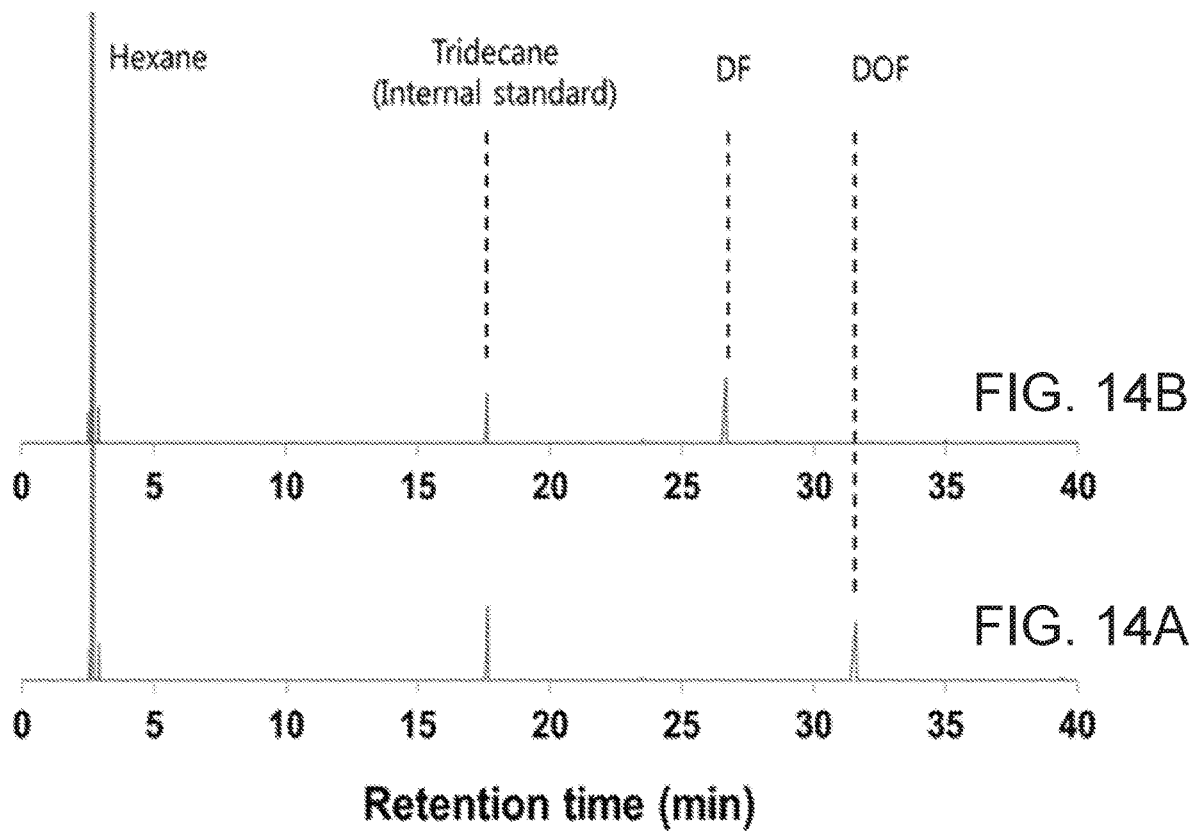

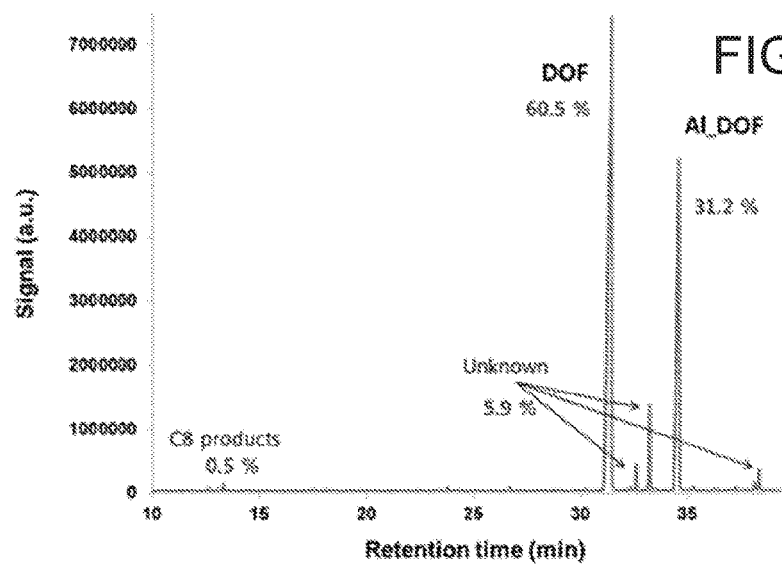
FIG. 15B
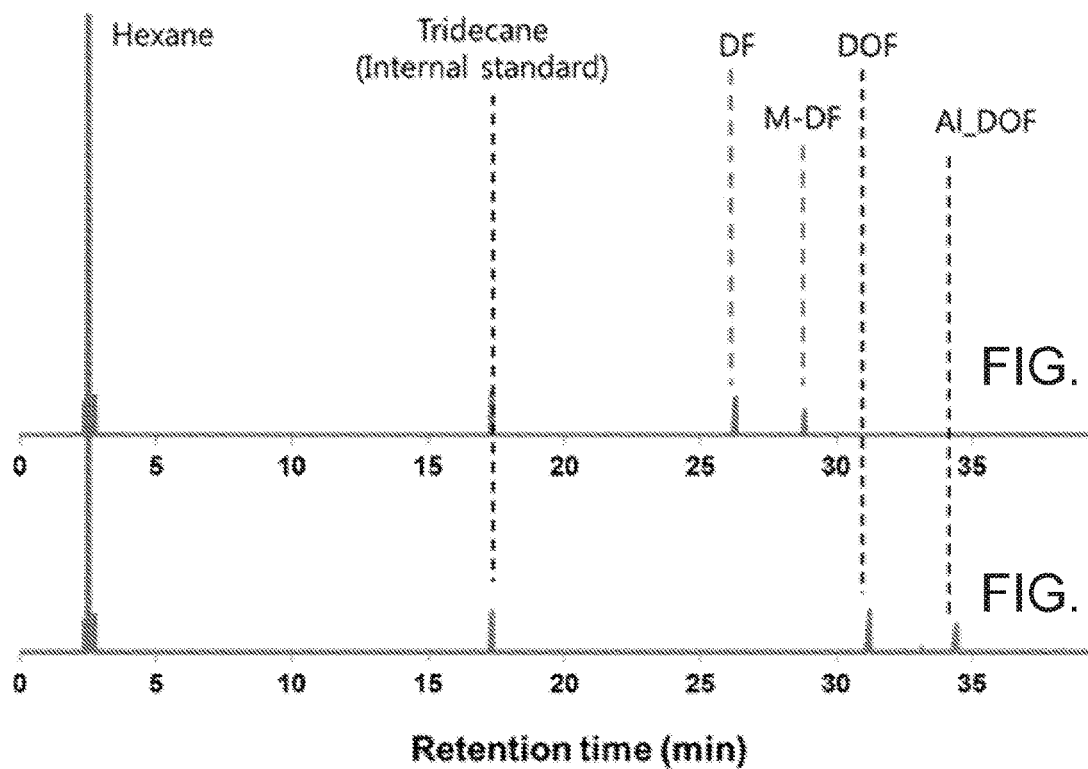
FIG. 15D
FIG. 15C

FIG. 21A
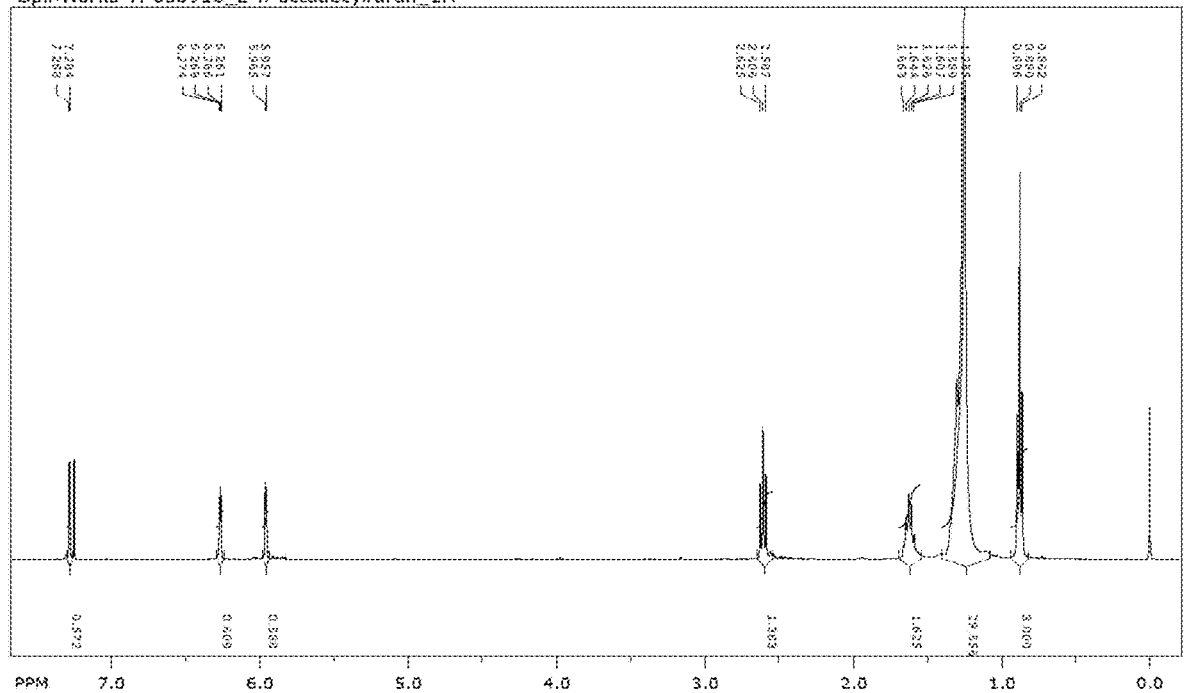
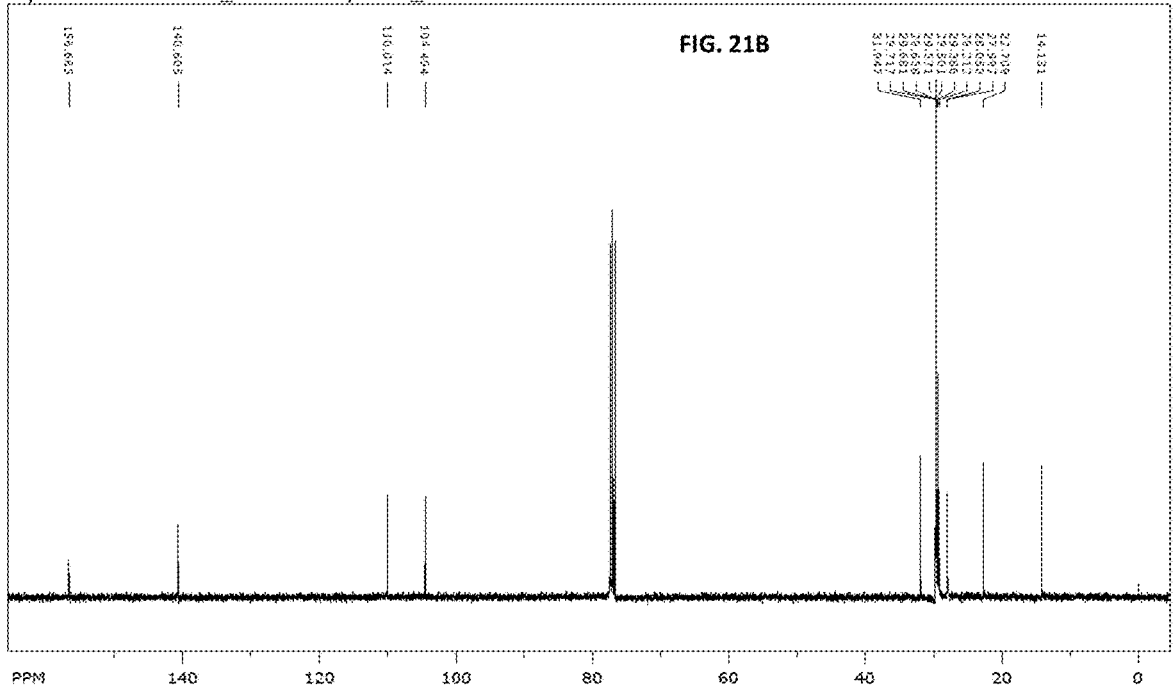
FIG. 21B

FIG. 27A
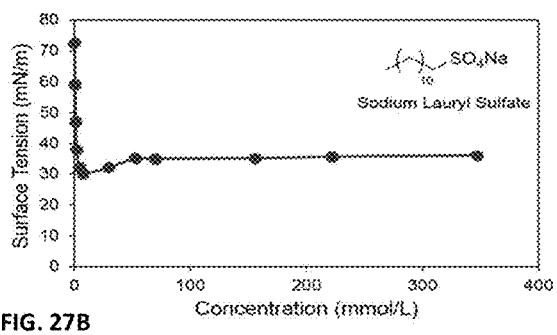 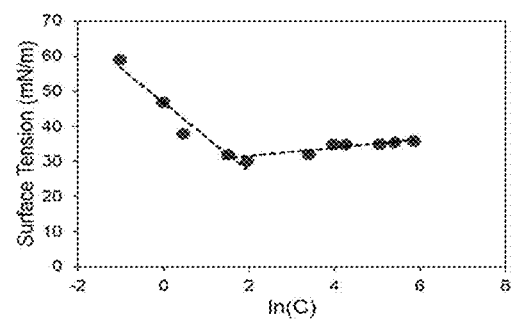
FIG. 27B
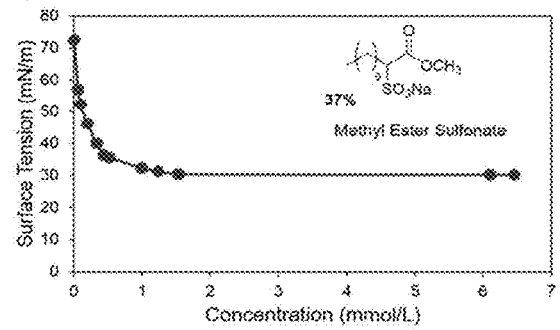 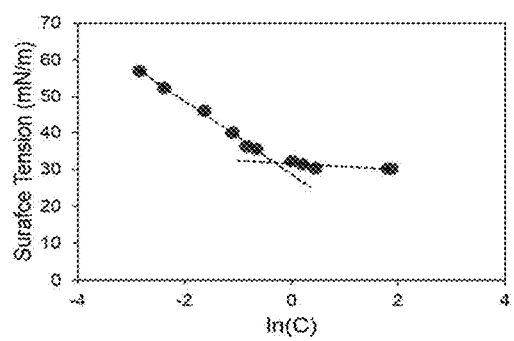
FIG. 27C
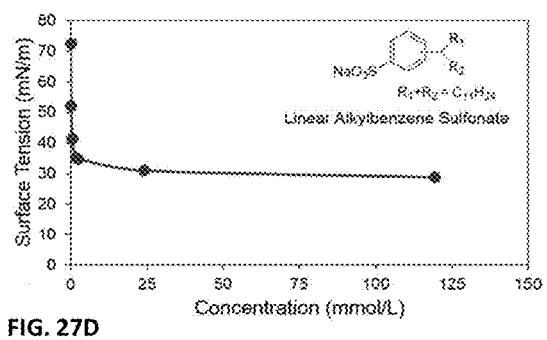 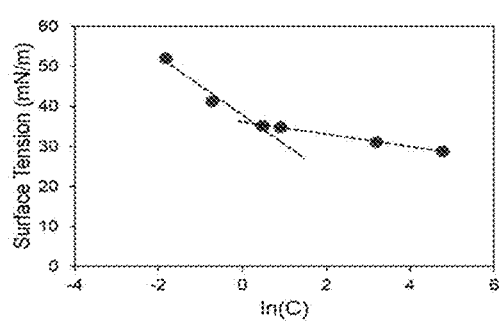
FIG. 27D
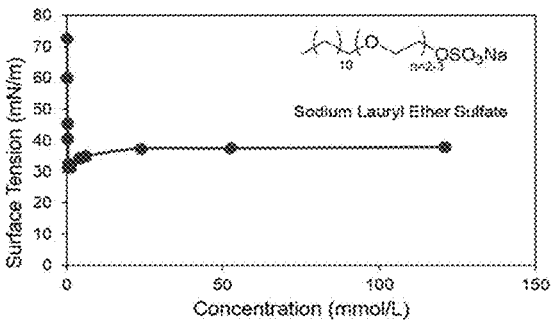 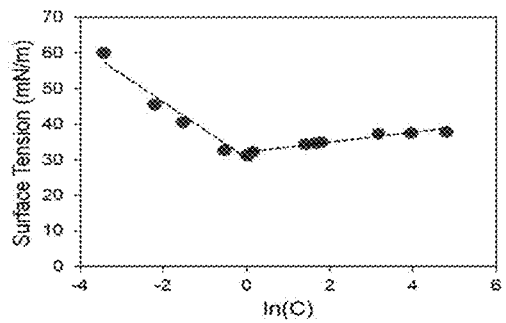

FIG. 28A
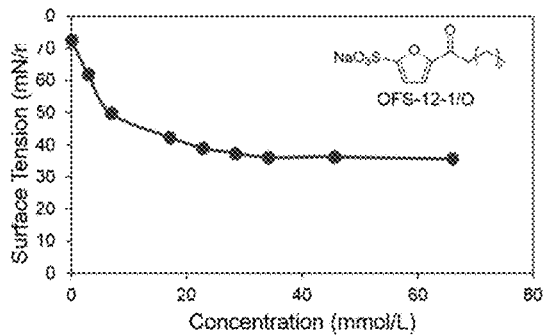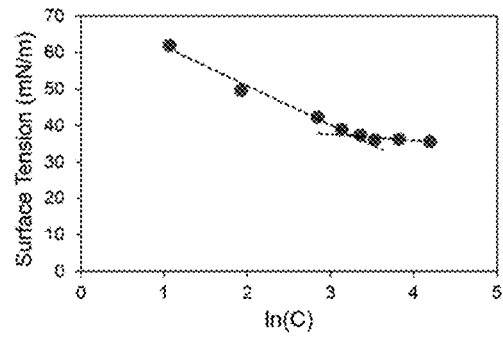
FIG. 28B
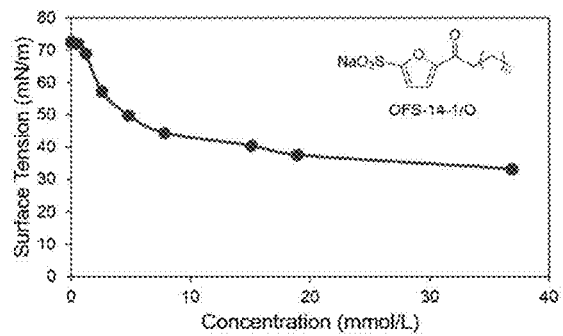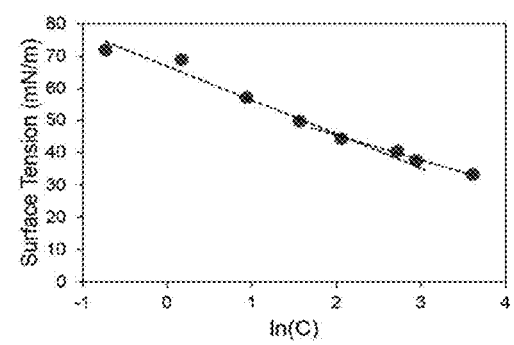
FIG. 28C
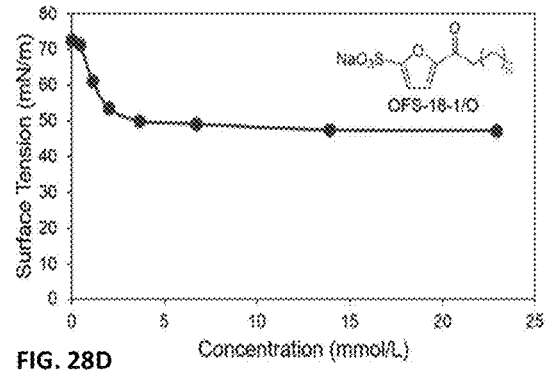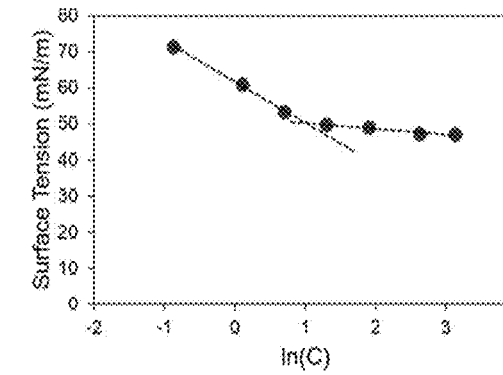
FIG. 28D
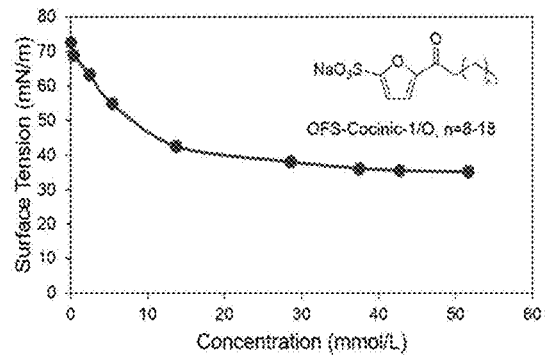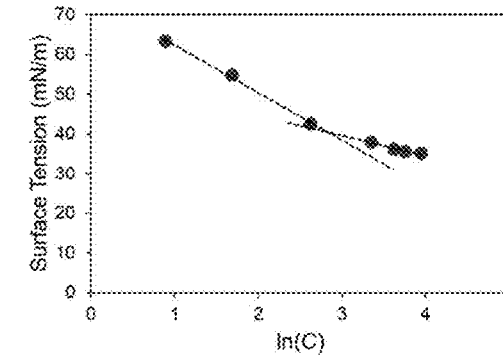

FIG. 29A
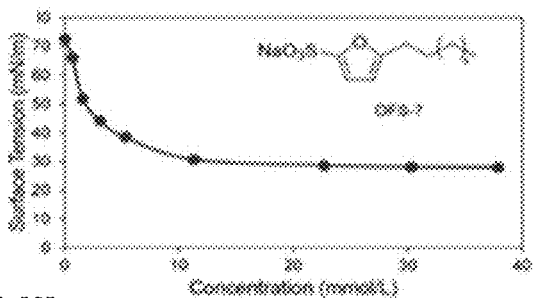 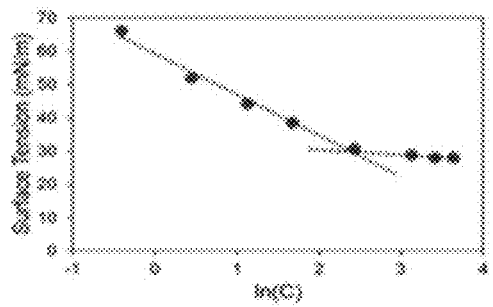
FIG. 29B
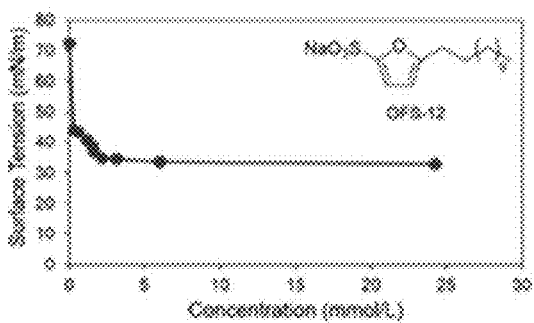 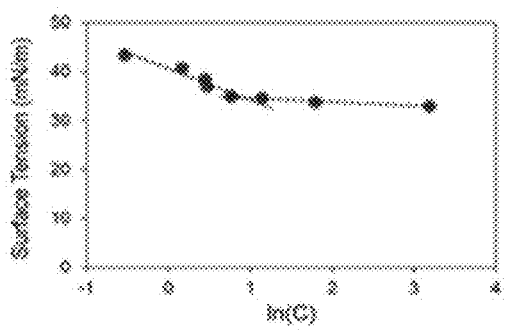
FIG. 29C
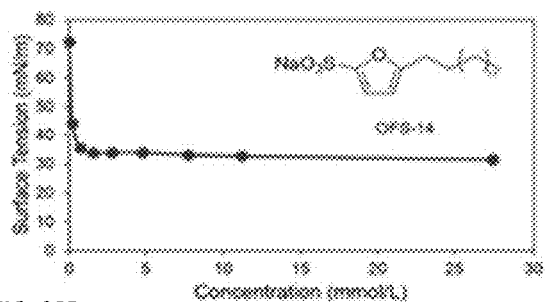 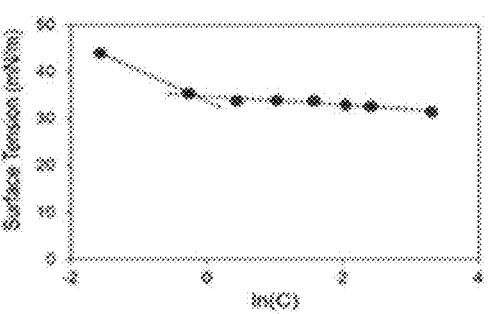
FIG. 29D
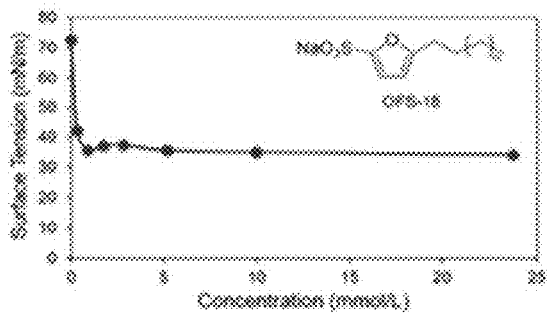 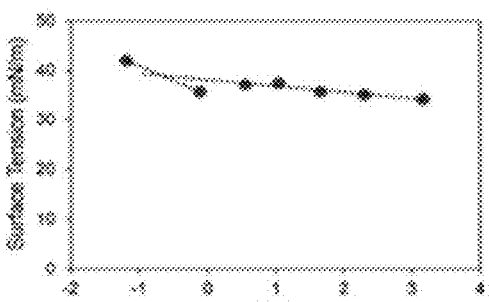

FIG. 29E
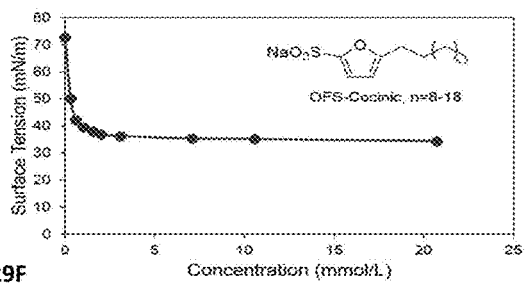
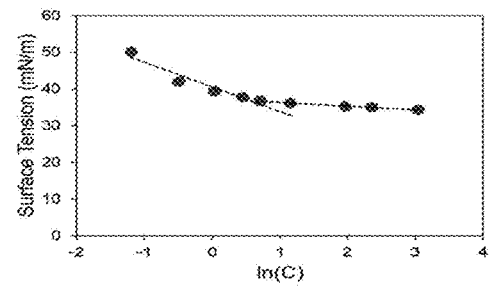
FIG. 29F
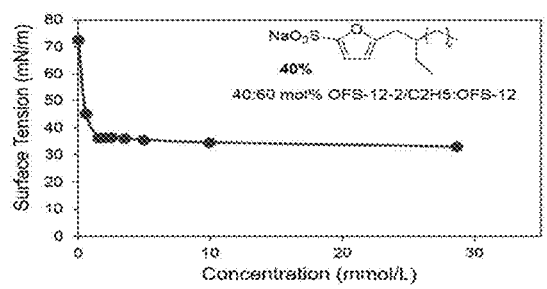
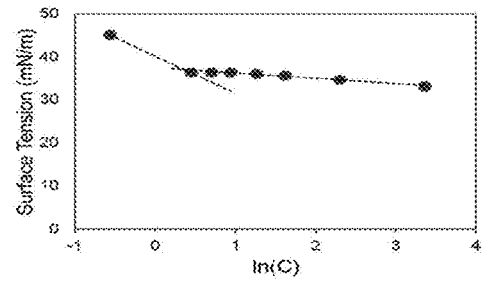
FIG. 29G
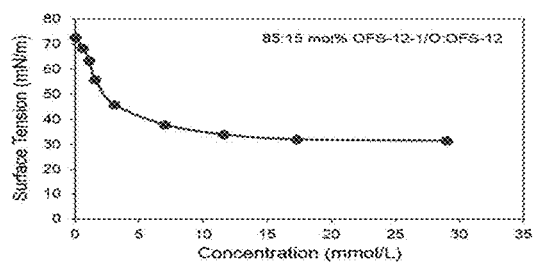
FIG. 30
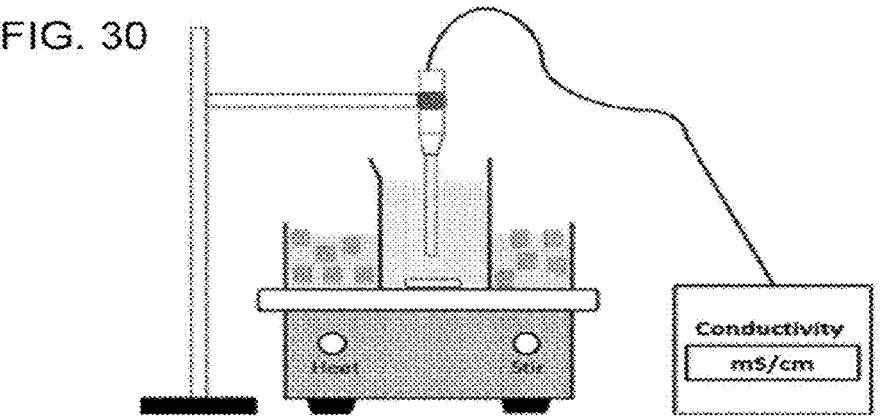

AROMATIC SURFACTANTS

PRIORITY

This application is the § 371 U.S. National Stage of International Application No. PCT/US2016/060775, filed 7 Nov. 2016, which claims priority to United States Provisional Application No. 62/252,200 filed on Nov. 6, 2015 entitled Methods of Forming Aromatic and Linear Chain Containing Compounds; and 62/403,305 filed on Oct. 3, 2016 entitled Aromatic Surfactants; the entire disclosures of which are incorporated herein by reference thereto.

GOVERNMENT FUNDING

This invention was made with government support under DE-SC0001004 awarded by the Department of Energy. The government has certain rights in the invention.

SUMMARY

Disclosed are compounds of the Formula 1

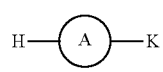

(1)

wherein A is an aromatic moiety; H is a hydrophobic group comprising a main alkyl chain having from about 3 to about 26 carbon atoms and comprising a $C_2$ or greater alkyl chain branched from the main alkyl chain; and K is a hydrophilic group.

Also disclosed are compounds of formula 3

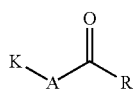

(3)

wherein K is a hydrophilic group, A is an aromatic moiety and R is a hydrophobic group comprising a main alkyl chain having from about 3 to about 26 carbon atoms.

Also disclosed are compounds of formula 4:

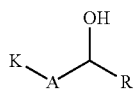

(4)

wherein K is a hydrophilic group, A is an aromatic moiety and R is a hydrophobic group comprising a main alkyl chain having from about 3 to about 26 carbon atoms.

Also disclosed are compounds of formula 5:

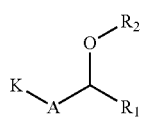

(5)

wherein K is a hydrophilic group, A is an aromatic moiety and $R_1$ is a hydrophobic group comprising a main alkyl chain having from about 1 to about 26 carbon atoms; and $R_2$ is a hydrophobic group comprising a main alkyl chain having from about 1 to about 26 carbon atoms.

Also disclosed are compounds of formula 6:

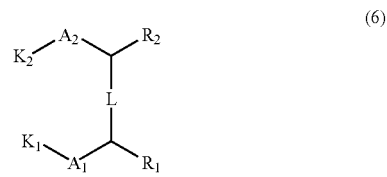

(6)

wherein $K_1$ and $K_2$ are independently hydrophilic groups, $A_1$ and $A_2$ are independently aromatic moieties, $R_1$ is a hydrophobic group comprising a main alkyl chain having from about 1 to about 26 carbon atoms; $R_2$ is a hydrophobic group comprising a main alkyl chain having from about 1 to about 26 carbon atoms; and L is a linking group.

Also disclosed are compounds of formula 8:

(8)

wherein K is a hydrophilic group, A is an aromatic moiety, $R_1$ is a hydrophobic group comprising a main alkyl chain having from about 1 to about 26 carbon atoms, and $R_2$ is optional and can be a hydrophobic group comprising a main alkyl chain having from about 1 to about 26 carbon atoms, wherein K, $R_1$ and A are all attached to the same carbon atom.

Also disclosed are compounds selected from:

Ethoxylated Aromatic Surfactant

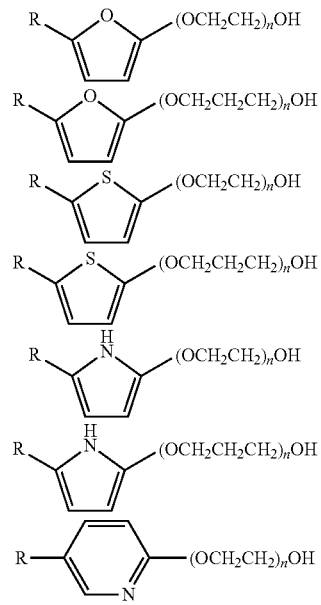

3

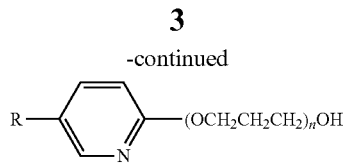

Also disclosed are compounds formed according to the following reaction scheme:

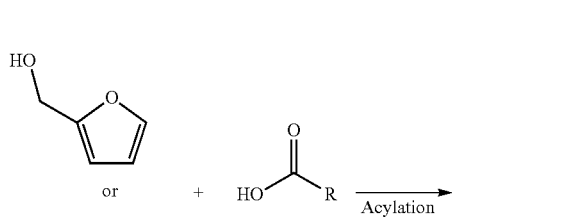

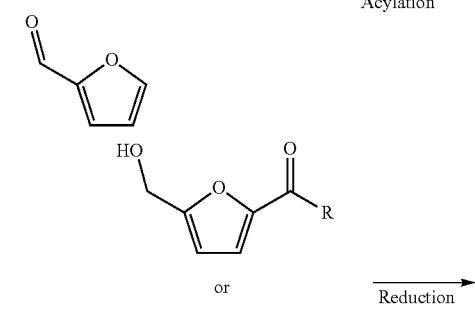

Also disclosed are compounds formed according to the following reaction scheme:

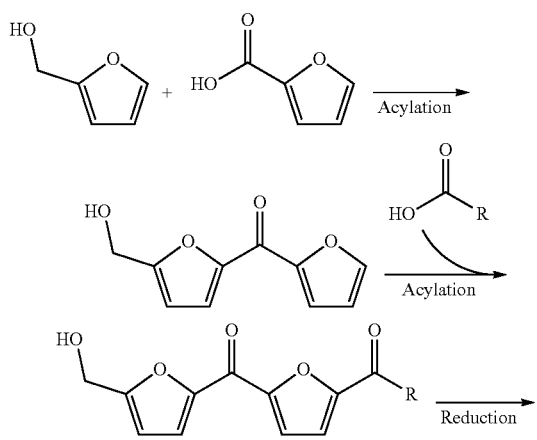

4

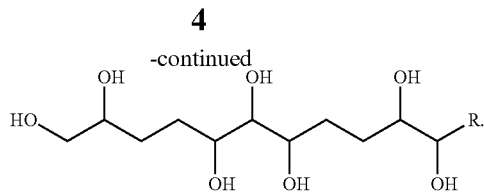

Also disclosed are compounds of formula 9:

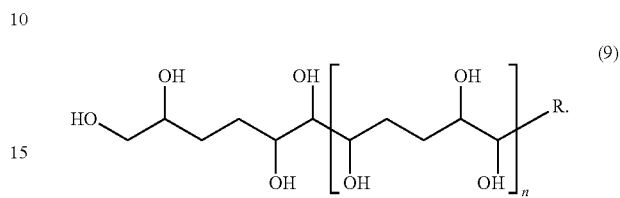

(9)

Also disclosed are compounds formed according to the following reaction scheme:

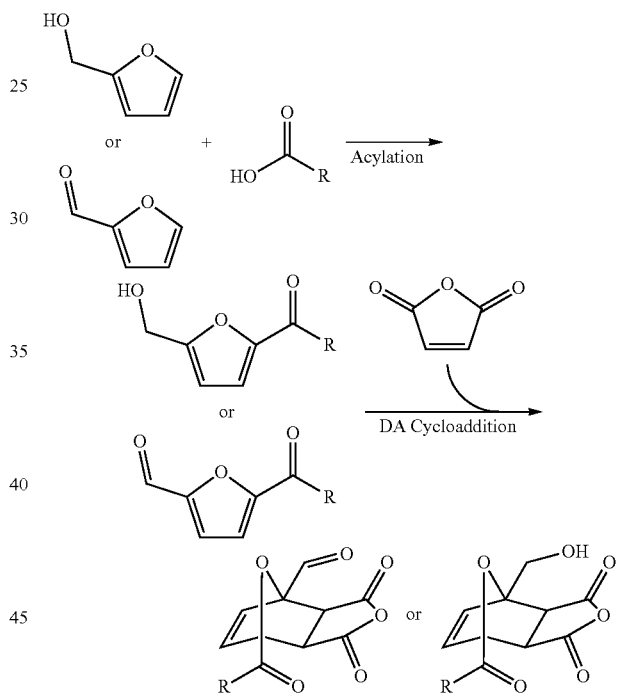

Also disclosed are compounds selected from:

Di-Substituted, Acylated Surfactant

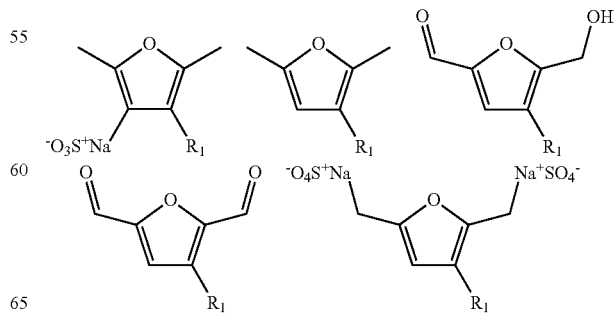

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF FIGURES

FIGS. 2A, 2B, 2C, 2D and 2E show the reaction of furan with the anhydride form of fatty acids (R1) with a solid acid such as Al-SPP zeolite produces acylated furan ketone at ~90% yield. Alternatively, direct acylation of fatty acids (R1) occurs in two integrated steps via trifluoroacetic anhydride (TFAA). Three classes of OFS include: (i) aldol condensation, reduction and sulfonation to branched surfactants (OFS-R1+1-2/R3+1), (ii) direct sulfonation (OFS-R1+1-1/O), or (iii) reduction to a linear chain and sulfonation (OFS-R1+1) (FIG. 2A); Furan acylation with solid acid catalysts for five hours, 180° C. (FIG. 2B); Combined anhydride formation and furan acylation with varying ratios of furan, fatty acid, and TFAA (FIG. 2C); Hydrogenation of 2-dodecanyolfuran on copper chromite at 220° C. with varying hydrogen pressure (FIG. 2D); and Aldol condensation with varying ratios of acetaldehyde (AA) and 2-dodecanoylfuran at 180° C. (FIG. 2E).

FIGS. 13C, 13D and 13E show the change in the yield of 2-dodecanoylfuran (FIG. 13C); lauric acid concentration (FIG. 13D) during a reaction; acylation of furan and lauric acid with different molar ratios of reactants (FIG. 13E); FIG. 13F shows the reaction progression of acylation of furan with lauric acid using TFAA with time; FIG. 13G shows the conversion and selectivity with lauric anhydride over various solid acid catalysts; and FIG. 13H shows yield in furan acylation with lauric anhydride over various solid acid catalysts.

FIGS. 14A and 14B show typical GC profiles of a reactant mixture (FIG. 14A) and products in hydrogenation of 2-dodecanoylfurant (DOF: 2-dodecanoylfuran, DF: 2-dodecylfuran)

FIGS. 15A and 15B show typical GC profiles of product mixtures after aldol condensation—concentrated samples by rotary evaporator (FIG. 15A) and purified and separated by flash chromatography (FIG. 15B); and FIGS. 15C and 15D show typical GC profiles of a reactant mixture (FIG. 15C) and products (FIG. 15D) in hydrogenation of DOF and Al_DOF (DOF: 2-dodecanoylfuran, Al_DOF: aldol product, DF: 2-dodecylfuran, M-DF: mono-ethyl branched dodecylfuran).

FIGS. 21A and 21B show the $^1$H NMR and $^{13}$C NMR of 2-n-octadecylfuran in CDCl$_3$.

FIGS. 27A, 27B, 27C and 27D show plots of surface tension versus surfactant concentration of commercial surfactants: sodium Lauryl Sulfate (SLS) (FIG. 27A), Methyl Ester Sulfonate (MES) (FIG. 27B), Linear Alkylbenzene Sulfonate (LAS) (FIG. 27C) and, Sodium Lauryl Ether Sulfate (SLES) (FIG. 27D).

FIGS. 28A, 28B, 28C and 28D show plots of surface tension versus surfactant concentration of renewable OFS-n-1/O surfactants: OFS-12-1/O (FIG. 28A), OFS-14-1/O (FIG. 28B), OFS-18-1/O (FIG. 28C) and OFS-Cocinic-1/O, n=8-18 (FIG. 28C).

FIGS. 29A, 29B, 29C, 29D, 29E, 29F and 29G show plots of surface tension versus surfactant concentration of renewable OFS-n surfactants: OFS-7 (FIG. 29A), OFS-12 (FIG. 29B), OFS-14 (FIG. 29C), OFS-18 (FIG. 29D), OFS-Cocinic, n=8-18 (FIG. 29E), 40:60 mol % OFS-12-2/C2H5: OFS-12 (FIG. 29F) and, 85:15 mol % OFS-12-1/O:OFS-12 (FIG. 29G).

FIG. 30 depicts the apparatus utilized for the measurement of Krafft points.

DETAILED DESCRIPTION OF ILLUSTRATIVE EMBODIMENTS

Figure 1A:
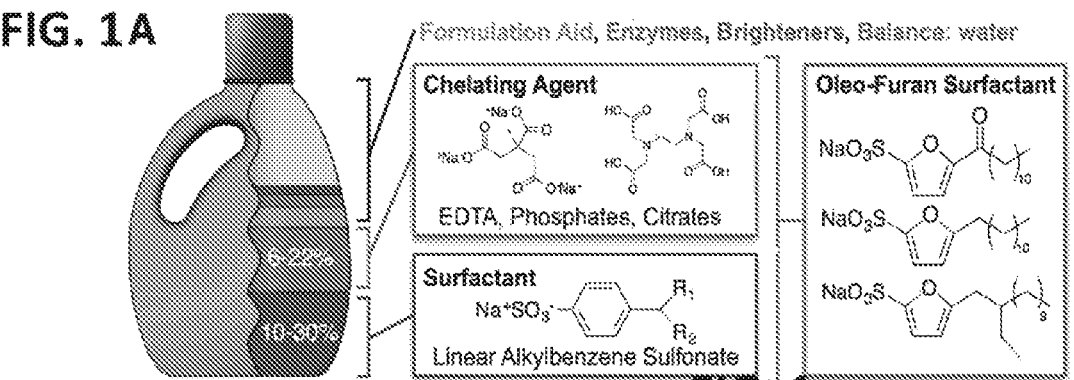
FIGS. 1A, 1B and 1C show water-based linear alkylbenzene sulfonate (LAS) surfactants require metal chelating agents, both of which can be replaced by disclosed aromatic surfactants (OFS) (FIG. 1A); preparation of disclosed aromatic surfactants utilizes selective addition of hydrophobic alkyl-chain tails with or without added branching to aromatic linkers connected to hydrophilic heads such as sulfonates (FIG. 1B); and disclosed surfactants forms micelles characterized by dynamic light scattering (FIG. 1C).
Figure 1B:
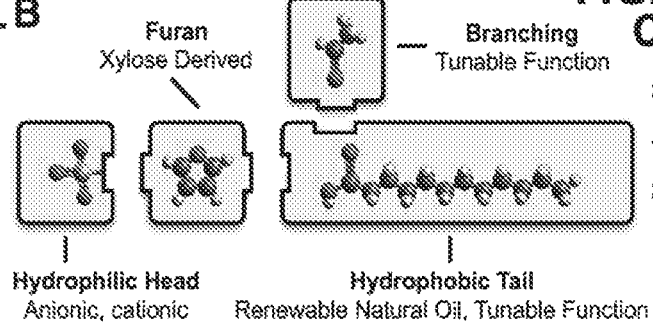
Figure 1C:
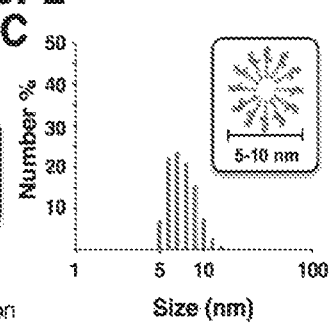

One skilled in the art will appreciate that the methods described herein can be practiced with embodiments other than those disclosed. The disclosed embodiments are presented for purposes of illustration and not limitation. One will also understand that components of the methods depicted and described with regard to the figures and embodiments herein may be interchangeable.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a conductive trace that "comprises" silver may be a conductive trace that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects are present. For example, a "second" substrate is merely intended to differentiate from another infusion device (such as a "first" substrate). Use of "first," "second," etc. in the description above and the claims that follow is also not necessarily intended to indicate that one comes earlier in time than the other.

As used herein, "alkyl" is an unsubstituted or substituted saturated hydrocarbon chain radical having from 1 to about 12 carbon atoms; from 1 to about 10 carbon atoms; from about 1 to about 6 carbon atoms; or from about 1 to about 4 carbons. It should also be understood that an alkyl moiety can be a combination of two or more alkyl moieties. Illustrative, non-limiting examples of alkyl groups include, for example, methyl, ethyl, propyl, iso-propyl, and butyl. A C2 to C4 substituted or unsubstituted alkyl radical, for example refers to a C2 to C4 linear alkyl chain that may be unsubstituted or substituted. If the C2 to C4 linear alkyl chain is substituted with an alkyl radical, the carbon number of the alkyl radical increases as a function of the number of carbons in the alkyl substituent.

As used herein, "anhydride" refers to a chemical compound that includes two acyl (a function group derived by the removal of one or more hydroxyl groups from an oxoacid, it contains a double bonded oxygen atom and an alkyl group (e.g., RC(=O), where R is an alkyl group) groups bonded to the same oxygen atom (—(O=)COC(=O)—). The anhydride can have any types of alkyls bonded to the two terminal carbons, and the two alkyls need not be the same.

As used herein, "aromatic" refers to a major group of unsaturated cyclic hydrocarbons containing one or more rings. An aromatic group may contain carbon (C), nitrogen (N), oxygen (O), sulfur (S), boron (B), or any combination thereof. At least some carbon is included. Aromatic includes both aryl and heteroaryl rings. The aryl or heteroaryl ring may be further substituted by additional aliphatic, aromatic, or other radicals. Illustrative five membered aromatic groups can include, for example furan, thiophene, pyrrole, imidazole, triazole, dithiole, oxathiole, isoxazole, oxazole, thiazole, isothiazole, and oxadizole. Illustrative six membered aromatic groups can include, for example benzene, pyridine, pyran, dioxin, pyridazine, pyrimidine, pyrazine, triazine, and oxazine. Illustrative double ring aromatics include, for example, naphthalene, tetrahydronapthalene, indene, isoindene, benzofuran, isobenzofuran, benzothiophene, indole, quinolone, isoquinoline, quinazoline, anthracene, and phenanthrene for example. In some embodiments, aromatic groups may include furan, thiophene, pyrrole, imidazole, benzene, pyridine, naphthalene, and tetrahydronaphthalene. In some embodiments, aromatic groups may include furan, thiophene, and pyrrole. In some embodiments, aromatic groups may include furan. In some embodiments, aromatic groups may include benzene. An aromatic containing compound refers to a compound that includes an aromatic group, as discussed above. The aromatic containing compound may also additional include any other groups or atoms.

As used herein, "hydrophilic" refers to a water soluble portion of a molecule that can either carry a formal charge, ionic, or can be neutral, non-ionic. As used herein, "ionic" means a hydrophilic group that carries a formal positive charge, negative charge or both. As used herein, "anionic" means a hydrophilic group that is typically a neutralized acid and has a negative charge that is balanced by a positive counterion. Anionic hydrophilic groups are the most commonly used type of hydrophilic group in surfactants. Typical anionic hydrophilic groups include but are not limited to the sodium (Na+) form of carboxylic acids, sulfates, sulfonates, and phosphates. As used herein, "cationic" means a hydrophilic group that has a positive charge and is balanced by a negative counter ion, for example chloride (Cl−). Typical cationic hydrophilic groups are quaternary ammonium compounds that contain a nitrogen group bound to 4 other atoms. As used herein, "zwitterionic" means a hydrophilic groups that contains both cationic and anionic groups. As used herein, "nonionic" means a hydrophilic group that does not contain a formal charge like the ionic groups. Typically, nonionic groups contain carbon, hydrogen, oxygen and nitrogen, with the most common form being based on ethylene oxide to form ethoxylates. The ethoxylate hydrophilic group is typically connected via an ether linkage to the rest of the molecule, but can also be connected via an ester, amine, or amide linkage. Other nonionic groups can be amine ethoxylates, polyols and polyol derivatives, such as glycerol, propanediol, xylitol, sorbitol, mono and polysaccharide derivatives, such as glucose, sucrose, maltose, or xylose derivatives, and polyol amines, such as glucamine or xylosamine.

As used herein, "hydrophobic" means a portion of a molecule that is generally insoluble in water and is usually a hydrocarbon. A hydrocarbon generally refers to an alkyl chain. In some embodiments, a hydrocarbon can refer to a moiety that can include between 3 and 26 carbons, in some embodiments from 6 to 26 carbons. The hydrocarbon can be linear, branched, cyclic or any combination thereof. In some embodiments, a hydrocarbon can include only carbon and hydrogen atoms and in some embodiments it could be substituted with one or more groups. The hydrocarbon can be saturated (there are only single bonds in the hydrocarbon) or unsaturated (there is at least one double or triple bond in the hydrocarbon).

As used herein, "hydroxyl group" refers to a substituent group of formula —OH.

As used herein, "ketone" refers to the group C=O that is bonded to two other atoms, and methylene refers to the group CH2 that is also bonded to two other atoms (e.g., it is saturated).

Unless otherwise stated, as employed herein, when a moiety (e.g., alkyl, or alkenyl) is described as "substituted" it is meant that the group optionally has from one to four, from one to three, or one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

For any method disclosed herein that includes discrete steps, the steps may be conducted in any feasible order, unless context indicates otherwise. And, as appropriate, any combination of two or more steps may be conducted simultaneously.

All headings are for the convenience of the reader and should not be used to limit the meaning of the text that follows the heading, unless so specified.

The complete disclosure of all patents, patent applications, and publications, and electronically available material cited herein are incorporated by reference in their entirety.

The surface energy of droplets, bubbles, and foams determines the efficacy of applications in food (M. A. Augustin, Y. Hemar, Nano- and micro-structured assemblies for encapsulation of food ingredients. *Chemical Society Reviews* 38, 902-912 (2009)10.1039/B801739P)), agriculture, cleaning (J. Falbe, *Surfactants in Consumer Products*. (Springer-Verlag, Heidelberg Germany, 1987)), and drug delivery (J. H. Fendler, Polymerized Surfactant Vesicles: Novel Membrane Mimetic Systems. *Science* 223, 888-894 (1984); and A. Sorrenti, O. Illa, R. M. Ortuno, Amphiphiles in aqueous solution: well beyond a soap bubble. *Chemical Society Reviews* 42, 8200-8219 (2013)10.1039/C3CS60151J)) and can be optimized for each use by chemical surfactants. Many approaches to surfactant design have utilized commodity chemicals to provide both hydrophilic (water engaging) and hydrophobic (oil engaging) functionality from low-cost feedstocks. The use of surfactants with eight to eighteen saturated carbon atoms combined with a polar function has been particularly useful within aqueous systems (J. Falbe, *Surfactants in Consumer Products*. (Springer-Verlag, Heidelberg Germany, 1987)), as the carbon chains aggregate into micelles that can trap oils or stabilize active ingredients within water. This approach has worked in soap and detergent technologies for over a century, but modern variations of these surfactants based on fossil fuel precursors exhibit performance limitations inherent to their molecular structure (J.-G. Ma, B. J. Boyd, C. J. Drummond, Positional Isomers of Linear Sodium Dodecyl Benzene Sulfonate: Solubility, Self-Assembly, and Air/Water Interfacial Activity. *Langmuir* 22, 8646-8654 (2006); published online Epub2006/10/01 (10.1021/la0602822); and M. R. Watry, G. L. Richmond, Comparison of the Adsorption of Linear Alkanesulfonate and Linear Alkylbenzenesulfonate Surfactants at Liquid Interfaces. *Journal of the American Chemical Society* 122, 875-883 (2000); published online Epub2000/02/01 (10.1021/ja9917666)). In addition to modifying interfacial surface energy, surfactants are characterized by their ability to make and stabilize foams, to wet porous materials such as fibers and particles, and to operate in aggressive conditions such as high temperature or hard water (A. Maneedaeng, A. E. Flood, K. J. Haller, B. P. Grady, Modeling of Precipitation Phase Boundaries in Mixed Surfactant Systems Using an Improved Counterion Binding Model. *Journal of Surfactants and Detergents* 15, 523-531 (2012); published online Epub2012//(10.1007/s11743-012-1353-0)). The breadth of performance targets is sufficiently large that modern surfactant structures cannot be independently optimized for all properties, requiring the use of substantial additives for effective application (J. Falbe, *Surfactants in Consumer Products*. (Springer-Verlag, Heidelberg Germany, 1987); and J. B. Zimmerman, A. F. Clarens, K. F. Hayes, S. J. Skerlos, Design of Water Stable Emulsifier Systems for Petroleum and Bio-Based Semi-Synthetic Metalworking Fluids. *Environmental Science & Technology* 37, 5278-5288 (2003)).

The largest volume surfactant for aqueous applications such as detergency remains linear alkylbenzene sulfonate (LAS). As depicted in FIG. 1A, LAS chemicals are comprised of a benzene ring connecting polar functionality (e.g. $Na^+SO_3^-$) with branched alkyl chains (eight to fourteen carbons). These surfactants are produced by alkylation of benzene with alpha-olefins such as 1-dodecene; by this method, acid catalysts protonate the olefin leading to double bond migration and various alkyl-benzene isomers such as 2-phenyl to 6-phenyl dodecane (T. Tsai, I. Wang, S. Li, J. Liu, Development of a Green LAB Process: alkylation of benzene with 1-dodecene over mordenite. *Green Chemistry* 5, 404-409 (2003); R. E. Marinangeli, R. J. Lawson, L. B. Galperin, T. R. Fritsch, Process For Producing Arylalkanes And Arylalkane Sulfonates, Compositions Produced Therefrom, And Uses Thereof, U.S. Pat. No. 6,187,981 (2011); A. Jordan, N. Gathergood, Biodegradation of ionic liquids: a critical review. *Chemical Society Reviews*, 44, 8200-8237 (2015); and J. E. Bardach, M. Fujiya, A. Holl, Detergents: Effects on the Chemical Senses of the Fish *Ictalurus natalis* (le Sueur). *Science* 148, 1605-1607 (1965)). The surfactant is then prepared by reacting alkylbenzene precursors with $SO_3$-air or $SO_3$ in sulfuric acid mixtures (D. W. Roberts, Optimisation of the Linear Alkyl Benzene Sulfonation Process for Surfactant Manufacture. *Organic Process Research & Development* 7, 172-184 (2003); published online Epub2003/03/01 (10.1021/op020088w)).

The limited opportunity for tuning the LAS class of surfactants to further enhance its properties has necessitated incorporation of chemical agents such as metal chelants as depicted in FIG. 1A. For example, LAS surfactants in hard water (with $Mg^{2-}$ and $Ca^{2+}$) require additives such as ethylene-diamine-tetraacetic acid (EDTA), which preferentially bind to and suspend hard water ions, preventing the ions from forming inactive precipitates or multilamellar vesicles with surfactants (P. J. Shea, R. T. Duane, Reversal of Cation-Induced Reduction in Glyphosate Activity with EDTA. *Weed Science* 32, 802-806 (1984); and M. Showell, *Handbook of detergents, part D: formulation*. (CRC Press, 2016), vol. 128). Hard water conditions, which often exceed 200 ppm of $Ca^{2+}$ (J. C. Briggs, J. F. Ficke, "Quality of rivers of the United States, 1975 water year; based on the National Stream Quality Accounting Network (NASQAN)," (US Geological Survey, 1977), require co-formulation of chelating agents with surfactants in equal parts (M. Showell, *Handbook of detergents, part D: formulation*. (CRC Press, 2016), vol. 128), increasing cost and complexity. Moreover, incorporation of chelating agents is region and application specific, with many compounds such as EDTA and phosphates banned due to their environmental impact (M. Showell, *Handbook of detergents, part D: formulation*. (CRC Press, 2016), vol. 128; R. S. Boethling, E. Sommer. D. DiFiore, Designing Small Molecules for Biodegradability. *Chemical Reviews* 107, 2207-2227 (2007); and B. Nowak, F. G. Kari, H. G. Krueger, The Remobilization of Metals from Iron Oxides and Sediments by Metal-EDTA Complexes. *Water, Air, & Soil Pollution* 125, 243-257 (2001)). Despite development of a large variety of alternative chelating agents including zeolites (J. M. Newsam, The Zeolite Cage Structure. *Science* 231, 1093-1099 (1986)), citrates, and polycarboxylates (R. S. Boethling, E. Sommer. D. DiFiore, Designing Small Molecules for Biodegradability. *Chemical Reviews* 107, 2207-2227 (2007)), sodium tripolyphosphate remains the standard by which all other chelants are measured (P. J. Shea, R. T. Duane, Reversal of Cation-Induced Reduction in Glyphosate Activity with EDTA. *Weed Science* 32, 802-806 (1984)).

Disclosed herein are methods of forming compounds, including surfactants. Disclosed herein are new methods of forming aromatic and alkyl chain containing compounds that include an acylation step. In some embodiments, a method can include acylating an aromatic containing compound by reacting the aromatic containing compound (discussed further below) with an anhydride containing compound to form an acylated aromatic containing compound.

In some embodiments, methods can include one or more of the following steps, carried out in any order: include acylating an aromatic containing compound by reacting the aromatic containing compound with an anhydride containing compound to form an acylated aromatic containing compound; subjecting an acylated compound to hydrogenation to replace the ketone functionality with an alkyl; functionalizing an acylated aromatic containing compound with a hydrophilic group containing compound; and converting an acylated five membered aromatic ring containing compound to an acylated six membered aromatic ring containing compound (or any increase of the aromatic ring size). In some methods, another step can be carried out at any point in the method: adding an additional side chain to the hydrophobic group, for example via an aldol-condensation. All of these method steps will be discussed below.

One step in illustrative methods of making surfactants includes acylating an aromatic containing compound by reacting the aromatic containing compound with an anhydride containing compound to form an acylated aromatic containing compound. The aromatic containing compound that is being acylated may or may not have previously been subjected to any other steps disclosed herein. Acylating an aromatic containing compound adds an acyl group to the aromatic containing compound to produce an acylated aromatic compound. The compound providing the acyl group can be referred to as the acylating agent. An anhydride, as it includes two acyl groups, can be an effective acylating agent.

The acylating agent, e.g., the anhydride can be added to the aromatic containing compound or in some embodiments, compounds that can be reacted to form an anhydride can be added to an aromatic containing compound (or a mixture containing an aromatic containing compound). For example, a fatty acid could be reacted with a compound in order to form the eventual acylating agent. More specifically, for example, a fatty acid could be reacted with an acyl containing compound, or even more specifically an anhydride to form a long chain (e.g., hydrophobic) containing anhydride. An example of such a reaction can be seen in part B of Scheme 1. In some specific embodiments, a fatty acid could be reacted with an anhydride, for example trifluoroacetic anhydride (TFAA), or acetic anhydride. TFAA may be advantageous because the fluorines contained therein are very electronegative and therefore easily form the desired lauric anhydride (for example). Furthermore, TFAA can be recycled, as shown in part C of Scheme 1. In some embodiments, if for example acetic anhydride is utilized (to react with a fatty acid), a mix of anhydride products would be formed, where some products include two long-chain alkyl groups, some products contain one long chain alkyl group and one acetyl group, and some remain as acetic anhydride.

Scheme 1. Tandem anhydride and acylation of fatty acid over trifluoroacetic anhydride.

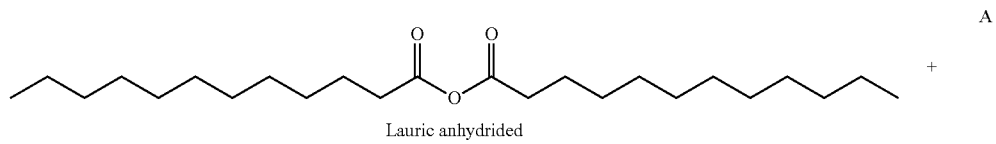

Lauric anhydrided

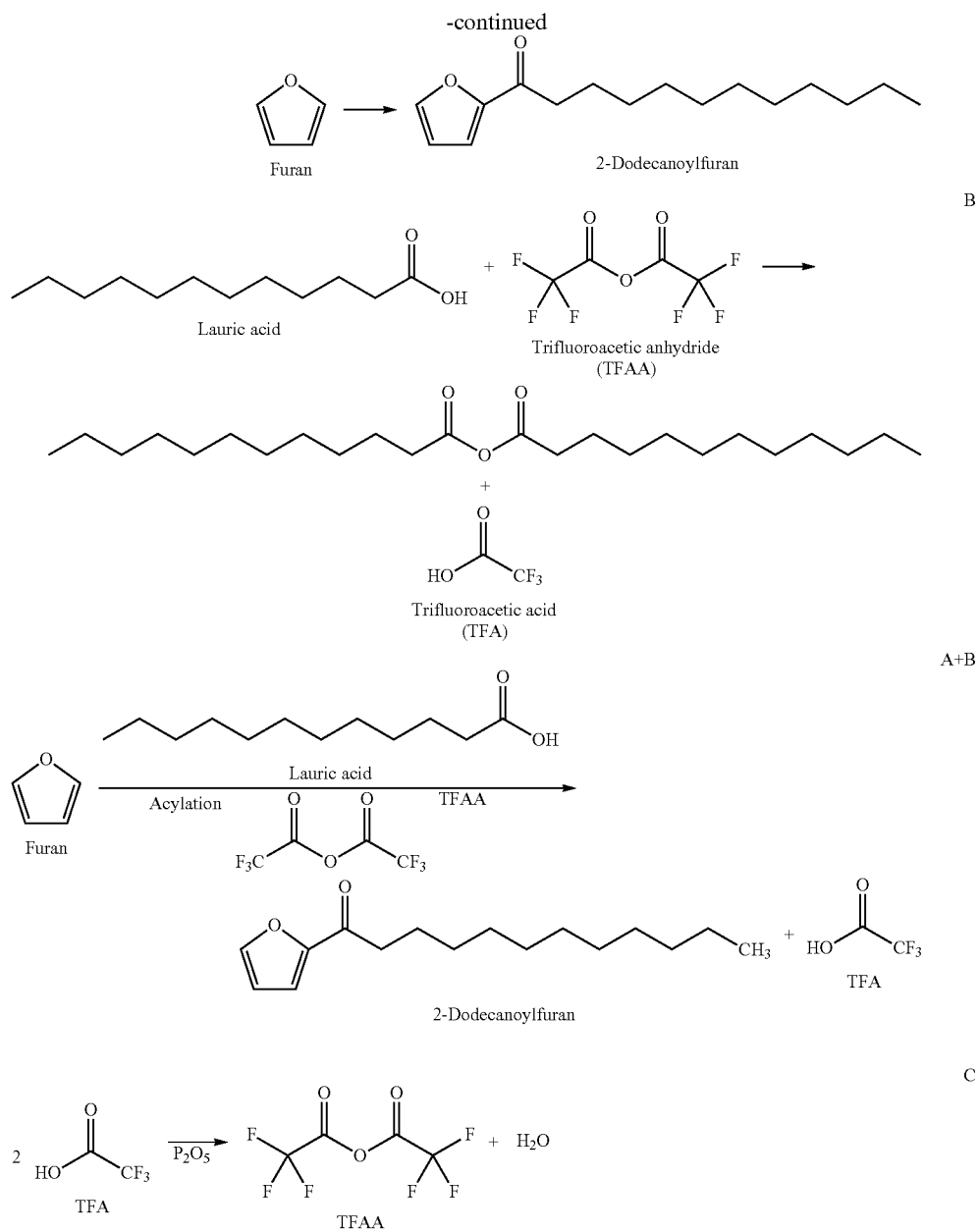

In some advantageous embodiments, the formation of the acylating agent and the reaction of the aromatic containing compound with the acylating agent can occur at substantially the same time, e.g., in the same "pot". This is represented by part A+B in Scheme 1. More specifically, in some embodiments, a single reaction vessel could be utilized to combine the aromatic containing compound, a fatty acid, and an anhydride to "simultaneously" form the acylating agent and acylate the aromatic containing compound.

In some embodiments, an acylating agent can be chosen such that the acylation of the aromatic containing compound with the acylating agent adds an acyl group that contains an alkyl group to the aromatic containing compound. In some embodiments, the alkyl group added via acylation could be a hydrophobic group or could be converted into a hydrophobic group.

Acylating an aromatic containing compound can be undertaken, in some embodiments, by simply combining the acylating agent and the aromatic containing compound. In some embodiments, one or more reaction conditions or reagents can be modified or added respectively. In some embodiments, a catalyst can be utilized and in some embodiments no catalyst is utilized. In some embodiments, the pressure that the reaction is occurring under can be modified, for example it could be increased from atmospheric pressure. The pressure that the acylation reaction can be carried out at can be from 0 to 3000 psi, for example. In some embodiments, the temperature that the acylation reaction is occurring at can be modified, for example, it could be increased from room temperature. The temperature that the acylation reaction can be carried out at can be from 0° to 700° C., for example. The reaction can be carried out heterogeneously or homogeneously in the gas, liquid, or solid phases or any combination of phases or supercritical conditions.

The acylation reaction can optionally be carried out with use of a catalyst. Table 1 provides illustrative potential catalyst species that can be used.

TABLE 1

Potential catalyst classes and types which can be used in all four chemical reactions presented.

| Family | Genus | Species | Example |
|---|---|---|---|
| Acid | Lewis Acid (L-Acid) Catalysts | L-Acid | $AlCl_3$, $TiCl_4$, $FeCl_3$, $BF_3$, $SnCl_4$, $ZnCl_2$, $ZnBr_2$, Amberlyst-15 |
|  |  | Supported L-Acid L-Acid/S | $SiO_2$, $Al_2O_3$, $ZrO_2$, $TiO_2$, $SiO_2$—$Al_2O_3$ |
|  | BrØnsted Acid (B-Acid) Catalysts | B-Acid | HCl, HBr, HI, $HClO_4$, $HClO_3$, $HNO_3$, $H_2SO_4$, $CH_3COOH$, $CF_3COOH$, $H_3PO_4$ |
|  | Solid Acid Catalysts | Zeolites, (Z) | H—ZSM-5, H—BEA, H—Y, Mordenite, Ferrierite |
|  |  | Substituted-Zeolites (Sub.) | Sn, Ge, Ti, Fe, Zr |
|  |  | Heteropolyacids (HPAs) | $H_3PW_{12}O_{40}$, $H_3SiW_{12}O_{40}$, $H_3PMo_{12}O_{40}$, $H_3SiMo_{12}O_{40}$ ($Cs^+$ substituted HPAs) |
|  |  | Phosphate ($PO4^{3-}$) | Niobium phosphate ($NbOPO_4$), Zirconium phosphate ($ZrO_2$—$PO_4$), Siliconiobium phosphate (Nb-P-Si-O) |
|  |  | Zirconia (ZrO2) | $SO_3$-$ZrO_2$, $SiO_2$-$ZrO_2$, Zeolites-$ZrO_2$, $Al_2O_3$-$ZrO_2$, $WO_x$-$ZrO_2$ |
|  |  | Carbon (C) | Sulfated carbon ($SO_3$H-functionalized carbon) |
| Base | Solid Base Catalysts | Supported Alkalis | $KF/Al_2O_3$, $K_2CO_3/Al_2O_3$, $KNH_2/Al_2O_3$, $NaOH/Al_2O_3$, $KOH/Al_2O_3$ |
|  |  | Zeolites, Clays | K, Rb, Cs-exchanged X-zeolites, ETS-10, Sepiolite, |
|  |  | Phosphates | Hydroxyapatite, natural phosphates |
|  |  | Amides, imines, amines, or ammonium ions on support | $KNH2/Al2O3$, K, Y, Eu supported on zeolites |
|  |  | Metal Oxide, Mixed Metal Oxide | MgO, CaO, Mg—Zr—O, Mg—Si—O, Mg—Al—O |
|  | Homogeneous Base | Organic & Inorganic | pyridine, imidazole, ammonia |
| Metal | Metallic | Precious metals, alkali or alkaline earth metals | Pt, Pd, Ni, Cu, Al, Zn, Au, Ag, Sn |
|  | Bimetallic | Transition-Transition or Precious-Transition metals | Pd—Cu, Cu—Ni, Cu—Cr, Ni—Pt, Ni—Pd, Ni—Sn |
|  | Metal Oxide | Metal oxides, Rare earth oxides, Alkali metal oxides | NiO, $ZnO_2$, CuO, Cu—Cr—O, Cu—Ni—O, Cu—Al—O, $Al_2O_3$, $ZrO_2$, $La_2O_3$ |

Disclosed methods can also include an optional step of subjecting an acylated compound to hydrogenation. Acylation of the aromatic containing compound will necessarily introduce a ketone adjacent the aromatic ring. Hydrogenation serves to replace the ketone functionality with a methylene.

Any method of hydrogenation, e.g., replacing a ketone with an alkyl can be utilized in illustrative methods of making surfactants. In some embodiments, the acylated aromatic containing compound can be reacted with hydrogen ($H_2$) gas. In some embodiments, one or more reaction conditions or reagents can be modified or added respectively. In some embodiments, a catalyst can be utilized and in some embodiments no catalyst is utilized. Any of the illustrated catalysts presented above in Table 1, or others can optionally be utilized in the hydrogenation reaction. In some embodiments, the pressure that the reaction is occurring under can be modified, for example it could be increased from atmospheric pressure. The pressure that the hydrogenation reaction can be carried out at can be from 0 to 3000 psi, for example. In some embodiments, the temperature that the hydrogenation reaction is occurring at can be modified, for example, it could be increased from room temperature. The temperature that the hydrogenation reaction can be carried out at can be from 0° to 700° C., for example. The reaction can be carried out heterogeneously or homogeneously in the gas, liquid, or solid phases or any combination of phases or supercritical conditions.

Methods of making surfactants can also include an optional step of functionalizing an acylated aromatic containing compound with a hydrophilic moiety containing compound. It should also be noted that illustrative methods of making surfactants could include functionalizing an aromatic containing compound before it is acylated.

In some embodiments, the hydrophilic moiety can be chosen to produce a desired final compound. For example, the choice of hydrophilic moiety can determine if an ionic, anionic, cationic or otherwise surfactant is being synthesized. If an ionic (anionic and cationic) surfactant is being synthesized, the hydrophilic moiety can include a surface active ion and a counter metal ion which can include but are not limited to those discussed below. If nonionic surfactants are being synthesized, the hydrophilic moiety can include but are not limited to those discussed below. If a zwitterionic surfactant is being synthesized, the hydrophilic moiety can include zwitterionic groups. Zwitterionic groups typically include a cationic group, for example a primary, secondary, or tertiary amine or quaternary ammonium ion attached to an anionic group as discussed below.

In some embodiments, the hydrophilic moiety added can include, for example an anionic moiety, for example a sulfonate or a phosphate; a cationic moiety, for example a quaternary ammonium compound; a nonionic moiety, for example an alcohol or an ethoxylate; or an amphoteric moiety, for example an imidazoline or beatine.

Any method of functionalizing the acylated aromatic compound with a hydrophilic moiety containing compound or portion of a compound can be utilized herein. In some embodiments, sulfonation or phosphonation, can be utilized, for example. In some embodiments, one or more reaction conditions or reagents can be modified or added respectively. In some embodiments, a catalyst can be utilized and in some embodiments no catalyst is utilized. Any of the illustrated catalysts presented above in Table 1 above, or others can optionally be utilized in to functionalize the acylated compound with the hydrophilic moiety. In some embodiments, the pressure that the reaction is occurring under can be modified, for example it could be increased from atmospheric pressure. The pressure that the functionalization reaction can be carried out at can be from 0 to 3000 psi, for example. In some embodiments, the temperature that the reaction is occurring at can be modified, for example, it could be increased from room temperature. The temperature that the functionalization reaction can be carried out at can be from 0° to 700° C., for example. The reaction can be carried out heterogeneously or homogeneously in the gas, liquid, or solid phases or any combination of phases or supercritical conditions.

Illustrative methods of making surfactants can also include an optional step of cycloaddition. An illustrative cycloaddition reaction is the Diels-Alder reaction. For example, this step can convert an acylated five membered aromatic ring containing compound to an acylated six membered aromatic ring containing compound (or any increase of the aromatic ring size). Any method of cycloaddition, e.g., increasing the ring size of an aromatic group, can be utilized in illustrative methods of making surfactants. In some embodiments, the acylated aromatic containing compound can be reacted with ethylene ($C_2H_4$), propylene ($C_3H_6$), acrolein ($C_3H_4O$), or acrylic acid ($C_3H_4O_2$). In some embodiments, one or more reaction conditions or reagents can be modified or added respectively. In some embodiments, a catalyst can be utilized and in some embodiments no catalyst is utilized. Any of the illustrated catalysts presented above in Table 1, or others can optionally be utilized in the cycloaddition reaction. In some embodiments, the pressure that the reaction is occurring under can be modified, for example it could be increased from atmospheric pressure. The pressure that the cycloaddition reaction can be carried out at can be from 0 to 3000 psi, for example. In some embodiments, the temperature that the reaction is occurring at can be modified, for example, it could be increased from room temperature. The temperature that the cycloaddition reaction can be carried out at can be from 0° to 700° C., for example. The reaction can be carried out heterogeneously or homogeneously in the gas, liquid, or solid phases or any combination of phases or supercritical conditions.

In embodiments where the step of acylating the aromatic group containing compound has been carried out in order to, for example attach a hydrophobic group to the aromatic containing compound, another optional step can be undertaken. This optional step includes adding an alkyl chain (e.g., an alkyl chain having from 1 to 10 carbon atoms, in some embodiments from 1 to 6 carbon atoms) to the existing hydrophobic group. Any reaction that can add an alkyl chain to the existing hydrophobic group can be utilized. One such method that can be utilized can include, for example an aldol condensation reaction. An aldol condensation reaction can be utilized to add an alkyl chain to the existing hydrophobic chain if the optional hydrogenation reaction has not yet been carried out because the aldol-condensation reaction utilizes the ketone to add the alkyl chain to that carbon atom.

In some embodiments, one or more reaction conditions or reagents can be modified or added respectively. In some embodiments, a catalyst can be utilized and in some embodiments no catalyst is utilized. Any of the illustrated catalysts presented above in Table 1, or others can optionally be utilized to add an alkyl chain to the hydrophobic moiety. In some embodiments, the pressure that the reaction is occurring under can be modified, for example it could be increased from atmospheric pressure. The pressure that the reaction can be carried out at can be from 0 to 3000 psi, for example. In some embodiments, the temperature that the reaction is occurring at can be modified, for example, it could be increased from room temperature. The temperature that the reaction can be carried out at can be from 0° to 700° C., for example. The reaction can be carried out heterogeneously or homogeneously in the gas, liquid, or solid phases or any combination of phases or supercritical conditions.

Illustrative methods of making surfactants can be utilized to make compounds that can be used in a number of different applications, including as an illustrative and non-limiting example, surfactants. In some embodiments, such methods can include acylating an aromatic containing compound by reacting the aromatic containing compound with an anhydride containing compound to form an acylated aromatic containing compound; and functionalizing an acylated aromatic containing compound with a hydrophilic group containing compound. In some embodiments, such methods can optionally include a step of subjecting the acylated compound to hydrogenation to replace the ketone functionality with an methylene. In some embodiments, such methods can optionally include adding an additional side chain to the hydrophobic group, for example via an aldol-condensation before an optional step of hydrogenation to replace the ketone group with a methylene group.

In some embodiments, the step of acylating the aromatic containing compound can occur first, before any other steps. In some embodiments, the step of functionalizing the acylated compound with a hydrophilic group can occur immediately after the acylation step or after any other intermediate steps. In some embodiments, the step of subjecting the acylated compound to hydrogenation to replace the ketone functionality with a methylene functionality can occur before the compound is functionalized with a hydrophilic moiety. In some embodiments, the step of subjecting the acylated compound to hydrogenation can occur after an additional side chain has been added to the hydrophobic group, so that the additional side chain can be added with an aldol-condensation reaction.

Another disclosed method that could be utilized to make illustrative compounds could include acylating an aromatic containing compound by reacting the aromatic containing compound with an anhydride containing compound to form an acylated aromatic containing compound; converting the acylated aromatic ring containing compound to an acylated aromatic ring containing compound that includes at least one more carbon atom in the ring; and functionalizing the acylated aromatic containing compound with a hydrophilic group containing compound. The cycloaddition and the functionalization step can be carried out in any order after the acylation step. In some such embodiments, illustrative methods of making surfactants can also include an optional step of hydrogenation to replace the ketone on the hydrophobic moiety added via acylation with a methylene group. Optionally, an alkyl side chain can be added to the hydrophobic group, either before the optional hydrogenation (via an aldol-condensation reaction for example) or via some other reaction (either before or after the optional hydrogenation reaction).

Disclosed herein are surfactants which include an aromatic moiety, a hydrophilic moiety and a hydrophobic moiety. In some embodiments the hydrophilic group can be anionic, cationic, nonionic, or zwitterionic and the hydrophobic group can be a linear or branched, saturated, or unsaturated hydrocarbon chain.

In some embodiments, disclosed surfactants can be represented by Formula 1:

(I)

where A is an aromatic moiety, H is a hydrophobic group having about 3 to about 26 carbon atoms consisting of linear, branched, saturated, or unsaturated hydrocarbon chains and K is a hydrophilic group. Each of the portions of disclosed surfactants are discussed in greater detail in an illustrative fashion below.

The functional group defined as 'H' in Formula 1 denotes a hydrophobic group, which may include a carbon containing chain, which may be saturated or unsaturated and may be with or without branching. The hydrophobic group may optionally contain any number of oxygen, nitrogen, sulfur, or other heteroatoms. Illustrative hydrophobic groups can include linear alkyl chains having about 3 to about 26 carbons, or alkyl chains containing about 3 to about 26 carbons with some degree of branching (e.g. ethyl or propyl groups). In some embodiments, illustrative hydrophobic groups include at least some degree of branching that includes at least two carbons (e.g., an ethyl group or larger group). Illustrative non-carbon functional groups that may also be optionally included can include hydroxyls, carbonyls, ethers, and esters, for example.

The functional group defined as "K" in Formula 1 denotes a hydrophilic group. In some embodiments the hydrophilic group can be anionic, cationic, nonionic, or zwitterionic.

In the case of ionic (anionic and cationic) surfactants, K can include a surface active ion and a counter metal ion which can include but are not limited to the following possibilities, listed in Table 2 below.

TABLE 2

Illustrative ionic moieties that can be included in the hydrophilic portion, "K" in Formula 1.

| Ionic Moieties | | | |
|---|---|---|---|
| Anionic | | Cationic | |
| Sulfate | R—O—S(=O)(=O)—O⁻ | Amines & Ammonium salts | R'—N⁺(R'')(R''')—R |
| Sulfonate | R—S(=O)(=O)—O⁻ | Polyammonium | [R—N⁺(R''')(R')—N⁺(R'')(R''')—R''']ₙ |
| Sulfinate | R—S(=O)—O⁻ | Hydroxyammonium | R—N⁺(OH)(R')—R'' |
| Thiosulfate | R—O—S(=O)(=S)—O⁻ | Pyridinium | pyridinium-R |
| Sulfamidate | R—N(H)—S(=O)(=O)—O⁻ | Picolinium | R'-picolinium-R |
| Carboxylate | R—C(=O)—O⁻ | Imidazolinium | imidazolinium R, R', R'' |

TABLE 2-continued

Illustrative ionic moieties that can be included in the hydrophilic portion, "K" in Formula 1.

| Sarcosinate & Taurate | R—H—R—C(=O)O⁻, R | Benz-imidazolinium | [benzimidazolinium structure with R, R', R''] |
| --- | --- | --- | --- |
| Phosphate | R—O—P(=O)(O⁻)—O⁻ or R—O—P(=O)(O⁻)—O—R' | Oxonium | R—O⁺(R')—R'' |
| Pyrophosphate | R—O—P(=O)(O⁻)—O—P(=O)(O⁻)—O—R' | Sulfonium | R—S⁺(R')—R'' |
| Phosphonate | R—P(=O)(O⁻)(R') or R—P(=O)(O⁻)—O⁻ | Phosphonium | R—P⁺(R')(R'')(R''') |

Counter-ion

| Na⁺, K⁺, Li⁺, Ca²⁺, Mg²⁺, NH₄⁺, amines | Cl⁻, Br⁻, NO₃⁻, SO₄²⁻, PO₄³⁻, HPO₄²⁻, H₂PO₄⁻, CH₃OSO₃⁻, HCO₂⁻, CH₃CO₂ |
| --- | --- |

In the ionic moieties in Table 2, R can denote either the point of attachment of the ion to the aromatic group (A) in Formula 1 or a hydrocarbon chain, with or without oxygen atoms or other heteroatoms (e.g. —$(CH_2)_n$—, —$(CH_2CH_2O)_n$—, —$(CH_2CH_2CH_2O)_n$—, etc.), attached to the aromatic moiety wherein n can be from about 1 to about 20. R', R'', and R''' can represent either a hydrogen atom or a hydrocarbon chain with a carbon number between about 1 and about 10 and X denotes a heteroatom.

Non-ionic groups can include but are not limited to the following possibilities listed in Table 3:

TABLE 3

Illustrative non-ionic moieties that can be included in the hydrophilic portion, "K" in Formula 1.

Non-ionic moieties

| Polyethoxylate | R—(OCH₂CH₂)ₙ—OR |
| --- | --- |
| Poly(Oxyethylene-co-Oxypropylene) | 1  R—(OCH₂CH₂)ₘ—(OCH(CH₃)CH₂)ₙ—(OCH₂CH₂)ₘ—OH |
|  | 2  R—(OCH(CH₃)CH₂)ₙ—(OCH₂CH₂)ₘ—(OCH(CH₃)CH₂)ₙ—OH |
| 1,4-Sorbitan derivatives | [sorbitan structure with OR groups] |
| Isosorbide derivatives | [isosorbide structure with OR groups] |

TABLE 3-continued

Illustrative non-ionic moieties that can be included in the hydrophilic portion, "K" in Formula 1.

| Non-ionic moieties | |
| --- | --- |
| Polyglycoside | ![structure] |
| Hydroxyl, methoxy, carboxyl, or akanal groups | ![structures] |

In the non-ionic moieties in Table 3, R can denote either the point of attachment to the aromatic group (A) in Formula 1 or a primary, secondary or tertiary amide, an ester, a hydrocarbon chain, or a hydrogen atom; n and m can independently be between about 1 and about 40 in ethoxylates and x can be between about 1 and about 5 in polyglycosides.

Zwitterionic groups include a cationic group usually consisting of a primary, secondary, or tertiary amine or quarternary ammonium ions attached to an anionic group listed in Table 3.

The functional group defined as "A" in Formula 1 represents an aromatic moiety. In some embodiments, A can represent a furan moiety. Furan is a five-membered aromatic heterocycle that can be produced from the decarbonylation of furfural. Furfural is a biomass-derived chemical, which can be produced from the acid-catalyzed dehydration of xylose, a hydrolysis product from the hemicellulosic component of biomass. Lauric acid is an illustrative saturated fatty acid, which can be produced via the hydrolysis of biomass-derived triglycerides such as palm-kernel oil and coconut oil.

In some embodiments, the aromatic moiety can include furan that is functionalized at one or more locations. Examples of such illustrative furan containing aromatic moieties can start from or include furan carboxylic acid (FCA), furan dicarboxylic acid (FDCA), furfural, hydroxymethylfurfural (HMF), methylfuran, and dimethylfuran, for example. Reaction of the aromatic group via acylation or other functionalization can occur at any location on the aromatic ring. In the case of a di-substituted aromatic furan ring, such as furan dicarboxylic acid (FDCA) in which the 2 and 5 positions are substituted by carboxylic acids, acylation with a hydrophobic group and/or functionalization with a hydrophilic group can be performed in the 3 or 4 position.

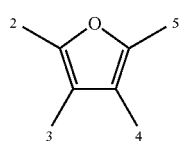

An illustrative list of possible aromatic groups (A) can include but is not limited to the following possibilities, listed in Table 4.

TABLE 4

Possible aromatic moieties of the surfactant in Formula 1.

| Aromatic moieties | |
| --- | --- |
| Furan | ![furan structure with $R^1$, $R^2$, $R^3$, $R^4$] |
| Thiophene | ![thiophene structure with $R^1$, $R^2$, $R^3$, $R^4$] |
| Pyrrole | ![pyrrole structure with $R^1$, $R^2$, $R^3$, $R^4$, $R^5$] |
| Imidazole | ![imidazole structure with $R^1$, $R^2$, $R^3$, $R^4$] |
| Benzene | ![benzene structure with $R^1$, $R^2$, $R^3$, $R^4$, $R^5$, $R^6$] |
| Pyridine | ![pyridine structure with $R^1$, $R^2$, $R^3$, $R^4$, $R^5$] |

TABLE 4-continued

Possible aromatic moieties of the surfactant in Formula 1.
Aromatic moieties

| Naphthalene | 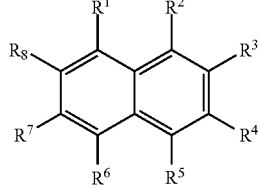 |
| --- | --- |
| Tetrahydronaphthalene | 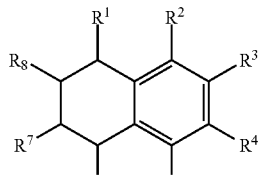 |

In Table 4 $R^n$ (n=1-8) can either denote the point of attachment of the hydrophobic chain of the surfactant (H), the hydrophilic group (K), a hydrocarbon chain with carbon number between about 1 and about 10 between the aromatic group (A) and K, or a hydrogen atom. Specific examples of surfactants with alternative aromatic functionality are outlined in Table 4.

In some illustrative embodiments, aromatic moieties in Formula 1 can include thiophene, pyrrole, imidazole, and pyridine.

Table 5 below offers some illustrative examples of surfactants that may not be included in the instant disclosure.

TABLE 5

Variable Aromatic Surfactants

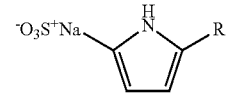

In the embodiments depicted in Table 5, the hydrophobic functionality (R) is generally a saturated alkyl chain from about 3 to about 26 carbons in length; in some embodiments a linear chain having from about 8 to about 14 carbons. In some embodiments, the surfactants illustrated in Table 5 are not disclosed herein.

Also disclosed herein are more specific classes of the surfactants of Formula 1.

Ketone-Based and Hydroxyl-Based Furan Surfactant

This specific subset of disclosed surfactants of Formula 1 include a ketone functional group on the alkyl chain directly adjacent to the aromatic group. Synthesis of a molecule via acylation of an aromatic-containing group (e.g. furan, thiophene, pyrrole, etc.) with the anhydrous product of two carboxyl-containing groups (e.g. fatty acid, such as lauric acid) can form a combined molecule with a ketone functional group in the alpha-carbon position of the aromatic functional group, as shown in the general structure depicted in Formula 2,

Formula 2 wherein the ketone functional group is directly adjacent to an aromatic group (A) as well as a hydrophobic chain (R), as defined above for H in Formula 1. Optionally, subsequent functionalization of the aromatic-containing group with a hydrophilic functional group (K), as defined above can form a surfactant molecule with an anionic, cationic, zwitterionic, or nonionic functional group according to the structure in Formula 3.

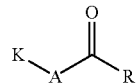

Formula 3

Examples of this ketone-based composition are illustrated in Table 6 below, but are not limited to the specific structures noted.

TABLE 6

Illustrative examples of ketone-based surfactant containing a carbonyl directly adjacent to the aromatic functional group.
Ketone Surfactants

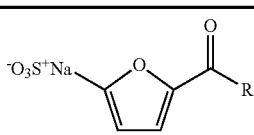

Another possible iteration of the surfactants described herein is the selective reduction of the ketone functionality to a hydroxyl, according to Formula 4.

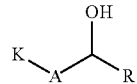

Formula 4 wherein the hydroxyl functional group is directly adjacent to an aromatic group (A) as well as a hydrophobic chain (R), as defined above. Illustrative examples of hydroxyl-based compounds are listed in Table 7, but not limited to those illustrated.

TABLE 7

Illustrative examples of hydroxyl-based surfactant containing a hydroxyl group directly adjacent to the aromatic functional group.
Hydroxyl Surfactants

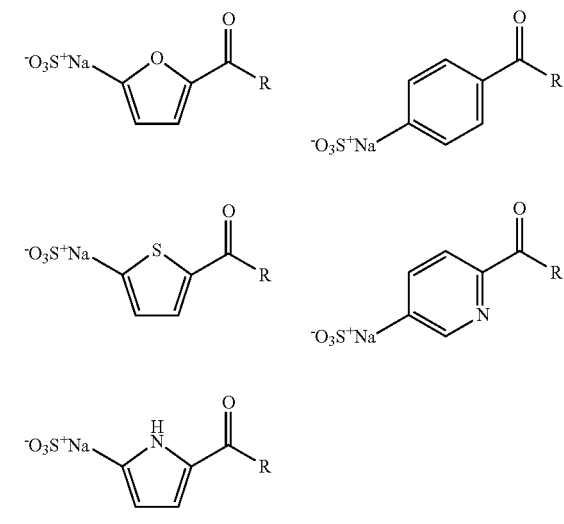

TABLE 8

Illustrative examples of etherified surfactant.
Etherified Surfactant

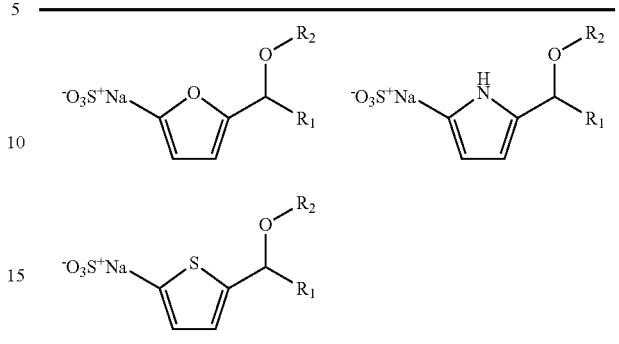

Etherified Surfactant

This specific subset of disclosed surfactants of Formula 1 include a specific structure definition of a side chain connected to the alpha-carbon adjacent to the aromatic functional group via an ether linkage. As such, the branched hydrophobic portion of the surfactant includes a long alkyl chain, which provides hydrophobicity, as well as a shorter side chain connected via an ether linkage, which may improve the cold-water performance of the surfactant (J. G. Ma, B. J. Boyd, C. J. Drummond, Positional isomers of linear sodium dodecyl benzene sulfonate: Solubility, self-assembly, and air/water interfacial activity. *Langmuir* 22, 8646-8654 (2006)). Attachment of the side chain via an ether linkage may have an additional benefit of improved biodegradability, as the ether bond may be more easily broken than a direct carbon-carbon bond.

The general structure of the etherified surfactant is shown in Formula 5,

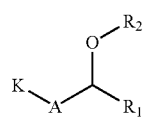

Formula 5 wherein the ether group is directly connected to the alpha-carbon adjacent to the aromatic group (A), which is connected to the hydrophilic functional group (K). $R_1$ and $R_2$ are alkyl chains are as defined above. In some embodiments, $R_1$ can have from about 3 to about 26 carbons, or in some embodiments from about 10 to about 12 carbons. In some embodiments, $R_2$ can have from about 1 to about 26 carbons, or in some embodiments from about 2 to about 4 carbons.

Some illustrative examples of an etherified surfactant are shown in Table 8.

Gemini Surfactant

This specific subset of disclosed surfactants of Formula 1 includes two furan-based surfactant molecules are joined together via a linkage between the alpha carbons directly adjacent to the aromatic group. Gemini surfactants have been shown to have improved surfactant properties, such as a critical micelle concentration as much as one order of magnitude lower than conventional surfactants. The general structure of a disclosed Gemini surfactant is shown in Formula 6,

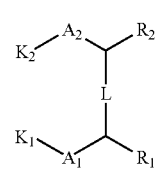

Formula 6 in which two structures containing a hydrophilic (K), hydrophobic (R), and aromatic (A) functionalities are connected via a carbon-based linker (L). Definitions for K, R, and A are given above, where the structure of each subscripted functional group (e.g. $K_1$ & $K_2$) may differ, thereby forming an asymmetric Gemini surfactant. The linking group (L) may include a carbon chain that can be saturated or unsaturated; can contain any number of oxygen, nitrogen, or sulfur containing functional groups, such as ethers, esters, ethoxy groups, and propoxy groups, or amines, amides, sulfates, or sulfides for example; or any combination thereof.

An illustrative example of such a Gemini surfactant incorporates a linking molecule (L) with two ether groups directly connected to the alpha-carbon adjacent to the aromatic group, which are connected via an alkyl chain of about 1 to about 20 carbons in length, or from about to about 6 carbons. An illustrative example of a potential embodiment of a Gemini surfactant is shown in Formula 7.

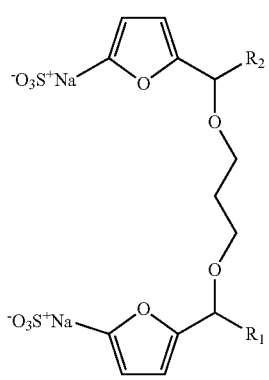

Formula 7

Alternate routes for synthesis of a Gemini surfactant can include coupling of the aromatic rings, such as furan, via acylation steps, as is shown Scheme 1. The resulting surfactant could be nonionic (as shown) or ionic, such as a sulfate, sulfonate, or other ionic moiety as listed above.

Scheme 2. Illustrative example of a synthesis of a Gemini surfactant to form a nonionic structure.

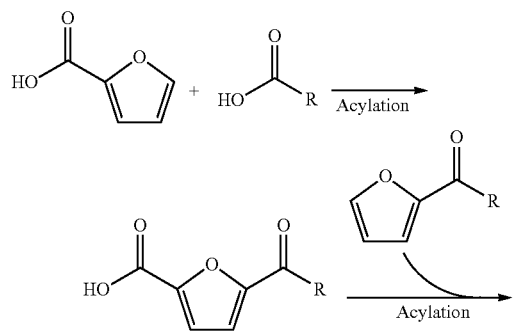

Side-Chain Aromatic Surfactant

This specific subset of disclosed surfactants of Formula 1 includes an aromatic moiety connected to a hydrophobic chain, in which the hydrophilic portion of the surfactant is attached to the alpha-carbon directly adjacent to the aromatic ring. The resulting surfactant contains the aromatic functionality as a side-chain branch, according to Formula 8,

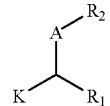

Formula 8 in which the hydrophilic moiety (K), hydrophobic moiety ($R_1$), and aromatic group (A) are each attached to the same carbon. An optional side-chain ($R_2$) attached to the aromatic moiety may include a carbon chain which may be saturated or unsaturated; may contain any number of oxygen, nitrogen, or sulfur containing functional groups, such as ethers, esters, ethoxy groups, and propoxy groups, for example; or any combination thereof.

Illustrative examples of such surfactants include a furan, thiophene, or pyrrole aromatic group with a sulfate hydrophilic group as illustrated in Table 9.

TABLE 9

Illustrative side-chain aromatic surfactants.
Side-Chain Aromatic Surfactant

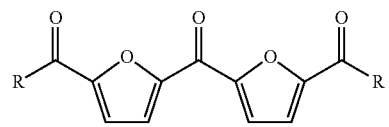

Ethoxylated Surfactant

This specific subset of disclosed surfactants of Formula 1 includes ethoxylated aromatic-based surfactants. In these embodiments, a hydrophobic chain (R) connects to the aromatic moiety (A), which connects to a straight chain of any number of ethylene oxide or propylene oxide units or combination thereof terminated by a hydroxyl or alkoxy group, examples of which are shown in Table 10.

TABLE 10

Illustrative ethoxylated or propoxylated aromatic surfactants.
Ethoxylated Aromatic Surfactant

TABLE 10-continued

Illustrative ethoxylated or propoxylated aromatic surfactants.
Ethoxylated Aromatic Surfactant In some embodiments, such surfactants include a furan aromatic moiety, with a hydrophobic chain including from about 3 to about 26 carbons (branched or linear), and a hydrophilic portion including from about 1 to about 60 ethylene oxide units, propylene oxide units, or combinations thereof. In some embodiments, such surfactants can include a furan aromatic ring, with a hydrophobic alkyl moiety including from about 9 to about 12 carbon atoms, and a hydrophilic moiety including from about 1 to about 20 ethylene oxide units terminated by a hydroxyl or alkoxy group.

Ring-Opened Furan Surfactant

This specific subset of disclosed surfactants of Formula 1 includes structures resulting from the acylation of a furan-based aromatic ring with a hydrophobic chain, ring-opening of furan, and functionalization of resulting hydroxyl groups, as is shown in Scheme 3.

Scheme 3. Acylation of a furan-containing moiety with a hydrophobic group and subsequent reduction of all oxygen groups to hydroxyl groups, which can be further functionalized.

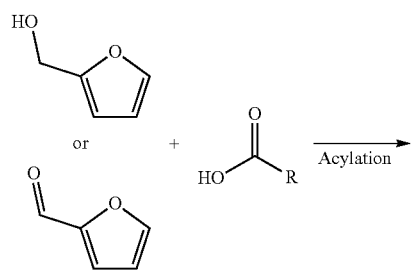

The general structure of the ring-opened furan surfactant, shown on the right in Scheme 2 contains an acylated $R_1$ hydrophobic group, which is defined above, and four $R_2$ groups, which could represent an alkyl chain (saturated or unsaturated, with or without oxygen functionality) or a hydrogen, or any combination thereof. Any one of the $R_2$ moieties could also contain ionic hydrophilic groups, such as a sulfate or sulfonate.

Illustrative examples of such surfactants includes $R_1$ that are alkyl chains having from about 3 to about 26 carbons and each $R_2$ as either a methyl group or a hydrogen atom, as shown in Table 11.

TABLE 1

Illustrative examples of ring-opened surfactants.
Ring-Opened Surfactant

Additional iterations of this surfactant could use alternative aromatic rings such as furan, furan carboxylic acid (FCA), furan dicarboxylic acid (FDCA), furfural, hydroxymethylfurfural (HMF), methylfuran, pyrrole, or thiophene as a starting reactant for example.

An additional option for synthesis of ring opened surfactants includes the acylation of multiple furan rings into a chain in addition to the hydrophobic group. With subsequent reduction and ring opening, a longer version of the surfactant shown in Table 11 can be formed, as is described in Scheme 4. Multiple furan-furan coupling acylation steps could be performed via acylation of furfuryl alcohol with furan carboxylic acid and subsequent acylation with a fatty acid.

Scheme 4. An additional option for synthesis of ring opened surfactants.

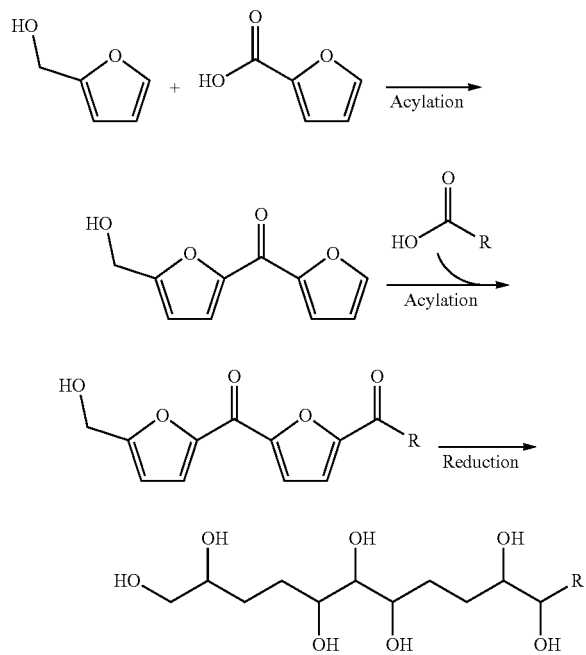

Continued furan-coupling acylation and ring opening could then be used to form a surfactant with the general structure in which the quantity of oxygen functional groups is controlled by the degree of furan acylation, as shown in Formula 9.

Formula 9

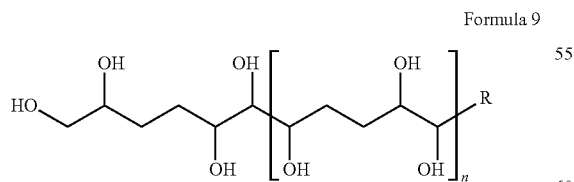

Diels-Alder Cyclo-Adduct Surfactant

This specific subset of disclosed surfactants of Formula 1 includes structures resulting from the reaction of an acylated furan aromatic with maleic anhydride via Diels-Alder cycloaddition, shown in Scheme 5.

Scheme 5. Acylation of a furan-based aromatic structure and subsequent Diels-Alder cycloaddition with maleic anhydride forms a bicyclic surfactant structure.

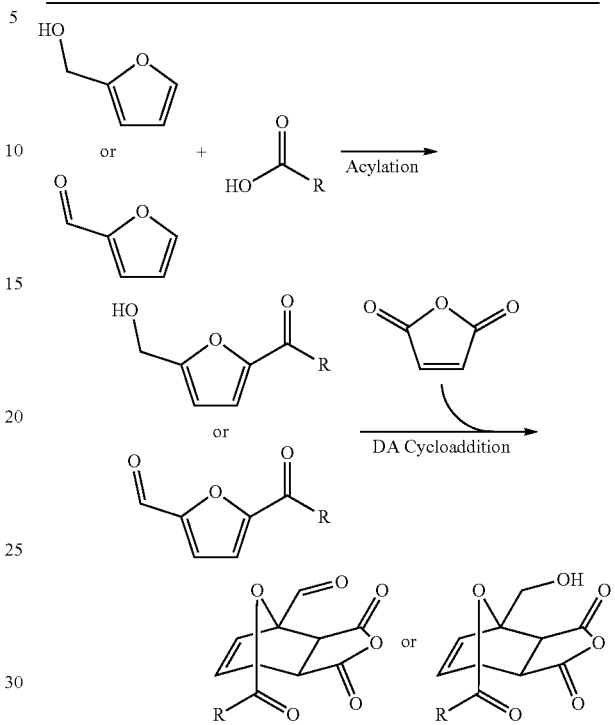

The resulting bi-cyclic aromatic surfactant has a nonionic, bicyclic hydrophilic head and a hydrophobic tail (R), which is defined above. Additional iterations of this surfactant could use furan, furan carboxylic acid (FCA), methylfuran, pyrrole, or thiophene for example as a starting reactant instead of the furfuryl alcohol or furfural shown in Scheme 5.

Di-Substituted, Acylated Furan Surfactant

This specific subset of disclosed surfactants of Formula 1 can be derived from a furan aromatic ring which is functionalized in the 2 or 5 position, such as hydroxymethylfurfural (HMF), dimethylfuran (DMF), or furan dicarboxylic acid (FDCA). In this case, acylation occurs in the 3 or 4 position of the furan aromatic ring. The general surfactant structure is shown in Formula 10.

Formula 10

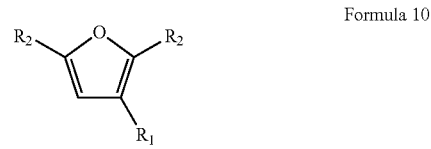

wherein $R_1$ is the hydrophobic moiety of the surfactant, described above, and each $R_2$ is a functional group resulting from the starting material. For example, in the case of FDCA, each $R_2$ corresponds to a carbonyl. Resulting surfactant molecules could be further functionalized to attach an ionic hydrophilic moiety such as a sulfate. Illustrative examples of such surfactant structures are shown in Table 12.

TABLE 2

Illustrative examples of potential di-substituted surfactants, which are acylated in the 3 or 4 position to attach a hydrophobic moiety.
Di-Substituted, Acylated Surfactant

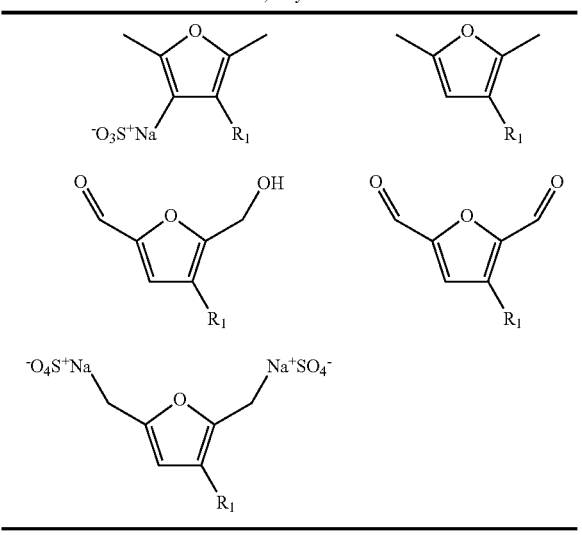

As discussed above, disclosed methods can utilize a selective furan acylation reaction as an alternative to benzene alkylation, for example. Acylation of a furan (as an example only) can be utilized to bond a selected hydrophobic moiety to a furan molecule, which can then be subsequently functionalized with a hydrophilic moiety to form a molecule that can function as a surfactant. Optionally, the acylated furan molecule can be transformed into linear alkylbenzene (LAB) or modified linear alkylbenzene (MLAB) via diels-alder cycloaddition using ethylene gas, for example. The product from the cycloaddition reaction can optionally be subsequently functionalized with a hydrophilic moiety to form a biorenewable drop-in replacement for current methods of LAS or MLAS production.

Acylation reactions contemplated in disclosed methods may be advantageous over alkylation, because acylated aromatic products do not easily isomerize or continue to acylate (e.g. multiple bonding of alkyl chains to an aromatic ring). Conversely, alkylated benzene molecules tend to isomerize, forming products with alkyl branches with variable length, thereby reducing selectivity toward desired products. Additionally, aromatics with terminal linear alkyl substituents can be made by acylation, a product that cannot be produced via alkylation (J. Clayden, N. Greeves, S. Warren, Organic Chemistry 2nd Ed., Electrophilic aromatic substitution, Oxford, N.Y., 2012, pp. 493-494). An existing technology which also forms a furan aromatic as part of the surfactant, as developed by Procter & Gamble, utilizes a less-selective and more costly Grignard reaction instead of acylation in order to combine an aromatic furan, such as furfural, with a hydrophobic alkyl chain (United States Patent Pub. No. 2015/0150768, the disclosure of which is incorporated herein by reference thereto).

In some embodiments, furan acylation with lauric acid can be performed by aid of trifluoroacetic anhydride (TFAA), which is an acylating agent for producing lauric anhydride. As shown in Scheme 1, TFAA can be subsequently regenerated from TFA using phosphorous pentoxide (J. M. Tedder, Chem. Rev. 1955, 55 (5), 787-827; and T. P. Smyth, B. W. Corby, J. Org. Chem. 1998, 63, 8946-8951). By this recyclable reaction, molecules to be used for furan acylation, including but not limited to 2-dodecanoylfuran (DOF) and 2-furyl dodecyl ketone, can be prepared.

As seen in Scheme 6, 2-dodecanoylfuran or other acylated furans can be used to synthesize various types of renewable surfactants. The ketone group can be removed by the hydrogenation over a metal catalyst such as a copper-based catalyst, forming an alkylfuran such as 2-dodecylfuran (DF).

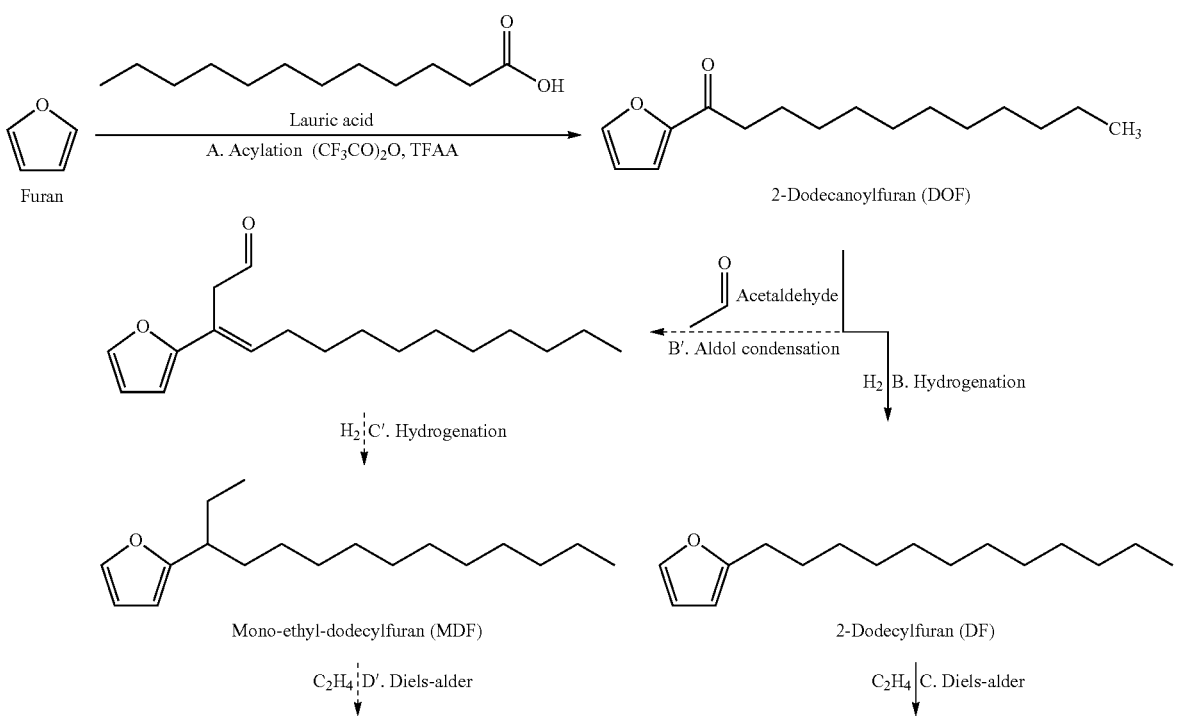

Scheme 6. Proposed pathways for renewable surfactants from furan and fatty acids. Presented pathways represent one of many possible permutations in the order in which the reactions are carried out.

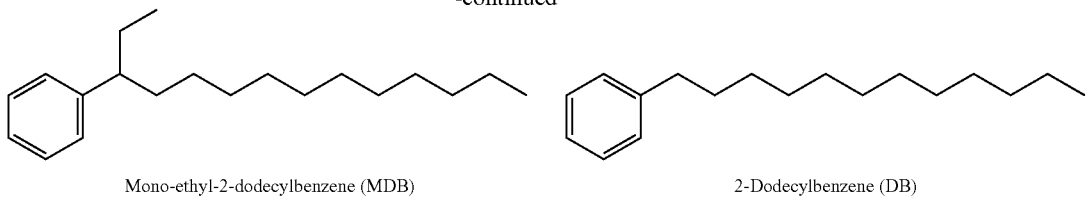

Mono-ethyl-2-dodecylbenzene (MDB)    2-Dodecylbenzene (DB)

The alkylfuran molecule can be used in one of two ways: (1) cycloaddition of alkylfuran to form alkylbenzene, which can then be subsequently functionalized with a hydrophilic moiety, such as a sulfonate in the case of LAS, or (2) direct functionalization of the alkylfuran with a hydrophilic moiety to form a furan-based surfactant for example.

Formation of the compounds can be achieved in numerous permutations of reaction orders as well as reaction conditions, such as temperature, pressure, reactant, and catalyst type, and combinations thereof. In some illustrative embodiments, methods can include four main steps or chemical reactions: acylation, hydrogenation, aldol condensation, and functionalization with a hydrophilic group, which can be performed in any order or simultaneously with any other reaction. Specifically, reactions such as the aldol condensation and sulfonation can be carried out at any point during the overall process, yielding a number of permutations in chemical reaction order. An example of one of these permutations is shown in Scheme 7, in which the 2-dodecylfuran molecule can be functionalized with a hydrophilic group before or after cycloaddition to form a benzene aromatic ring. In the case of these permutations, aldol condensation could also be performed at any step in the process.

Scheme 7. An example of one of the permutations of the order in which reactions are carried out shows that functionalization with a hydrophilic group (K) can occur either or after cycloaddition.

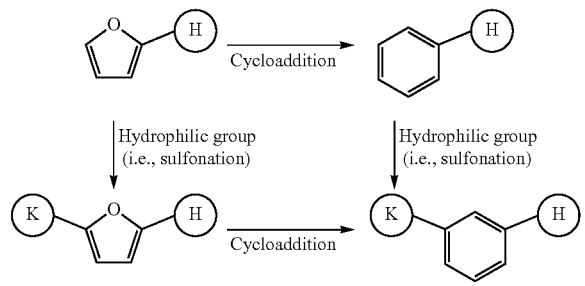

Additionally, each reaction presented can be carried out using a selection of acid, base, or metal catalysts (specific examples of which are illustrated in Table 1 above), which can be homogeneous, heterogeneous, or otherwise supported, or any combination of multiple catalysts. Reactions can also be carried out heterogeneously or homogeneously in the gas, liquid, or solid phases or any combination of phases or supercritical conditions.

Also disclosed herein is the use of heterogeneous catalysts for the efficient synthesis of surfactants from renewable furans or other aromatics and fatty acids with structures that can be modified or synthesized to form micelles in hard water (e.g. $Ca^{2+}$) at low temperatures.

In some embodiments, the preparation of disclosed aromatic surfactants utilizes furan or another aromatic as a linker connecting alkyl chains and sulfonate. As depicted in FIG. 2A, long (>C10) alkyl chains are obtained from hydrolysis of triglycerides to fatty acids such as lauric acid (C12), myristic acid (C14), or stearic acid (C18) and can be converted to anhydrides by numerous existing methods including dehydration in the presence of water sorbents or other short-chain recyclable anhydrides (T. P. Smyth, B. W. Corby, Toward a Clean Alternative to Friedel-Crafts Acylation: In Situ Formation, Observation, and Reaction of an Acyl Bis(trifluoroacetyl)phosphate and Related Structures. *The Journal of Organic Chemistry* 63, 8946-8951 (1998); published online Epub1998/11/01 (10.1021/jo981264v); and J. M. Tedder, The Use Of Trifluoroacetic Anhydride And Related Compounds In Organic Syntheses. *Chemical Reviews* 55, 787-827 (1955); published online Epub1955/10/01 (10.1021/cr50005a001)). Herein, the coupling of these long alkyl chain anhydrides with furans by Friedel-Crafts acylation with heterogeneous catalysts is demonstrated. As shown in FIG. 2B, the reaction of lauric anhydride with furan on either Lewis acid zeolites (such as Sn-BEA, Sn-MWW, or Sn-SPP) or Brønsted acid zeolites (such as Al-BEA or Al-SPP) exhibited significant activity for acylation. Acylation of furan occurs with varying activity on Sn and $H^+$ sites as well as large and small pore structures (FIG. 2B); yield of acylated furan was only 11% with Sn-BEA but was 89% with hierarchical porous Al-SPP after five hours of reaction at 180° C.

Figure 3A:
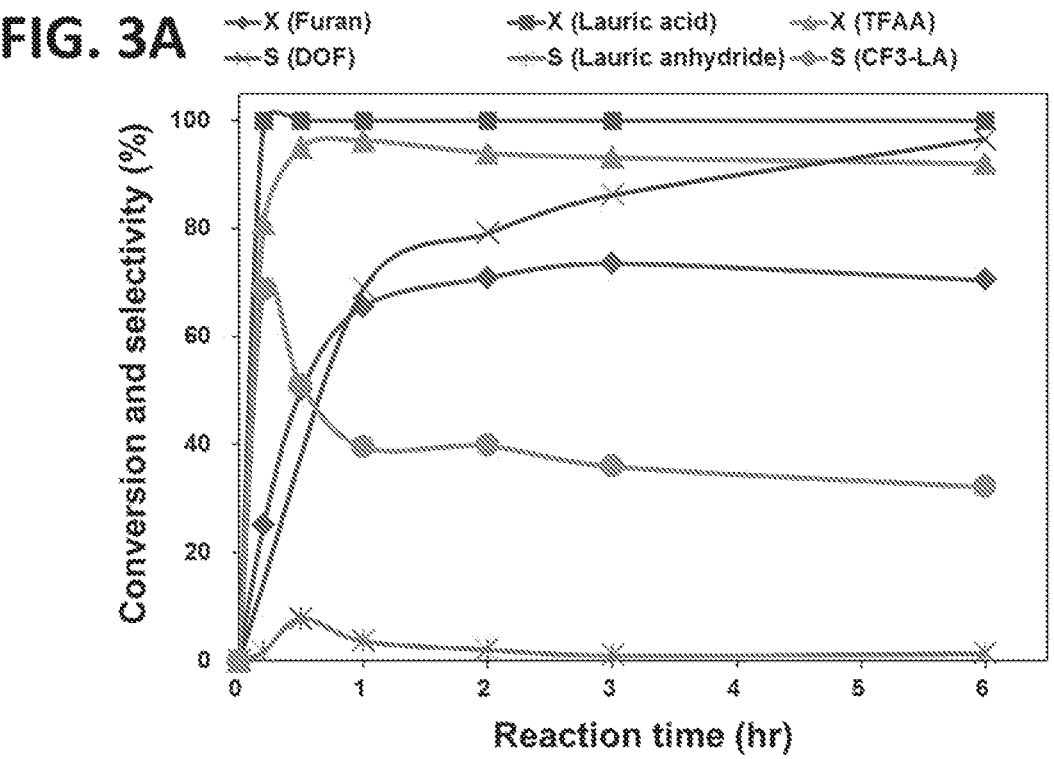
FIGS. 3A and 3B shows time-on-stream results for the acylation of furan and lauric acid with TFAA. DOF: 2-dodecanoylfuran, TFAA: Trifluoroacetic anhydride, Reaction conditions: 0.014 mol of furan, 0.018 mol of lauric acid, 0.02 mol of TFAA in 50 mL of hexane, 25° C., 1 atm (FIG. 3A) and the time-on-stream results for the hydrogenation of mixture of 2-dodecanoylfuran (DOF) and aldol-product (Al_DOF), (220° C., 100 psi of $H_2$, 0.5 g of copper chromite, 7 h) (FIG. 3B).
Figure 3B:
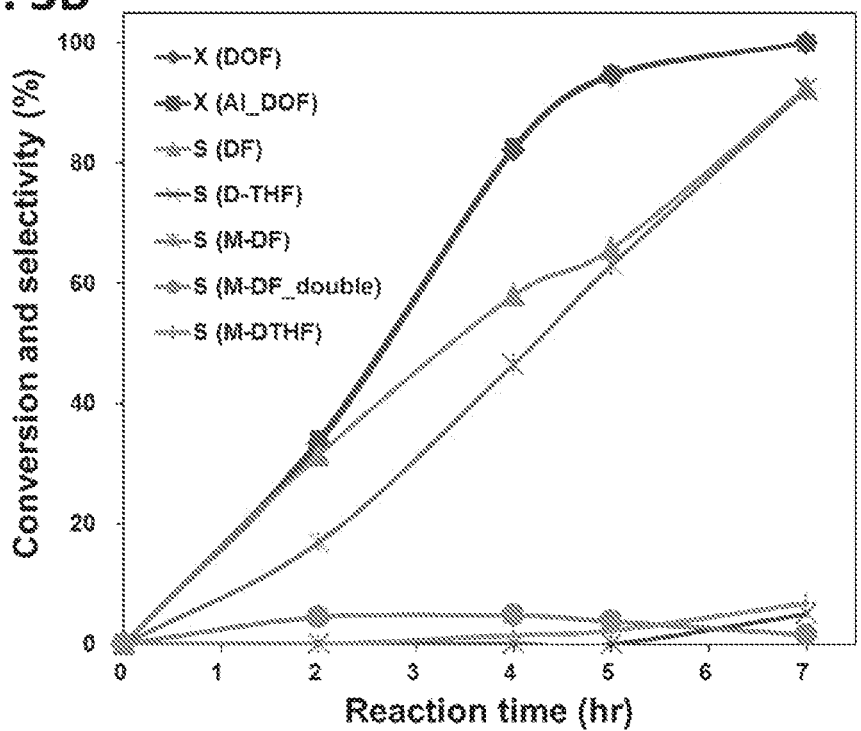

Alternatively, the two-step process of long-alkyl chain conversion to an anhydride and Friedel-Crafts acylation can occur simultaneously with the use of small anhydrides with strongly electron withdrawing groups. As shown in FIG. 2C, the reaction of furan, lauric acid and trifluoroacetic anhydride (TFAA) produces high yields of acylated furans. By varying the reaction temperature and ratio of the three components, yield of 2-dodecanoylfuran can be increased from about 50% to over 95% in only a few minutes. At lower concentrations, the time-resolved conversion of the three components was measured (FIG. 3A); lauric acid rapidly reacts with TFAA to form lauric anhydride and the mixed anhydride, which are consumed as acylation of the furan proceeds. By this method 2-dodecanoylfuran was recovered by evaporating any remaining furan, solvent, or trifluoroacetic acid, which can be recycled to TFAA (T. P. Smyth, B. W. Corby, Toward a Clean Alternative to Friedel-Crafts Acylation: In Situ Formation, Observation, and Reaction of an Acyl Bis(trifluoroacetyl)phosphate and Related Structures. *The Journal of Organic Chemistry* 63, 8946-8951 (1998); published online Epub1998/11/01 (10.1021/jo981264v)). FIG. 3B shows the time-on-stream results for the hydrogenation of mixture of 2-dodecanoylfuran (DOF) and aldol-product (Al_DOF), (220° C., 100 psi of $H_2$, 0.5 g of copper chromite, 7 h).

Long chain furan ketones such as 2-dodecanoylfuran (FIG. 2A) prepared by acylation provide the key capability for producing tunable surfactant chemicals. As shown in FIG. 2D, the ketone functionality can be eliminated by catalytic reduction with copper chromite ($2CuO—Cr_2O_3$) catalyst without hydrogenation of the furan ring. Variation of the reaction temperature and hydrogen pressure resulted in varying yield of the reduced 2-dodecylfuran from less than 1% (350 psi $H_2$, 220° C.) to over 91% (100 psi $H_2$, 220° C.). Additionally, a third class of branched alkylfurans was prepared by aldol condensation of C12 alkyl chain furan ketones with acetaldehyde. As depicted in FIG. 2E, aldol condensation preferentially occurred at the second carbon resulting in a best yield of 23% which was enhanced to a 40:60 mole ratio of branched versus straight chain OFS surfactants after hydrogenation with copper chromite and purification.

Figure 4:
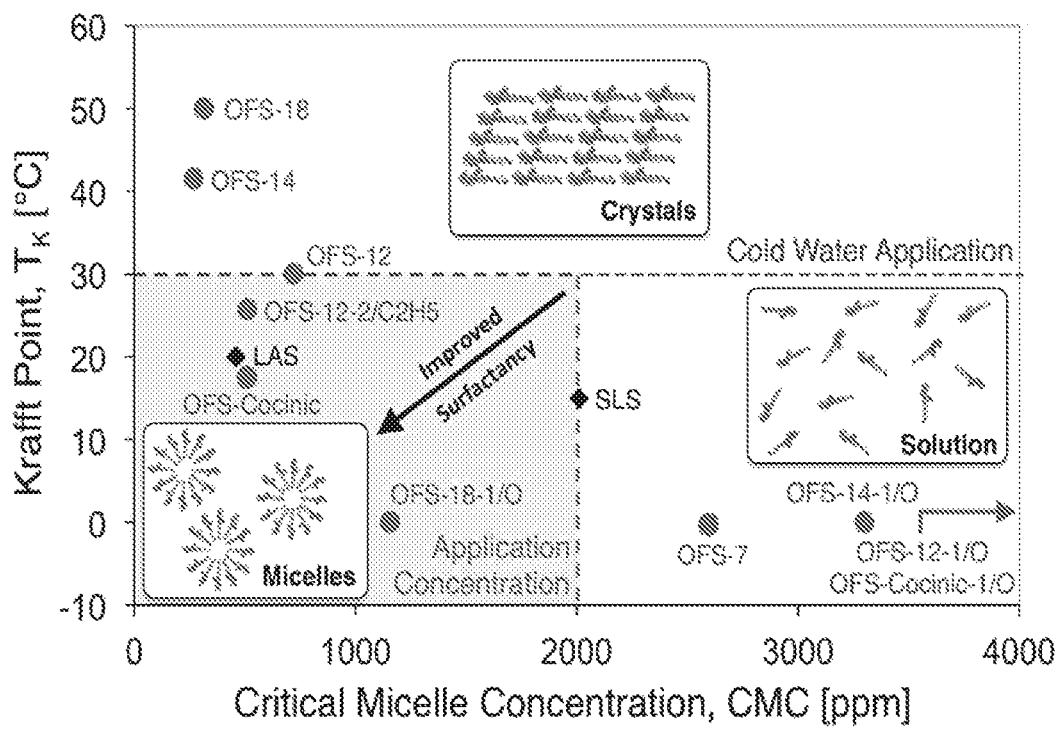
FIG. 4 shows a comparison of the surfactant critical micelle concentration (CMC) above which micelles form and the Krafft temperature (TK) below which surfactants crystallize as a separate solid phase. Optimal conditions for aqueous applications (grey box) require a Krafft point below 30° C. and a critical micelle concentration below about 2000 ppm. Linear chain oleo-furan sulfonate surfactants (OFS-12 and OFS-Cocinic) and branched OFS-12-2/C2H5 exhibit comparable or better properties when compared with linear alkylbenzene sulfonates (LAS).

A single acylation occurred overwhelmingly at the furan alpha carbon by either solid acid or TFAA methods as confirmed by NMR spectroscopy, and multiple acylation additions to furan were not observed. The remaining furan alpha carbon could then be sulfonated by existing commercial methods of sulfur trioxide sulfonation or the laboratory method with a sulfur trioxide-pyridine complex (G. Trummlitz, E. Seeger, W. Engel, "4-5-Dimethyl-thieno[3,2-d] ISO-thiazolo-3(2H)-one-1,1-dioxides, compositions, and methods of use as a sweetener," U.S. Pat. No. 4,233,333, Nov. 11, 1980; and WO 2015084813), which yielded high purity alkyl-furan-sulfonate. As seen in Table 13 below, sulfonation of three acylated furans including C12, C14 and C18 yielded three oleo-furan sulfonate surfactants identified as OFS-n-1/O to denote the ketone functionality on the alkyl chain at the first carbon position. A fourth ketone surfactant was prepared from cocinic acid, a mixture of C8 to C18 fatty acids. Linear (OFS-n) surfactants prepared by hydrogenation and branched (OFS-12-2/$C_2H_5$) surfactants prepared by aldol condensation were sulfonated by the same method. Preparation of precise oleo-furan surfactant molecules permitted evaluation of colloidal properties relative to surfactant structure. As shown in FIG. 4, surfactant performance was evaluated by measuring the critical micelle concentration (CMC), defined as the minimum concentration for which dissolved surfactants spontaneously self-assemble to micelles. Surfactants were also characterized by their Krafft temperature ($T_K$), defined as the temperature below which surfactants form solid crystals. Dashed lines denoting the requirements of common aqueous application concentration (2000 ppm, red) and cold water detergency (30° C., blue) form the bounds of the lower left region of FIG. 3, at which the surfactant has desirable properties in cold water and dilute conditions.

TABLE 13

Oleo-Furan and Commerical Surfactant Structure and Property Characteristics.

| Surfactant | Structure | CMC[a] [ppm] | Krafft Point[b] [° C.] | Draves Wetting[c] [s] | Foam Growth Rate[d] $r_i/r_{SLS}$ [-] | Foam Height$_{60}$[e] $h_{i-60}/h_{SLS-60}$ [-] | Micelle Stability[f] [ppm $Ca^{2+}$] |
|---|---|---|---|---|---|---|---|
| Commercial | | | | | | | |
| SLS, Sodium Laryl Sulfate | | 2010 | 15 | 6.3 | 1.00 | 1.00 | 33 |
| MES, Methyl Ester Sulfonate | 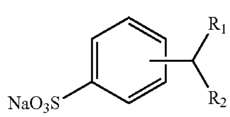 | 130 | <0 | 15.1 | 0.79 | 0.54 | 500 |
| LAS, Linear Alkylbenzene Sulfonate | | 460 | 20 | 4.9 | 1.36 | 2.20 | 100 |
| SLES, Sodium Laryl Ether Sulfate | | 380 | <0 | 15.4 | 1.60 | 2.94 | >50,000 |
| OFS, Oleo-Furan Sulfonates | | | | | | | |
| OFS-n-1/O | | | | | | | |
| n = 12 | | 11520 | <0 | >3600 | 0 | 0 | 230 |
| n = 14 | | 3127 | <0 | >3600 | 0 | 0 | 33 |
| n = 18 | | 1156 | <0 | >3600 | 0 | 0 | >50,000 |
| Cocinic, n = 8.18 | | 4890 | <0 | >3600 | 0 | 0 | 6600 |
| OFS-n | | | | | | | |
| n = 7 | 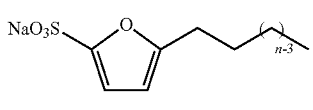 | 2669 | <0 | >3600 | 1.04 | 0.12 | 120 |
| n = 12 | | 720 | 30 | 48.9 | 1.83 | 2.11 | >50,000 |
| n = 14 | | 267 | 41.5 | 39.4 | 2.34 | 0.75 | >50,000 |
| n = 18 | | 316 | >50 | – | – | — | 33,000 |
| Cocinic, n = 8-18 | | 512 | 18.5 | 58.0 | 2.06 | 2.19 | >50,000 |
| 40:60 mol % OFS-12-2/C2H5:OFS-12 | | 510 | 25.7 | 18.5 | 1.96 | 2.37 | 2000 |
| 85:15 mol % OFS-12-1/O:OFS-12 | | 2445 | <0 | — | — | — | — |

[a] Critical Micelle Concentration, Measured above Krafft point.
[b] Measured at 1.0 wt % surfactant in water.
[c] Measured at 0.25 wt % in water.
[d,e] Measured at 0.5 wt % in water.
[e] At 60 minutes.
[f] Measured at twoce CMC.

Direct comparison of OFS and LAS reveals that the oleo-furan structure exhibits superior detergency. As depicted in FIG. 4 and listed in Table 13, OFS-12 with a linear alkyl chain achieves feasible performance (CMC of 720 ppm, TK of 30° C.) while the analogous LAS-12 linear alkyl chain has a higher Krafft temperature of 58° C. (J. G. Ma, B. J. Boyd, C. J. Drummond, Positional isomers of linear sodium dodecyl benzene sulfonate: Solubility, self-assembly, and air/water interfacial activity. Langmuir 22, 8646-8654 (2006)); the furan linker moiety can therefore be interpreted as improving surfactant solubility relative to benzene. Introduction of moderate two-carbon branching in a 40:60 ratio of OFS-12-2/C2H5:OFS-12 also lowers the CMC and Krafft temperature, further improving surfactancy. However, the most dramatic performance enhancement was derived from the mixture of linear alkyl chains found in OFS-Cocinic (CMC of 512 ppm, TK of 18° C.): the variation of linear alkyl chain lengths in OFS-Cocinic with a furan linker is comparable to branched LAS (CMC of 460 ppm, $T_K$=20° C.).

Figure 5A:
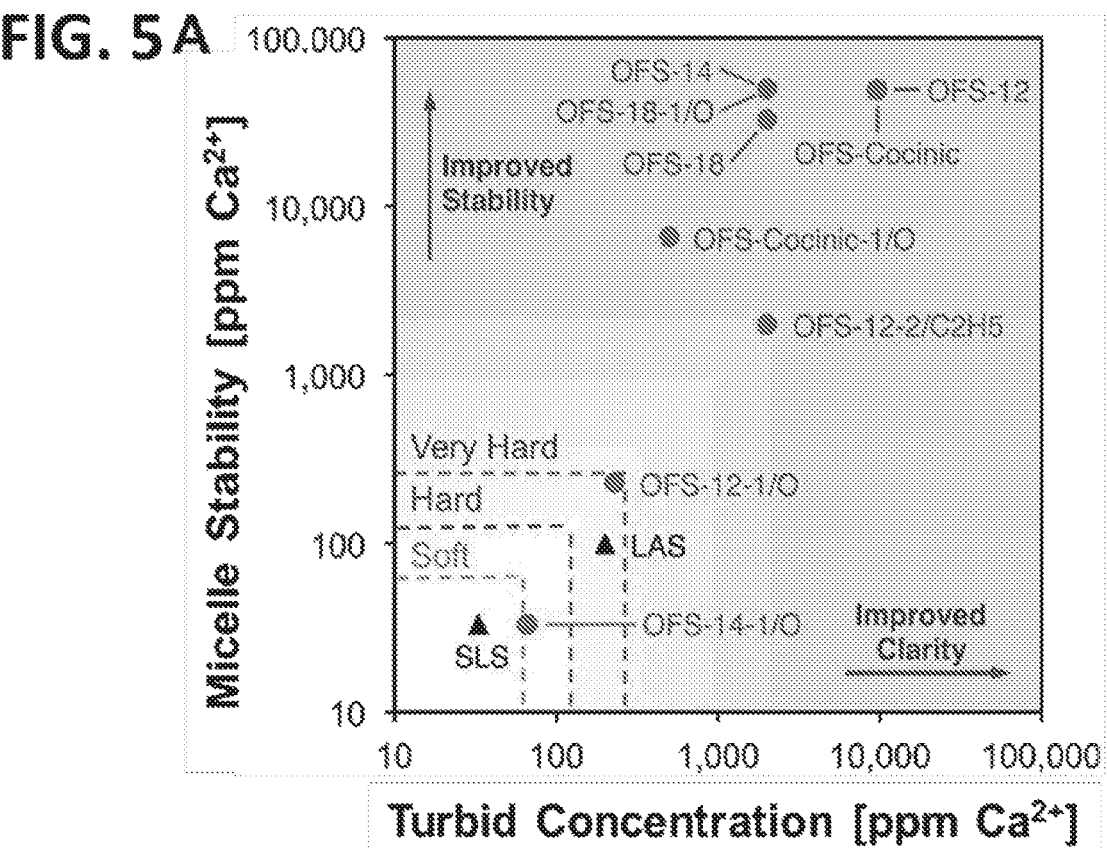
FIGS. 5A and 5B show a comparison of sulfonated surfactants for micelle stability and solution turbidity (FIG. 5A) for a range of soft to moderately hard water (0-120 ppm), hard (121-150 ppm) and very hard (>251 ppm) water reveals that most oleo-furan surfactants remain clear and functional in hard water conditions when viewed through a cuvette (FIG. 5B), while conventional surfactants such as LAS become cloudy (230 ppm) and precipitate (10,000 ppm).
Figure 5B:
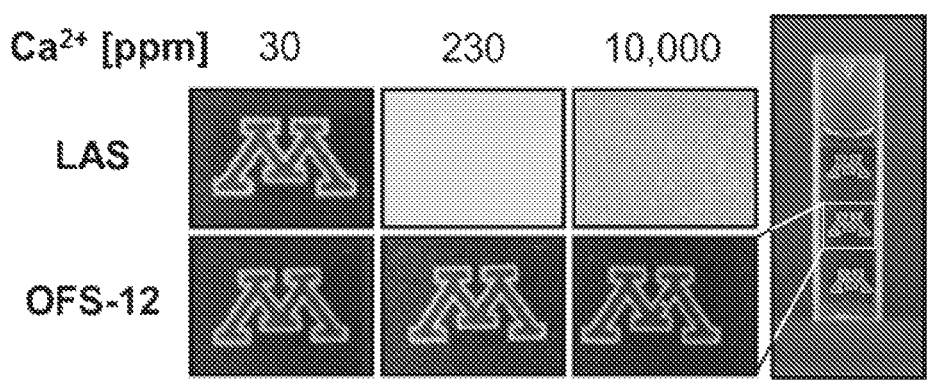

Performance of OFS in hard water conditions indicates dramatically enhanced surfactant stability of furan-based OFS molecules compared with conventional benzene-based and linear surfactants. FIG. 5A depicts the concentration [ppm] of hard water ions, $Ca^{2+}$, with two surfactant performance descriptors. Solution turbidity [ppm] was defined as the $Ca^{2+}$ concentration for which the aqueous surfactant solution visually lost its clarity due to formation of crystals. Micelle stability was identified as the $Ca^{2+}$ concentration [ppm] at which the solution surface tension began increasing associated with loss in surfactant performance. FIG. 5B shows a visual comparison of soft to moderately hard water (0-120 ppm), hard (121-150 ppm) and very hard (>251 ppm) water revealing that most oleo-furan surfactants remain clear and functional in hard water conditions when viewed through a cuvette, while conventional surfactants such as LAS become cloudy (230 ppm) and precipitate (10,000 ppm). Comparison of OFS stability overlaid with $Ca^{2+}$ concentrations common to soft and hard water applications (J. C. Briggs, J. F. Ficke, "Quality of rivers of the United States, 1975 water year; based on the National Stream Quality Accounting Network (NASQAN)," (US Geological Survey, 1977)) demonstrates a two-order-of-magnitude increase in stability of OFS molecules when compared with conventional surfactants. OFS-n surfactants exhibit $Ca^{2+}$ turbid and stability concentrations in the range of 10,000 ppm, while conventional LAS and SLS surfactants are in the 10-100 ppm range. Thus, OFS surfactants retain surfactancy in extreme hard water conditions without the need for co-formulation of chelating agents.

Additional performance metrics indicate that OFS surfactants exhibit sufficiently fast wetting kinetics and foaming behavior which is discussed in the experimental section following. Surfactant wetting kinetics, as measured by the Draves test, determines the rate at which an aqueous surfactant solution wets hydrophobic surfaces. The time ($T_D$) required for surfactant wetting of a cotton skein (i.e. Draves wetting test) in Table 13 indicates desirable wetting characteristics for all OFS-n structures ($T_D$ less than one minute), suitable for applications requiring fast-acting surfactants (M. Showell, Handbook of detergents, part D: formulation. (CRC Press, 2016), vol. 128). Additionally, aqueous surfactant solutions were characterized for their ability to grow foams and stabilize a height of foam at steady state (Table 13) (J. Falbe, Surfactants in Consumer Products. (Springer-Verlag, Heidelberg Germany, 1987). By bubbling air through a graduated cylinder of surfactant solution, the foam growth rate (r) and steady state foam heights (h) were measured. Comparison of foam growth rate and foam height, as shown in Table 13 shows that OFS-n molecules have similar foaming performance to conventional LAS surfactants.

Facile assembly of xylose-derived furan molecules with triglyceride-derived fatty acids into oleo-furan surfactants demonstrates a highly tunable method for renewable surfactant synthesis. The ability to precisely select and assemble with heterogeneous catalysts amenable to chemical processing allows for the chemical targeting of specific surfactant performance. By this approach, the optimal OFS molecules such as OFS-12 or OFS-Cocinic demonstrate strong surfactant performance in minimal concentrations and low temperatures compared with current large volume surfactants. These surfactants utilize straight alkyl chains that are optimal for biodegradation (M. J. Scott, M. N. Jones, The biodegradation of surfactants in the environment. Biochimica et Biophysica Acta (BBA)—Biomembranes 1508, 235-251 (2000); published online Epub11/23/ (http://dx.doi.org/10.1016/S0304-4157(00)00013-7); J. J. Scheibel, The evolution of anionic surfactant technology to meet the requirements of the laundry detergent industry. Journal of Surfactants and Detergents 7, 319-328 (2015); published online Epub2015//(10.1007/s11743-004-0317-7); and D. Bajpai, V. K. Tyagi, Laundry Detergents: An Overview. Journal of Oleo Science 56, 327-340 (2007)10.5650/jos.56.327)). More importantly, enhanced hard water stability of the OFS platform of molecules permits surfactant function in extremely hard water. This lack of sensitivity to metal ions enables formulation of surfactant systems free of chelating agents, capturing a broad range of applications in hard water and simplifying formulation of application specific surfactant systems.

Disclosed surfactants can be utilized for virtually any application. An illustrative application includes the chemical industry, for example the production of consumer products, such as detergents, cleaners, and personal care products. Surfactant production is relevant to manufacturers who produce bulk surfactants, as well as formulators, who generate consumer products containing surfactants.

Illustrative uses for surfactants can include two primary product classes: (1) cleaning components, with formulations that include surfactants, builders, carriers, enzymes, alkalis, organic polymeric compounds, dyes/colorants, bleaches, alkanolamines, soil suspension agents, abrasives, fabric softening agents, fragrances, hydrotopes, opacifiers, preservatives, processing aids, solvents, sud control agents, antimicrobial agents, antiredeposition agents, and corrosion inhibitors, and (2) personal care products, with formulations that include surfactants, oils, emollients, moisturizers, carriers, extracts, vitamins, minerals, alkalis, anti-aging compounds, solvents, polymers, preservatives, antimicrobials, waxes, particles, colorants/dyes, abrasives, opacifiers, processing aids, and fragrances.

Cleaning component formulations can take the form of liquid detergents, such as laundry, dishwashing, and hand dishwashing detergents, solid detergents, including powders, bars, and tablets, as well as industrial cleaners, hard surface cleaners, disinfectants, and decontaminants.

Personal care product formulations can take the form of hair shampoos, conditioners, and treatments, as well as body wash, lotion, facial and body soap, foam bath, make-up removers, skin care products, acne control products, shaving aids, deodorants, antiperspirants, cosmetics, depilatory, and fragrances.

This disclosure is further illustrated by the following examples. It is to be understood that the particular examples, materials, amounts, and procedures are to be interpreted broadly in accordance with the scope and spirit of the disclosure as set forth herein.

EXAMPLES

Materials

Hexane (95%), Furan (99%), and Trifluoroacetic anhydride (99%) were purchased from Sigma-Aldrich. The saturated fatty acids, lauric acid (C12, 99%, Acros), myristic acid (C14, 99%, Sigma-Aldrich), stearic acid (C18, 95%, Sigma-Aldrich), and cocinic acid (mixture of fatty acids, C8~C18, BOC Sciences) were used in furan acylation for the first step in overall reaction pathway. The reference standards, 2-n-heptylfuran (98%) and 2-n-dodecylfuran (95%) were purchased from Alfa Aesar and MP Biomedical, respectively. Lauric anhydride (98%, TCI Chemicals) was also used for furan acylation with solid acid catalysts. H-BEA catalyst (CP814E, Si/Al=12.5) and copper chromite catalyst were obtained from Zeolyst and Sigma-Aldrich, respectively. The H-BEA was calcined at 550° C. for 12 h at the rate of 1° C. min-1 in a tube furnace under air flow. The reduction of copper chromite was carried out at 300° C. for 3 h under 10% $H_2$/Argon flow.

For the purpose of evaluation and comparison of the performance of disclosed surfactants, four different anionic commercial surfactants were purchased; linear alkylbenzene sulfonate (sodium dodecylbenzene sulfonate, 79.7%, Sigma-Aldrich), sodium lauryl sulfate (sodium dodecyl sulfate, 99.1%, Sigma-Aldrich), sodium lauryl ether sulfate (70.4%, BOC Sciences) and methyl ester sulfonate (Alpha-Step MC-48, 38.76%, Stepan).

Zeolite Synthesis Methods

Several types of self-pillared zeolites, Al/Sn-SPP and Al/Sn-MWW were used as catalysts in furan acylation with anhydride after calcination at 500° C. for 4 h.

Sn-MWW synthesis: Sn-MWW was synthesized by modifying an existing literature method (Q. Guo, F. Fan, E. A. Pidko, W. N. P. van der Graff, Z. Feng, C. Li, E. J. M. Hensen, Highly active and recyclable Sn-MWW zeolite catalyst for sugar conversion to methyl lactate and lactic acid. *ChemSusChem* 6, 1352-1356 (2013)). First, B-MWW precursor was de-boronated by 6M $HNO_3$ (1 g zeolite/50 mL $HNO_3$) at 100° C. under reflux for 1 day, this procedure was performed twice. Then 2.5 g of the de-boronated sample was mixed with 30 g of distilled water and 3.549 g of piperidine (99%, Aldrich). After stirring for 1 hour, 0.146 g of tin tetrachloride pentahydrate ($SnCl_4 \cdot 5H_2O$, 98%, Aldrich) was added into the above mixture and stirred for 2 hours. Then the final gel with chemical composition 1$SiO_2$: 0.01 $SnO_2$: 1.0 piperidine: 40 $H_2O$ was transferred to an autoclave and hydrothermally treated in a rotation oven at 170° C. for 14 days. The products were separated and fully washed by filtration and then dried at 70° C. overnight. Calcination of this sample was performed in static air at 580° C. for 10 hours.

Sn-SPP synthesis: First, 0.129 g of tin tetrachloride pentahydrate ($SnCl_4 \cdot 5H_2O$, 98%, Sigma-Aldrich) was dissolved into 7.35 g of tetra(n-butyl)phosphonium hydroxide (TBPOH, 40 wt %, TCI America) followed by the addition of 7.5 g of tetraethyl orthosilicate (TEOS, 98%, Sigma-Aldrich). After hydrolysis, 3.2 g of deionized water was added to the mixture. The mixture was stirred overnight, and a clear sol was obtained. The composition of the final sol was: 1.0 $SiO_2$:0.03 TBPOH:4.0 EtOH:30$H_2O$:0.01$SnO_2$.

The sol was sealed in a Teflon-lined stainless steel autoclave and hydrothermally treated in a pre-heated static oven at 115° C. for 5 days. The solid products were centrifuged, washed with distilled water and then dried at 70° C. overnight and calcined at 550° C. for 6 h in air under static conditions. The calcined samples were washed again with water, dried at 70° C. overnight and calcined at 550° C. for 6 h in air under static conditions and this process was repeated to ensure removal of $P_2O_5$.

Al-MWW synthesis: Al-MWW was synthesized according to a literature method (A. Corma, V. Fornés, J. Martinez-Triguero, S. B. Pergher, Delaminated zeolites: Combining the benefits of zeolites and mesoporous materials for catalytic uses. *J. Catal.* 186, 57-63 (1999)). First, 0.72 g of sodium aluminate (MP Biomedicals, USA) and 2.48 g of sodium hydroxide (98.5%, Sigma-Aldrich) were dissolved in 311 g of distilled water. Then, 19.1 g of hexamethyleneimine (HMI) (Aldrich) was added to the mixture and stirred for 30 min. Subsequently 23.6 g of fumed silica (Cab-o-sil M5) was added to the mixture and stirred overnight. The homogeneous gel was sealed in Teflon-lined stainless steel autoclaves and heated at 135° C. for 11 days. The products were separated and fully washed by filtration followed by drying at 70° C. overnight, then calcined at 580° C. in static air for 10 hours.

Al-SPP synthesis: 0.098 g of Aluminum isopropoxide (Sigma-Aldrich) was mixed with 3.23 g of distilled water and 7.35 g of tetra(n-butyl)phosphonium hydroxide solution (TBPOH, 40 wt %, TCI America). The mixture was added to 7.5 g of tetraethyl orthosilicate (TEOS, Sigma-Aldrich) and stirred overnight. The sol was sealed in a Teflon-lined stainless steel autoclave and hydrothermally treated in a pre-heated static oven at 115° C. for 5 days. The solid products were centrifuged, washed with distilled water and then dried at 70° C. overnight and calcined at 550° C. for 6 h in air under static conditions.

Ion exchange to obtain the proton form Al-zeolites: Typically, ion exchange was performed by stirring Al-zeolites with 1M ammonium nitrate ($NH_4NO_3$, Sigma-Aldrich) solution (1 g zeolite+100 ml $NH_4NO_3$ solution) at 80° C. for 5 h. After stirring, zeolites products were centrifuged, washed with distilled water and then dried at 70° C. overnight and calcined at 500° C. for 4 h in air under static conditions. The whole procedure was performed twice for complete ion exchange.

Mg—Zr—O synthesis: The mixed oxide, Mg—Zr—O, catalyst was synthesized by sol-gel method. 0.01 mol of magnesium nitrate (Sigma-Aldrich, 99%) and 0.009 mol of zirconyl nitrate (Sigma-Aldrich, 99%) were mixed in DI water at room temperature. NaOH was added to the mixtures until the pH was 10, and the slurry was aged at room temperature for 72 h. The slurry was filtered and washed with DI water, and then, dried at 110° C. for 24 h. The catalyst was then calcined at 600° C. for 3 h before being used for aldol-condensation reaction (L. Faba, E. Díaz, S. Ordóñez, Performance of bifunctional Pd/MxNyO (M=Mg, Ca; N=Zr, Al) catalysts for aldolization-hydrogenation of furfural-acetone mixtures. *Catal. Today.* 164, 451-456 (2011)).

K-BEA and K-Y synthesis: K-BEA and K-Y zeolites were prepared by typical ion-exchange method. 2.5 g of zeolite (H-BEA or H-Y) was added to 0.6 M solution of $KNO_3$ (Sigma-Aldrich, 99%). The mixture was aged at 70° C. for 10 h with vigorous stirring in a round bottom flask connected with a condenser. After filtration and washing with DI water, the powder was dried at 100° C. for 24 h and calcined at 500° C. for 4 h (T. Tago, H. Konno, S. Ikeda, S. Yamazaki, W. Ninomiya, Y. Nakasaka, T. Masuda, Selective production of isobutylene from acetone over alkali metal ion-exchanged BEA zeolites. *Catal. Today.* 164, 158-162 (2011)).

Procedure for Preparation of Fatty Acid Anhydrides from Corresponding Fatty Acids Fatty acids can be converted to their corresponding anhydride by various existing methods such as heating the acid with a dehydrating agent like acetic anhydride whereby the carboxylic acid gets dehydrated to the anhydride and the acetic anhydride gets hydrated to the acid form. One way of achieving this is by passing excess amounts of acetic acid vapor through molten fatty acid. Fatty acid anhydride can also be produced by heating the acid with liquid acetic anhydride in the presence of an organic solvent like toluene, ethylbenzene or tetrachloroethylene which forms an azeotrope with acetic anhydride (U.S. Pat. No. 2,411,567). This method promises good yields of fatty acid anhydrides using lesser amounts of acetic anhydride as compared to the previous vapor method. In this method, a mixture of fatty acid, acetic anhydride and the azeotropic agent (solvent) is heated to 120° C. at atmospheric pressure. As the reaction occurs, the azeotropic mixture of acetic acid and solvent is distilled off and any vaporized acetic anhydride is condensed and returned to the reaction vessel. An increase in the temperature of the reaction mixture marks the completion of reaction. A third method for the synthesis of fatty acid anhydrides makes use of a metal salts such as salts of cobalt, manganese, palladium, copper, nickel, chromium, rhodium, thorium and iron (U.S. Pat. No. 4,477,382). The reaction is carried out between 140-220° C. in an inert atmosphere. Water produced during the dehydration of fatty acid is removed as an azeotrope with a hydrocarbon solvent such as linear alkanes, benzene, toluene etc. Examples of metal salts that can be used as catalysts include $Co(OAc)_2.4H_2O$, $Pd(OAc)_2$, $Cr(OAc)_3$, $Mn(OAc)_2.4H_2O$, $Th(NO_3)_4.4H_2O$, $Rh_2O_3$, $Cu(OAc)_2$ and $Fe(OAc)_3$.

Illustrative Specific Methods

Acylation reaction to form 2-dodecanoylfuran, hydrogenation reaction to form 2-dodecylfuran, and sulfonation to form sodium 2-dodecylfuran-5-sulfonate.

Hexane (95%), Furan (99%), and Trifluoroacetic anhydride (99%) were purchased from Sigma-Aldrich. Lauric acid (99%) was purchased from Acros, and n-tridecane (98%) was from Alfa Aesar. 2-dodecylfuran (95%) was purchased from MP Biomedical. H-BEA catalyst (CP814E, Si/Al=12.5) and copper chromite catalyst were obtained from Zeolyst and Sigma-Aldrich, respectively. H-BEA was calcined at 550° C. for 12 hr with a ramping rate of 1° C. min-1 in a tube furnace under air flow. The reduction of copper chromite was carried out at 300° C. for 3 hr under 10% H2/Argon flow.

Batch reactions for production of 2-dodecanoylfuran (DOF) were conducted in a 100 mL high pressure Parr Reactor. In a typical reaction, the Furan (1.0 mL, 0.014 mols), lauric acid (4.0 mL, 0.018 mols), trifluoroacetic anhydride (2.0 mL, 0.014 mols) and n-tridecane (internal standard, 0.5 mL, 0.002 mols) were dissolved in hexane (10 mL), and 0.2 g of the H-BEA catalyst was introduced to the mixture. The sealed reactor was purged with $N_2$ twice to remove the residual air in the reactor. The reactor was then heated to the reaction temperature (room temperature or 50-180° C.) under vigorous stirring (1,000 rpm). The reactor was subsequently pressurized to 200 psi (at desired temperature) with N2 to keep liquid phase of the reactants. After reaction for a desired reaction time, the reactor was cooled to room temperature and the gases were vented. The products were identified by a GC-MS (Agilent 7890A connected with Triple-Axis MS detector, Agilent 5975C) and quantified by a GC (Agilent 7890A) equipped with an HP-5 column and a flame ionization detector. The selectivity of the 2-dodecanoylfuran was calculated to the produced moles of DOF over the reacted moles of the furans. The response factor of the DOF was determined by the QCD method (S. Maduskar, A. R. Teixeira, A. D. Paulsen, C. Krumm, T. J. Mountziaris, W. Fan, P. J. Dauenhauer, Lab Chip 2015, 15, 440-447), because the standard chemical of 2-dodecanoylfuran was not supplied commercially.

Hydrogenation of 2-dodecanoylfuran to make 2-dodecylfuran (DF) was carried out in a 100 mL Parr reactor. The prepared 2-dodecanoylfuran (2.0 mL, 0.0077 mols) and n-tridecane (internal standard, 0.5 mL, 0.002 mols) were dissolved in hexane (30 mL), and 0.5 g of copper chromite catalyst was introduced to the mixture. The reactor was pressurized with hydrogen in a range of 100-350 psi at the desired reaction temperature (180-220° C.). The selectivity of the 2-dodecylfuran was calculated to the produced moles of DF over the reacted moles of the DOF.

The desired products (DOF and DF) were concentrated by rotary evaporator (Hei-VAP/G5, Heidolph) with liquid nitrogen in the condenser. Several batch reactions were conducted without the internal standard chemical (n-tridecane) to collect the product solutions. The rotary evaporator was operated at room temperature for 30 min under high vacuum to remove the light molecules (hexane, furan, TFAA and TFA). Afterwards, the remaining solution was further concentrated at 70° C. for 2 hr under high vacuum.

2-dodecylfuran was sulfonated and neutralized to make sodium 2-dodecylfuran-5-sulfonate by three different methods as follows. Method 1: 2-dodecylfuran (5.9 g, 25 mmol) was dissolved in isopropanol (100 mL), and the solution was added to a solution of $NaHSO_3$ (5.2 g, 50 mmol) in water (75 mL). The mixture was stirred at 50° C. for 28 hr (A. Gassama, Cédric Ernenwein, A. Youssef, M. Agach, E. Riguet, S. Marinković, B. Estrine, N. Hoffmann, Green Chem. 2013, 15, 1558-1566). Method 2: 2-dodecylfuran (5.9 g, 25 mmol) was added to a slurry of sulfur trioxide-pyridine complex (4 g, 25 mmol) in 1,2-dichloroethane (25 mL), and the mixture stirred at room temperature for 3 days. After then, warm water (75 mL) was introduced to the slurry. The aqueous phase was controlled to a pH 7.5 using sodium carbonate and then evaporated to crystalline phase (J. F. Scully, E. V. Brown, J. Org. Chem. 1954, 19(6), 894-901; and G. Trummlitz, E. Seeger, W. Engel (Boehringer Ingelheim GmbH, Germany), 4,5-Dimethyl-Thieno [3,2-d] Iso-Thiazolo-3(2H)-One-1,1-Dioxides, Compositions, And Methods Of Use As A Sweetener, U.S. Pat. No. 4,233,333, Nov. 11, 1980). Method 3: 2-dodecylfuran (5.9 g, 25 mmol) was added to a slurry of sulfur trioxide-pyridine complex (5.7 g, 36 mmol) in acetonitrile (20 mL). The mixture was heated at 40° C. and stirred under nitrogen atmosphere. After 24 hr, the slurry was added to a solution of NaOMe/MeOH (7.8 g, 36 mmol) in methanol (20 mL). The solvent was evaporated overnight, and the residue mixture was added to warm water (70° C.). The mixture was placed in a refrigerator for 2.0 hr, and the crystalline phase was collected by filtration (US Pat. Pub. No. 2015/0150768).

The produced 2-dodecanoylfuran (DOF), 2-dodecylfuran (DF) and sodium dodecylfuran sulfonate (SDFS) were analyzed by 1H NMR spectroscopy (Bruker AX400, 400 MHz). The 1H NMR of the products were dissolved in $CDCl_3$ solutions containing with a 5 mM of tetramethylsilane (TMS) as an internal standard.

Surface tension and critical micelle concentration (CMC) of the surfactants were measured by Du Noüy ring method using a surface tensiometer. Krafft point (TK) of the surfactants was measured by estimating the degree of counterion dissociation using conductivity meter (COND 6+, Oakton/Eutech Instruments). An aqueous solution of surfactant concentrated to a CMC value was prepared and placed in a refrigerator for 4.0 hr. The solution was heated to 30-40° C. from 5-6° C. with a ramping rate of 0.5° C. min-1 under vigorous stirring (J. Z. Manojlović, Thermal Science 2012, 16, S631-S640; and C. Vautier-Giongo, B. L. Bales, J. Phys. Chem. B 2003, 107, 5398-5403).

Results

The acylation of furan with lauric acid was carried out at room temperature (r.t.) to 180° C. for 6.0 hr in hexane and THF solvents with trifluoroacetic anhydride. As seen in Table 14, the conversion of furan and lauric acid (LA) were 100% in a range of temperature from r.t. to 100° C.

TABLE 14

Summarized results for the acylation of furan with lauric acid and trifluoroacetic anhydride.

| Conditions | Furan conversion (%) | Lauric acid conversion (%) | TFAA conversion (%) | 2-dodecanoyl selectivity (%) |
|---|---|---|---|---|
| 25° C. (No Cat.) | 100 | 100 | 51.1 | 87.0 |
| 25° C. | 100 | 100 | 71.6 | 81.3 |
| 50° C. | 100 | 100 | 70.2 | 75.6 |
| 100° C. | 100 | 100 | 27.4 | 27.4 |
| 150° C. | 100 | 95.6 | 100 | 43.9 |
| 180° C. | 100 | 78.3 | 100 | 13.5 |
| 150° C. (THF) | 53.9 | 91.2 | 100 | 20.1 |

*Reaction Conditions: 200 psi ($N_2$), 0.014 mols of Furan, 0.018 mols of lauric acid, and 0.028 mols of TFAA in hexane (10 mL), HBEA 0.2 g, 6 hrs.

Figure 6A:
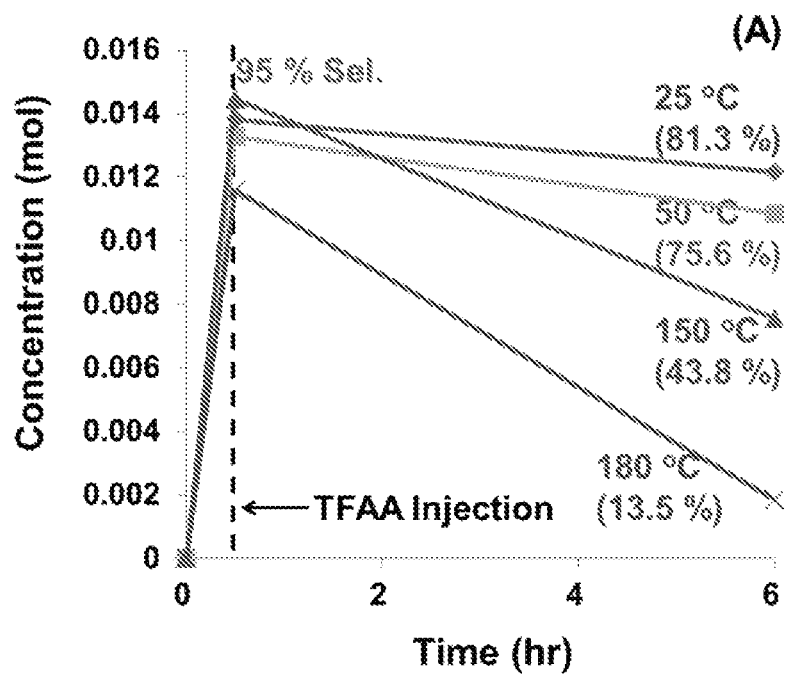
FIGS. 6A and 6B shows the change of concentrations of 2-dodecanoylfuran (FIG. 6A) and lauric acid (FIG. 6B) during reaction (Reaction Conditions: 200 psi ($N_2$), 0.014 mols of Furan, 0.018 mols of lauric acid, and 0.028 mols of TFAA in hexane (10 mL), HBEA 0.2 g, 6 hrs).
Figure 6B:
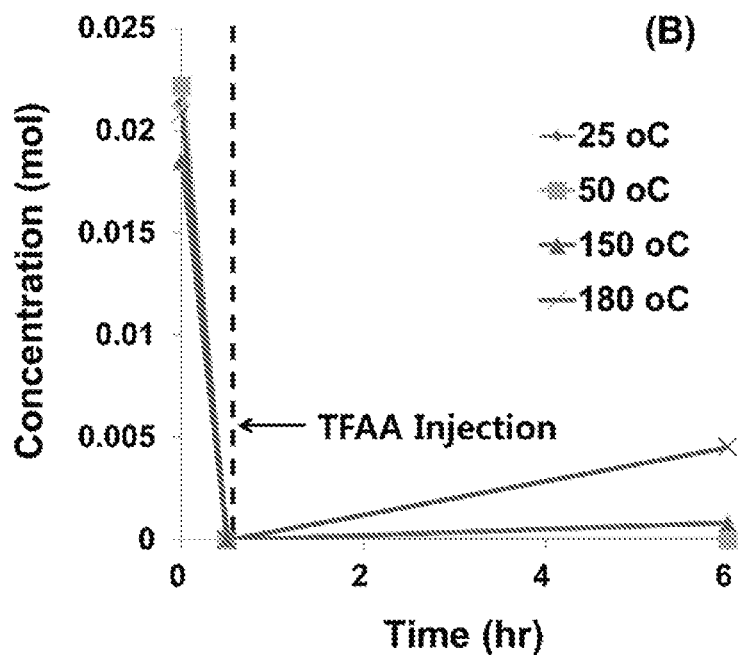
Figure 7:
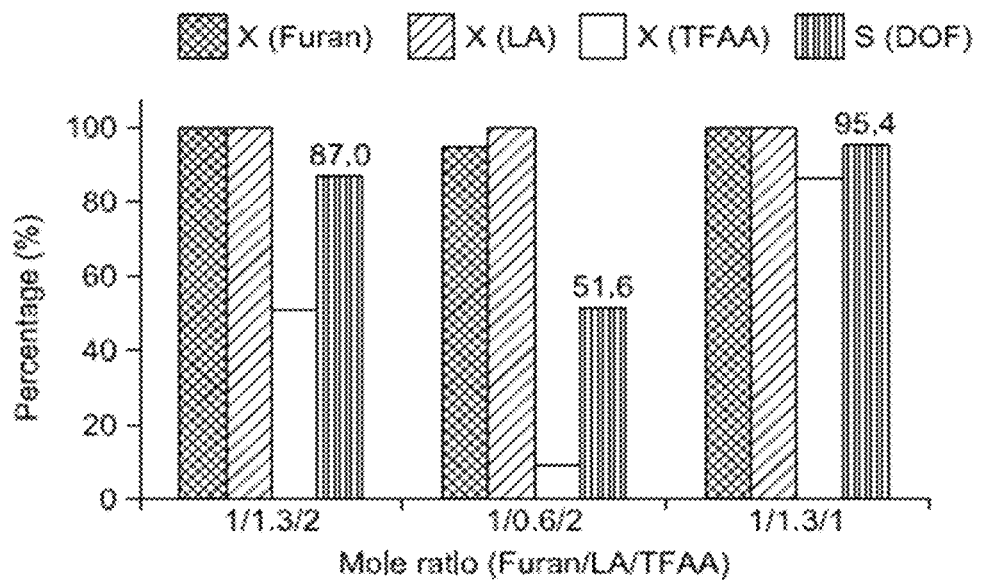
FIG. 7 shows results for the acylation of furan and lauric acid with different mole ratios of reactants (Mole ratio (1/1.3/1): 0.014 moles of Furan/0.018 moles of lauric acid/ 0.014 moles of TFAA, Reaction conditions: Room temperature, 1 atm, no catalysts).
Figure 8:
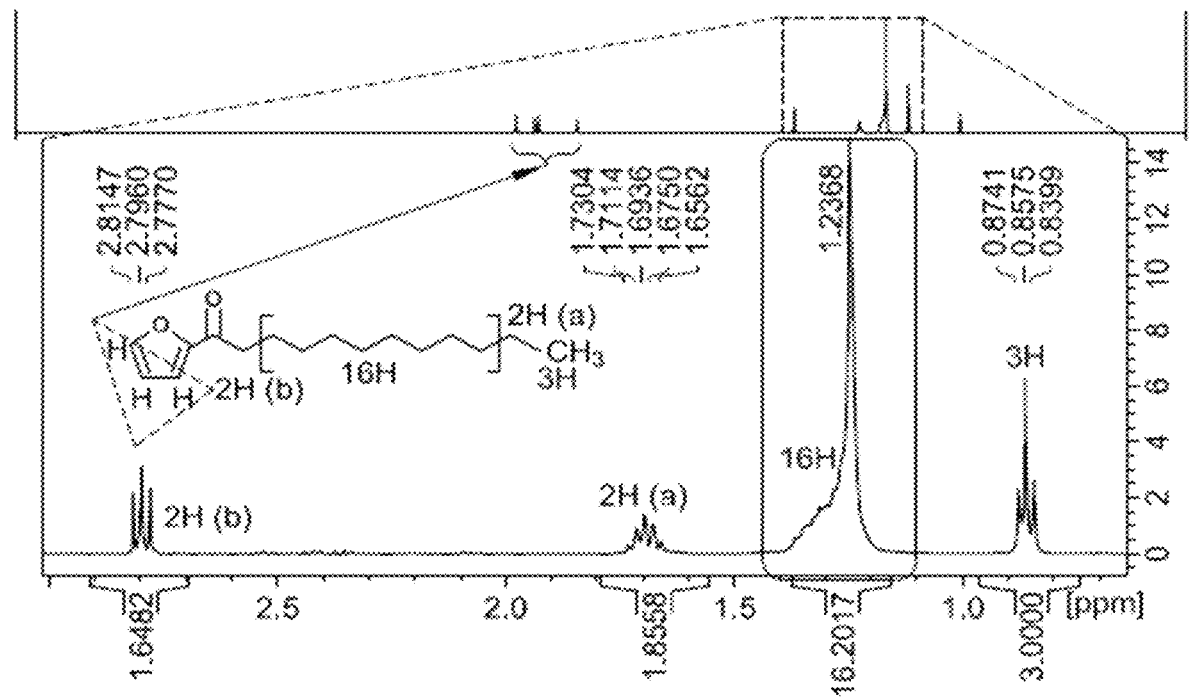
FIG. 8 shows the 1H NMR spectrum of purified and concentrated 2-dodecanoylfuran after acylation.

Above 150° C., the lauric acid (LA) conversion slightly decreased. With decreasing reaction temperature, the selectivity of 2-dodecanoylfuran (DOF) sharply increased up to 87% at room temperature without the H-BEA catalyst. In the use of THF solvent, acylation was not observed due to high reactivity of THF with trifluoroacetic anhydride. The selectivity to DOF was lower at high reaction temperatures, because acylation is a reversible reaction in the presence of trifluoroacetic anhydride. The data in FIGS. 6A and 6B show the change of concentration of 2-dodecanoylfuran (FIG. 6A) and lauric acid (FIG. 6B), respectively, during a reaction. After addition of the trifluoroacetic anhydride, DOF was rapidly produced with about 90-95% selectivity within a few minutes. However, the produced DOF gradually decreases with continued reaction. The decreasing rate of selectivity was faster at high temperatures. Above 150° C., conversion of lauric acid was reversed. We investigated the effect of mole ratio of reactants to production of DOF (FIG. 7) With a decrease the lauric acid concentration, the TFAA conversion and the selectivity of the DOF decreased. However, with an equimolar ratio of the furan and TFAA, the DOF selectivity increased to 95%, and the TFAA conversion also increased. Therefore, the reaction condition of the furan acylation with lauric acid under TFAA was carried out at room temperature, no catalyst, and the equimolar ratio of furan and TFAA. The 2-dodecanoylfuran, furyl lauryl ketone, prepared by acylation was identified by 1H NMR. As seen in FIG. 8, the broad multiply peak (chemical shift: 1.24~1.38 ppm) was calculated for the sixteen protons. Therefore, the produced furyl ethyl ketones were confirmed to consist of furyl-2-(C12 alkyl)-ketone, 2-dodecanoylfuran. (1H NMR (400 MHz, CDCl3): δ 0.84-0.87 (m, 3H), 1.24-1.38 (brm, 16H), 1.66-1.73 (m, 2H), 2.78-2.82 (m, 2H), 6.50-6.52 (m, 1H), 7.17-7.18 (m, 1H), 7.56 (m, 1H)) The 2-dodecanoylfuran was also identified by GC-MS. (GC MS (EI) m\z (relative intensity): 151 (3.4), 123 (20.1), 111 (10.9), 110 (99.9), 95 (31.6), 81 (2.6), 55 (5.5), 43 (4.4), 41 (6.2), 39 (3.6)).

Figure 9A:
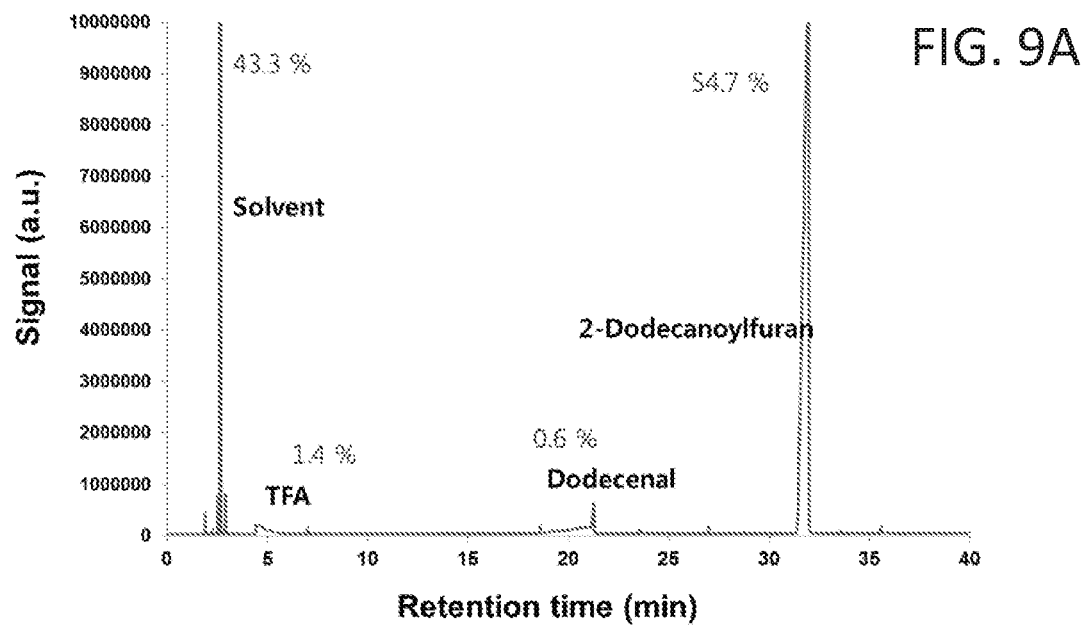
FIGS. 9A and 9B show typical GC profiles of product mixtures after acylation (FIG. 9A) and 2-dodecanoylfuran concentrated with rotary evaporator (FIG. 9B).
Figure 9B:
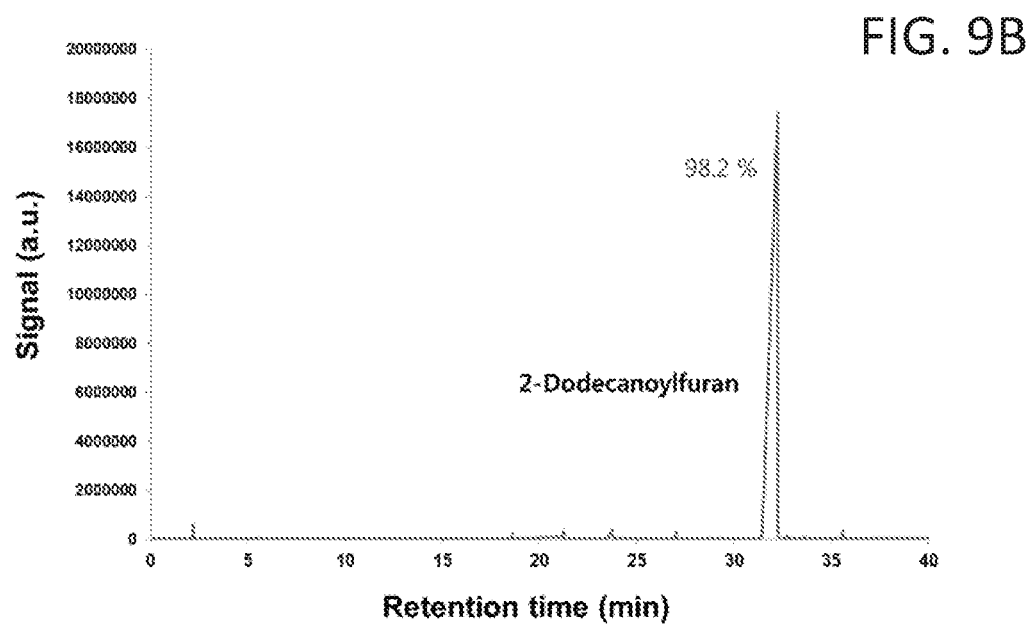

The acylation was carried out without an internal standard (n-tridecane) in several batches and the products were collected in order to use the 2-dodecanoylfuran as a reactant in hydrogenation (FIG. 9A shows the GC profile of the product mixtures after acylation). Concentrated 2-dodecanoylfuran was obtained with 98% purity using a rotary evaporator (FIG. 9B shows the GC profile of product mixtures after purification). The hydrogenation of 2-dodecanoylfuran was performed at 220° C. over copper chromite in various hydrogen pressures. The possible reaction scheme in hydrogenation of DOF over copper chromite is shown in Scheme 8.

Scheme 8. Liquid-phase hydrogenation of 2-dodecanoylfuran over copper chromite.

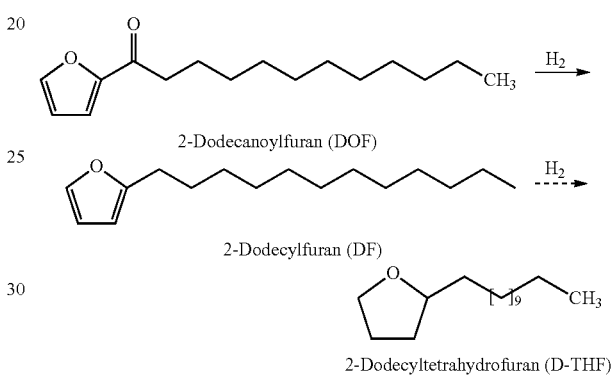

2-Dodecanoylfuran (DOF)

2-Dodecylfuran (DF)

2-Dodecyltetrahydrofuran (D-THF)

At first, a ketone group of DOF was removed by hydrogenation, resulting in production of 2-dodecylfuran (DF) as a desired product. However, 2-dodecyl-tetrahydrofuran (D-THF) can also be made by further hydrogenation of DF as a main side product. As shown in Table 15, when the reduced copper chromite was used for the catalyst, more amount of D-THF was produced than DF.

TABLE 15

Summarized results for the hydrogenation of 2-dodecanoylfuran.

| Conditions | 2-dodecanoyl-furan conversion (%) | 2-dodecyl-furan selectivity (%) | 2-dodecyl-tetra-hydrofuran selectivity (%) | Unknown selectivity (%) |
|---|---|---|---|---|
| 100 psi | 100 | 91.6 | 7.3 | 1.1 |
| 150 psi | 100 | 59.5 | 12.3 | 28.2 |
| 250 psi | 100 | 54.8 | 18.3 | 26.9 |
| 350 psi | 100 | 0.9 | 47.6 | 51.5 |
| 250 psi (Reduced CuCr) | 99.6 | 18.3 | 74.9 | 6.9 |

Figure 10A:
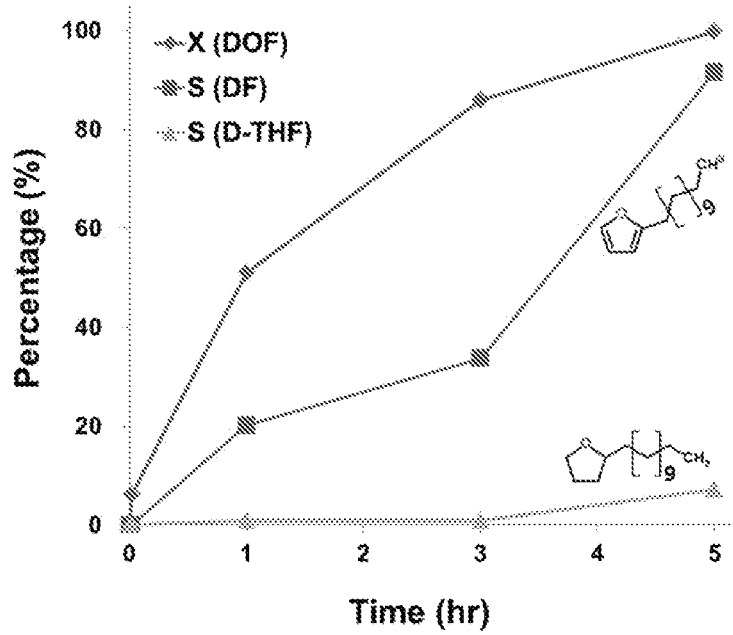
FIGS. 10A and 10B show time-on-stream results (conversion of 2-dodecanoylfuran and selectivities of 2-dodecylfuran and 2-dodecyl tetrahydrofuran) for the hydrogenation of 2-dodecanoylfuran in 100 (FIG. 10A) and 350 psi (FIG. 10B) of $H_2$.
Figure 10B:
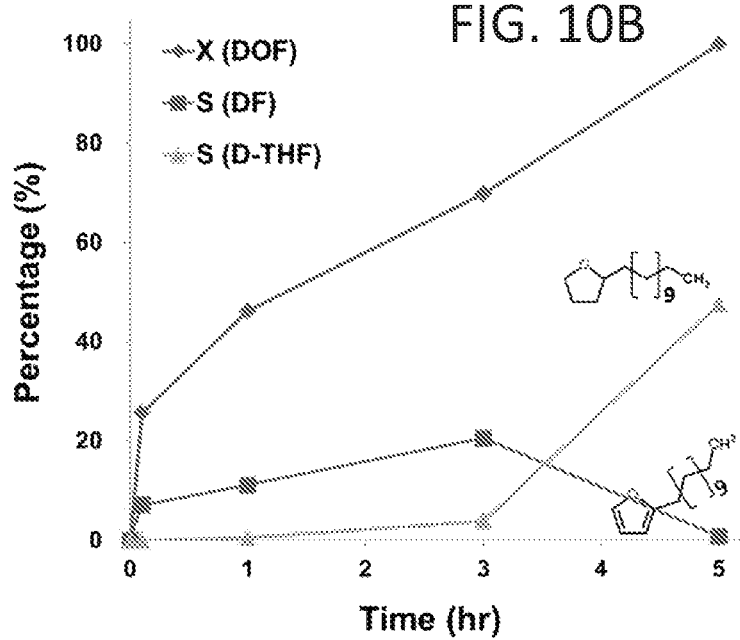

*Reaction Conditions: 220° C., pressures of $H_2$ (at 220° C.), 0.0077 mols of 2-dodecanoylfuran in hexane (30 mL), copper chromite 0.5 g, 5 hrs Non-reduced copper chromite was a more selective catalyst for producing 2-dodecfylfuran (DF). The selectivity of DF was enhanced with decreasing pressure of hydrogen, reaching up to 91% in 100 psi of $H_2$. On the other hand, the selectivity to D-THF increased at 350 psi of $H_2$. In both the high and low-pressure system, the conversion of DOF approached 100%. However, the selectivity to DF decreased after 3.0 hr in 350 psi of $H_2$, and the consumed 2-dodecylfuran was increasingly converted to D-THF by further hydrogenation of the furan ring (FIGS. 10A and 10B).

Figure 11:
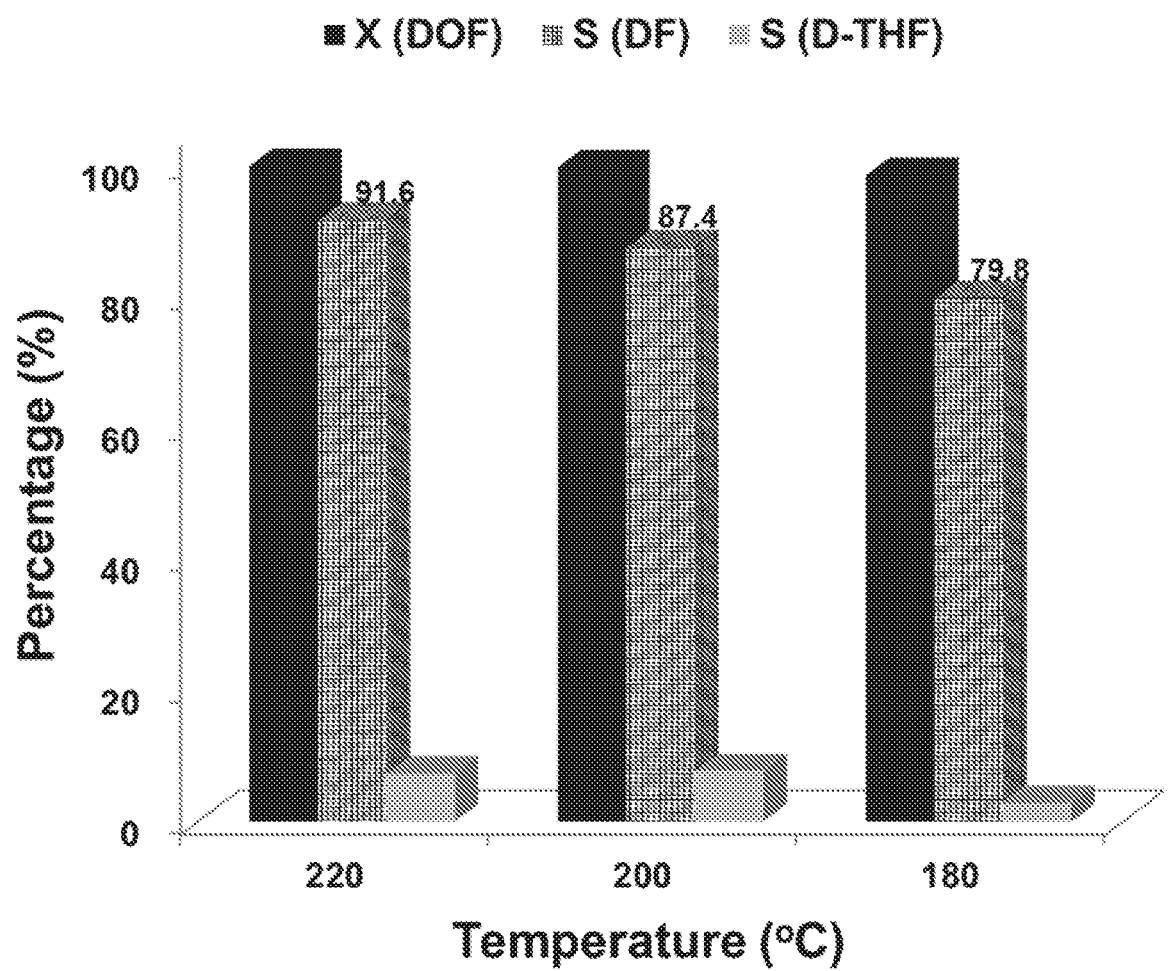
FIG. 11 shows results for the hydrogenation of 2-dodecanoylfuran at 180-220° C. in 100 psi of $H_2$ (Reaction Conditions: 100 psi of $H_2$ (at reaction temperature), 0.0077 mols of 2-dodecanoylfuran in hexane (30 mL), copper chromite 0.5 g, 5 hrs).
Figure 12:
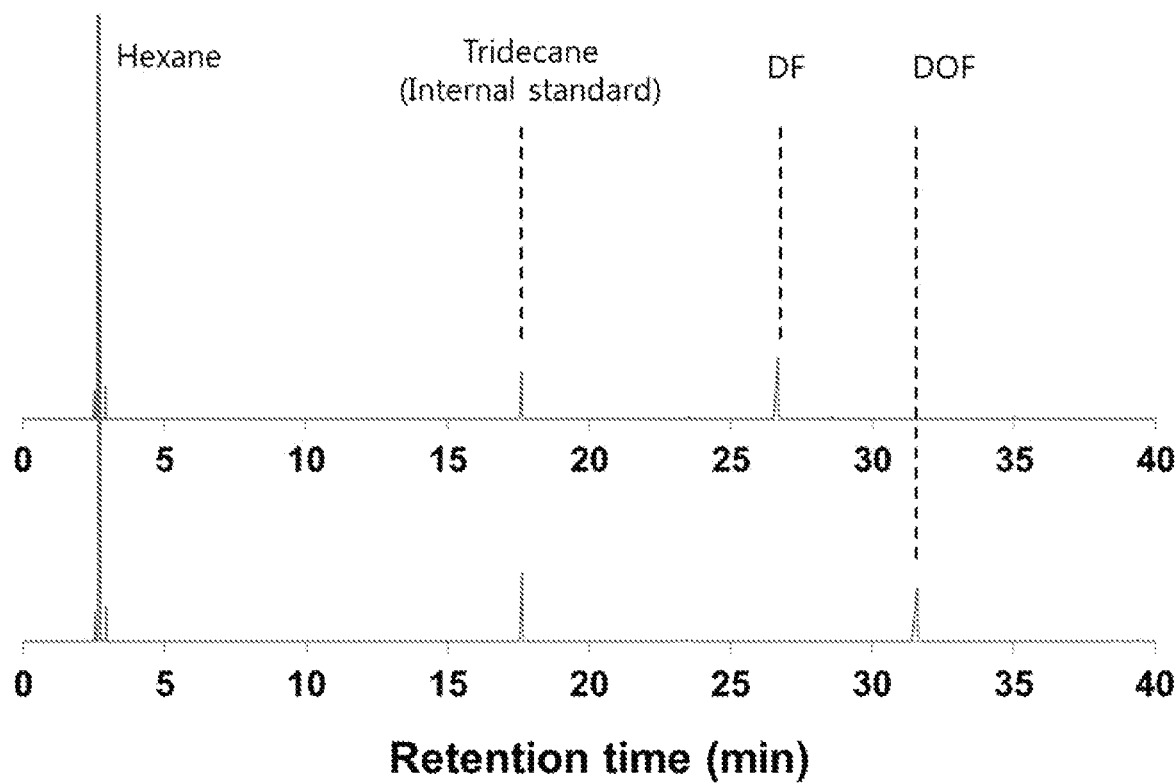
FIG. 12 shows typical GC chromatograms of reactant mixtures (bottom trace) and the products after hydrogenation of 2-dodecanoylfuran (top trace).

The optimum temperature to maximize the selectivity toward production of DF was also investigated. Interestingly, when the temperature was lowered from 220 to 180° C., the selectivity to DF and D-THF also decreased (FIG. 11). To improve selectivity toward 2-dodecylfuran via removal of the ketone from 2-dodecanoylfuran, temperatures above 220° C. are required in addition to moderate hydrogen pressure below 100 psi to prevent hydrogenation of the furan rings. Comparison of the gas chromatograms of the reactant sample (bottom trace) with the products after 5 hrs of reaction (top trace) is represented in FIG. 12, and the desired product, 2-dodecylfuran was identified by GC-MS. (GC MS (EI) m\z (relative intensity): 236 (17.7), 123 (17.6), 96 (12.1), 95 (58.3), 94 (13.5), 82 (42.6), 81 (99.9), 53 (10.1), 43 (10.2), 41 (12.3)).

Illustrative Synthesis of Aromatic Surfactants

Procedure for Preparation of OFS-n-1/O (n=12, 14, 18, and Mixtures from C8 to C18)

Scheme 9 shows an illustrative reaction pathway for furan acylation with fatty acid promoted by trifluoroacetic anhydride at room temperature (TFAA: Trifluoroacetic anhydride, TFA: Trifluoroacetic acid).

Scheme 9: Reaction pathway for furan acylation with fatty acid.

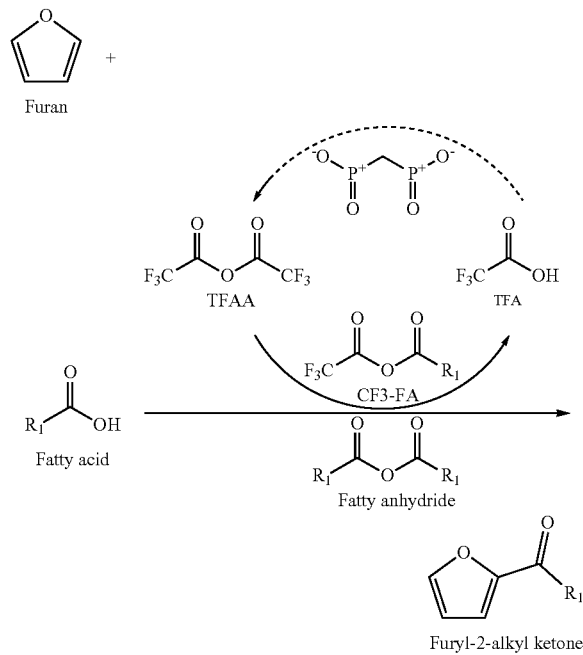

Furan acylation with fatty acids for production of OFS-n-1/O was conducted in a high pressure Parr Reactor and glass beaker. In a typical reaction, the furan (0.014 mol), fatty acid (0.014 mol), trifluoroacetic anhydride (0.02 mol) and n-tridecane (internal standard, 0.002 mol) were dissolved in hexane (10 mL), and 0.2 g of the Al-BEA catalyst was introduced to the mixture. Furan acylation with fatty anhydride was also performed in a Parr reactor with 0.014 mol of furan and 0.0014 mol of fatty anhydride in 15 mL of hexane with Brønsted acid and Lewis acid zeolites such as Al-BEA, Al-MWW, Al-SPP, Sn-BEA, Sn-MWW and Sn-SPP. The sealed reactor was purged with $N_2$ twice to remove the residual air in the reactor. The reactor was then heated to the reaction temperature (room temperature or 50-180° C.) under vigorous stirring (1,000 rpm). The reactor was then pressurized to 200 psi (at desired temperature) with $N_2$ to keep the reactants in liquid phase. After the desired reaction time, the reactor was cooled to room temperature and the gases were vented. The products were identified by a GC-MS (Agilent 7890A connected with Triple-Axis MS detector, Agilent 5975C) and quantified by a GC (Agilent 7890A) equipped with a HP-5 column and a flame ionization detector. The selectivity of the furyl-2-alkyl ketone was calculated by dividing the produced moles of furyl-2-alkyl ketone with the reacted moles of the furan.

Table 16 below provides the results for the actylation of furan with lauric acid and trifluoroacetic anhydride (TFAA).

TABLE 16

| Conditions | Conversion (%) Furan | Conversion (%) Lauric acid | TFAA | Selectivity (%) 2-dodecanoyl-furan |
|---|---|---|---|---|
| 25° C. (No Cat.) | 100 | 100 | 51.1 | 87.0 |
| 25° C. | 100 | 100 | 71.6 | 81.3 |
| 50° C. | 100 | 100 | 70.2 | 75.6 |
| 100° C. | 100 | 100 | 27.4 | 27.4 |
| 150° C. | 100 | 100 | 95.6 | 100 | 43.9 |
| 180° C. | 100 | 78.3 | 100 | 13.5 |
| 150° C. (THF) | 53.9 | 91.2 | 100 | 20.1 |

*Reaction Conditions: 200 psi ($N_2$), 0.014 mol of furan, 0.018 mol of lauric acid, and 0.028 mol of TFAA in hexane (10 mL), Al-BEA 0.2 g, 6 h in Parr reactor.

Figure 13A:
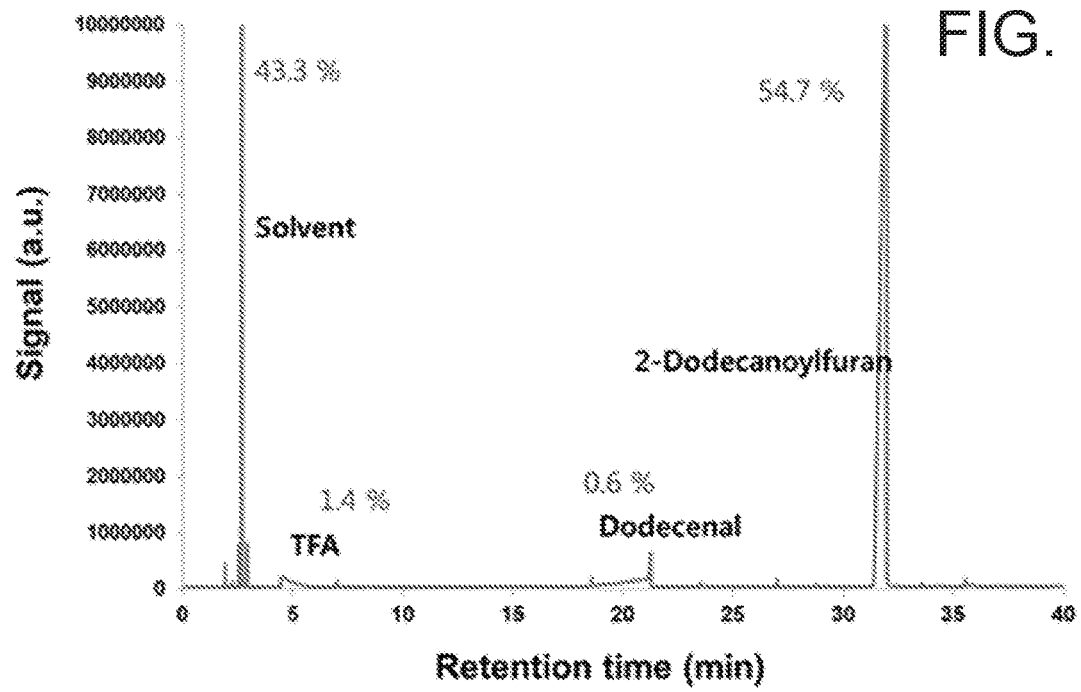
FIGS. 13A and 13B show a typical gas chromatogram (GC) profiles of a product mixture after acylation (FIG. 13A) and post purification by rotary evaporator (FIG. 13B) for 2-dodecanoylfuran.
Figure 13B:
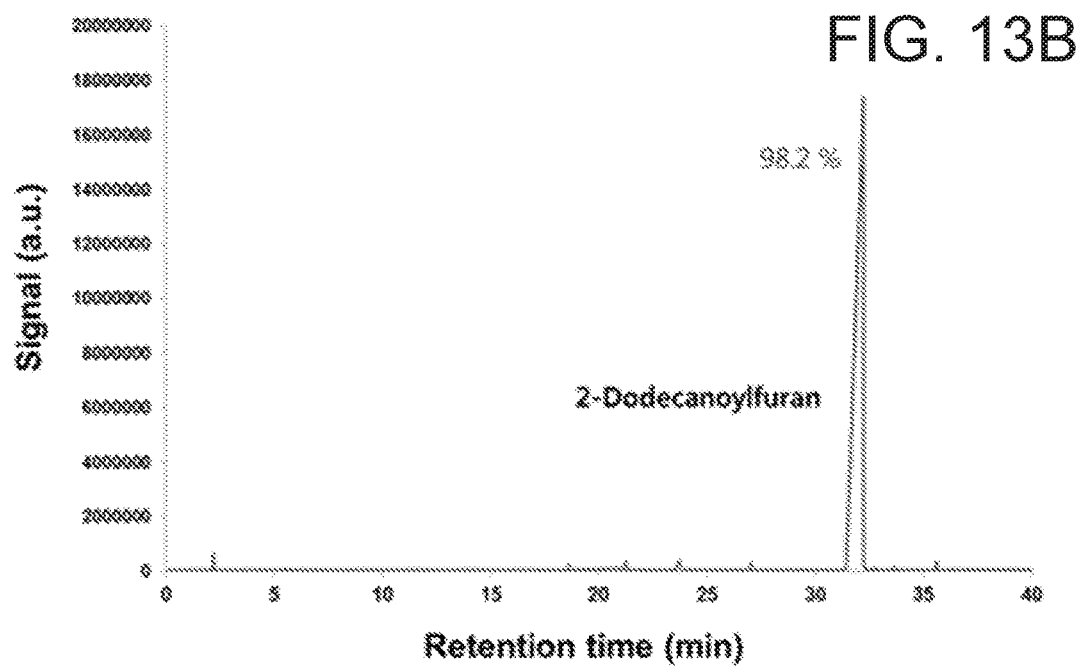

FIGS. 13A and 13B show a typical gas chromatogram (GC) profiles of a product mixture after acylation (FIG. 13A) and post purification by rotary evaporator (FIG. 13B) for 2-dodecanoylfuran; FIGS. 13C, 13D and 13E show the change in the yield of 2-dodecanoylfuran (FIG. 13C); lauric acid concentration (FIG. 13D) during a reaction. Reaction Conditions: 200 psi ($N_2$), 0.014 mol of furan, 0.018 mol of lauric acid, and 0.028 mol of TFAA in hexane (10 mL), Al-BEA 0.2 g, 6 h. FIG. 13E shows results for the acylation of furan and lauric acid with different mole ratios of reactants. LA: Lauric acid, TFAA: Trifluoroacetic anhydride, Mole ratio (1/1.3/1): 0.014 mol of furan/0.018 mol of lauric acid/0.014 mol of TFAA, Reaction conditions: Room temperature, 1 atm, no catalyst. FIG. 13F shows the reaction progression of acylation of furan with lauric acid using TFAA with time. The reaction is complete and high yields are obtained within a few minutes. 0 s corresponds to the point of addition of TFAA. FIG. 13G shows the conversion and selectivity with lauric anhydride over various solid acid catalysts. FIG. 13H shows yield in furan acylation with lauric anhydride over various solid acid catalysts (Reaction conditions: 180° C., 200 psi of $N_2$, 5 h, 0.014 mol of furan, 0.014 mol of lauric anhydride in 15 mL hexane).

The final surfactant OFS-n-1/O was prepared according to the method given below for sulfonation.

Procedure for Preparation of OFS-n (n=12, 14, 18, and Mixtures from C8 to C18)

The reaction pathway for liquid-phase hydrogenation of furyl-2-alkyl ketone over copper chromite ($2CuO-Cr_2O_3$) is shown in Scheme 10 below.

Scheme 10

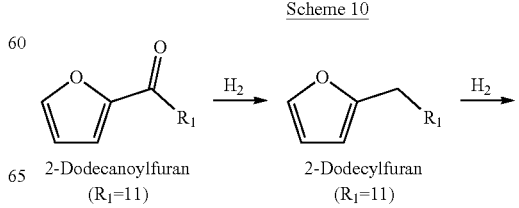

2-Dodecanoylfuran ($R_1$=11)

2-Dodecylfuran ($R_1$=11)

-continued

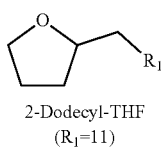

2-Dodecyl-THF
($R_1$=11)

The hydrogenation of OFS-n-1/O to make OFS-n was carried out in a 100 mL Parr reactor. The prepared furyl-2-alkyl ketone (2 mL) and n-tridecane (internal standard, 0.5 mL) were dissolved in hexane (30 mL), and 0.5 g of copper chromite catalyst was introduced to the mixture. The reactor was pressurized with hydrogen in a range of 100-350 psi at the desired reaction temperature (180-220° C.). The selectivity of the 2-n-alkylfuran was calculated by dividing the produced moles of 2-n-alkylfuran with the reacted moles of the furyl-2-alkyl ketone. The final surfactant OFS-n was prepared according to the method given below for sulfonation.

Table 17 below shows the results for the hydrogenation of 2-dodecanoylfuran over copper chromite.

TABLE 17

| Conditions | Conversion (%) | | Selectivity (%) | | |
|---|---|---|---|---|---|
| | 2-dodecanoyl-furan | 2-dodecyl-furan | 2-dodecyl-THF | Unknown | |
| 100 psi | 100 | 91.6 | 7.3 | 1.1 | |
| 150 psi | 100 | 59.5 | 12.3 | 28.2 | |
| 250 psi | 100 | 54.8 | 18.3 | 26.9 | |
| 350 psi | 100 | 0.9 | 47.6 | 51.5 | |
| 250 psi (Reduced 2CuO-$Cr_2O_3$) | 99.6 | 18.3 | 74.9 | 6.9 | |

*Reaction Conditions: 220° C., varying pressures of $H_2$ (at 220° C.), 0.0077 mol of 2-dodecanoylfuran in hexane (30 mL), copper chromite 0.5 g, 5 h.

Figure 14C:
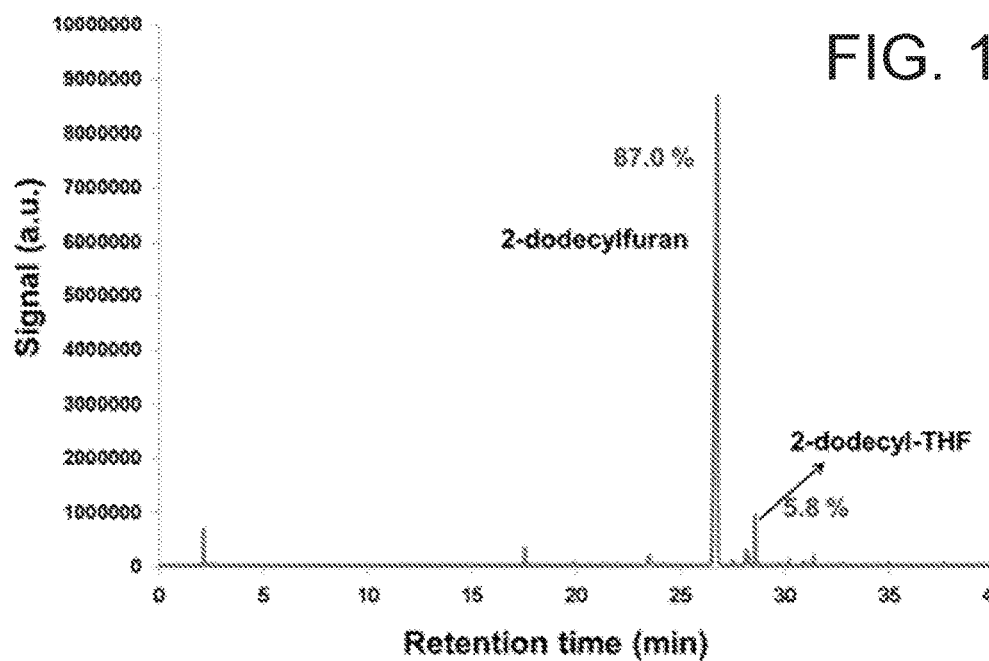
FIGS. 14C and 14D show tyripcal GC profiles of product mixtures after hydrogenation—concentrated samples by rotary evaportor (FIG. 14C) and purified and separated by flash chromatography (FIG. 14D)
Figure 14D:
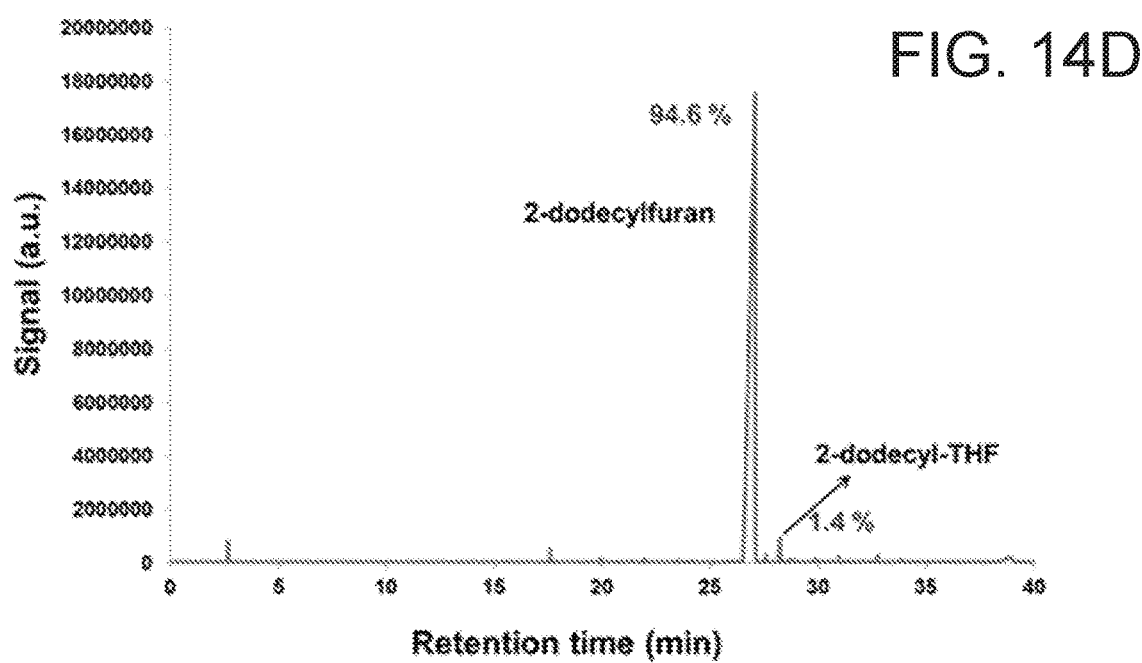
Figure 14E:
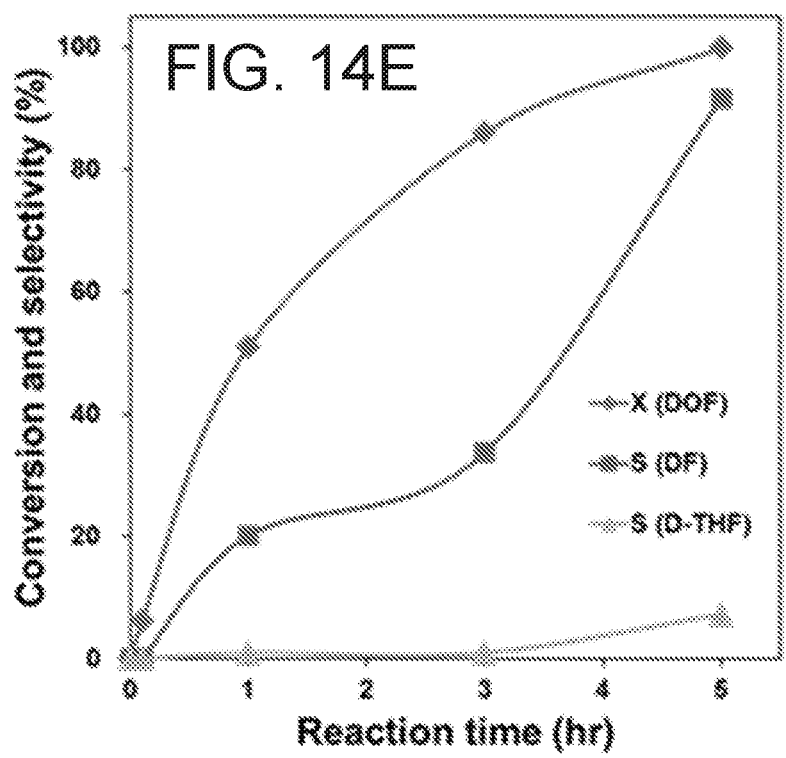
FIGS. 14E and 14F show time-on-stream results (conversion of 2-dodecanoylfuran (DOF) and selectivities of 2-dodecylfuran (DF) and 2-dodecyl-tetrahydrofuran (D-THF)) for the hydrogenation of 2-dodecanoylfuran at 100 psi (FIG. 14E) and 350 psi of $H_2$ (FIG. 14F).
Figure 14F:
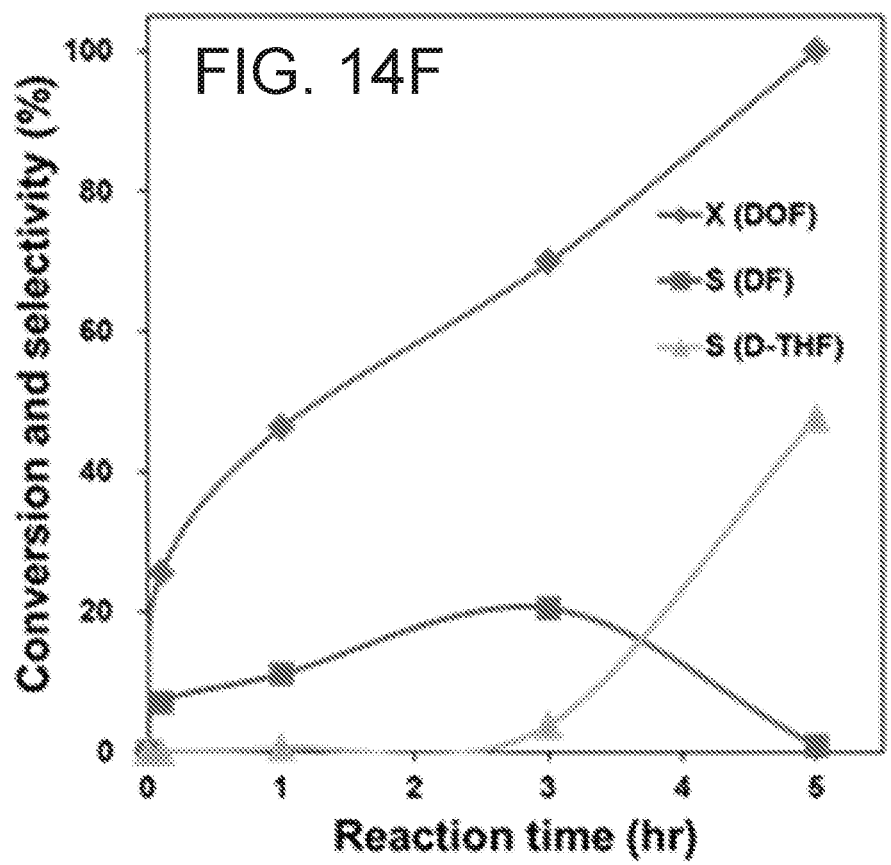
Figure 14G:
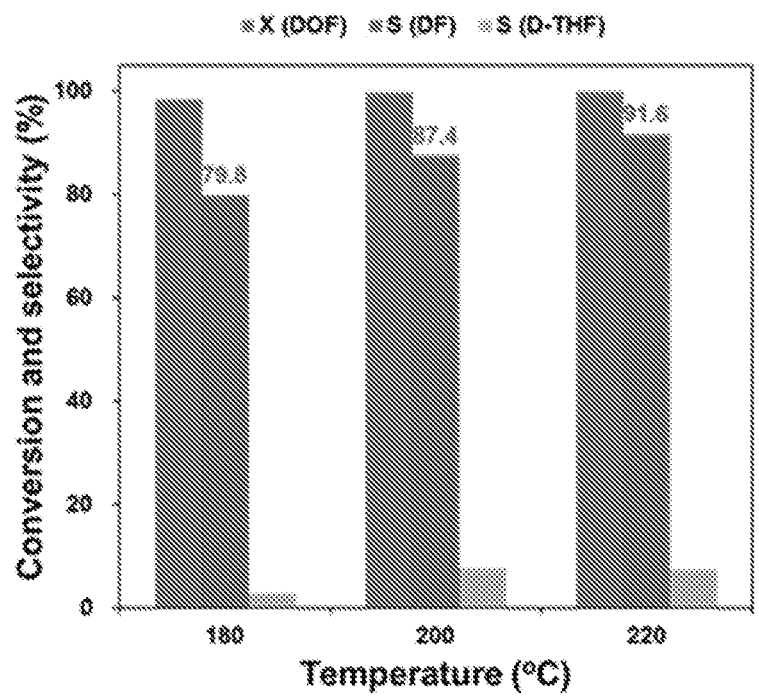
FIG. 14G shows results for the hydrogenation of 2-dodecanoylfuran (DOF) at 180-220° C. in 100 psi of $H_2$. Reaction Conditions: 100 psi of $H_2$ (at reaction temperature), 0.0077 mol of 2-dodecanoylfuran in hexane (30 mL), copper chromite 0.5 g, 5 h.

FIGS. 14A and 14B show typical GC profiles of a reactant mixture (FIG. 14A) and products in hydrogenation of 2-dodecanoylfurant (DOF: 2-dodecanoylfuran, DF: 2-dodecylfuran). FIGS. 14C and 14D show typical GC profiles of product mixtures after hydrogenation—concentrated samples by rotary evaportor (FIG. 14C) and purified and separated by flash chromatography (FIG. 14D). FIGS. 14E and 14F show time-on-stream results (conversion of 2-dodecanoylfuran (DOF) and selectivities of 2-dodecylfuran (DF) and 2-dodecyl-tetrahydrofuran (D-THF)) for the hydrogenation of 2-dodecanoylfuran at 100 psi (FIG. 14E) and 350 psi of $H_2$ (FIG. 14F). FIG. 14G shows results for the hydrogenation of 2-dodecanoylfuran (DOF) at 180-220° C. in 100 psi of $H_2$. Reaction Conditions: 100 psi of $H_2$ (at reaction temperature), 0.0077 mol of 2-dodecanoylfuran in hexane (30 mL), copper chromite 0.5 g, 5 h.

Procedure for Preparation of OFS-12-2/C2H5

For making the mono-ethyl branched surfactant monomer (M-DF, Scheme 11), aldol-condensation of furyl-2-dodecyl ketone (2-dodecanoylfuran, DOF) with acetaldehyde was conducted in a 100 mL Parr reactor. The prepared DOF (0.0054-0.01 moles) and acetaldehyde (0.0054-0.054 moles) were dissolved in hexane (20 mL), and 0.2 g of solid acid/base catalysts was introduced to the mixture. The reactor was pressurized to 200 psi with $N_2$ to prevent vaporization of acetaldehyde and heated to 180-220° C. After purification of the aldol-condensation products, the mixture of unreacted DOF and aldol-product (Al_DOF) was used as the reactant for hydrogenation. The reduction of ketone to the hydrocarbon via hydrogenation was carried out at 220° C. and 100 psi of $H_2$ for 7 h using copper chromite as the catalyst to produce M-DF (Scheme 8). The final surfactant OFS-12/C2H5 was prepared according to the method given below for sulfonation.

Scheme 11. Reaction pathways for aldol condensation of 2-dodecanoylfuran (DOF) with acetaldehyde and dehydrogenation of the aldol-product (Al_DOF) to form mono-ethyl branched dodecylfuran (M-DF). One of the side products of the reaction is M-DTHF (mono-ethyl branched dodecyl-tetrahydrofuran) formed due to undesirable hydrogenation of the furan ring.

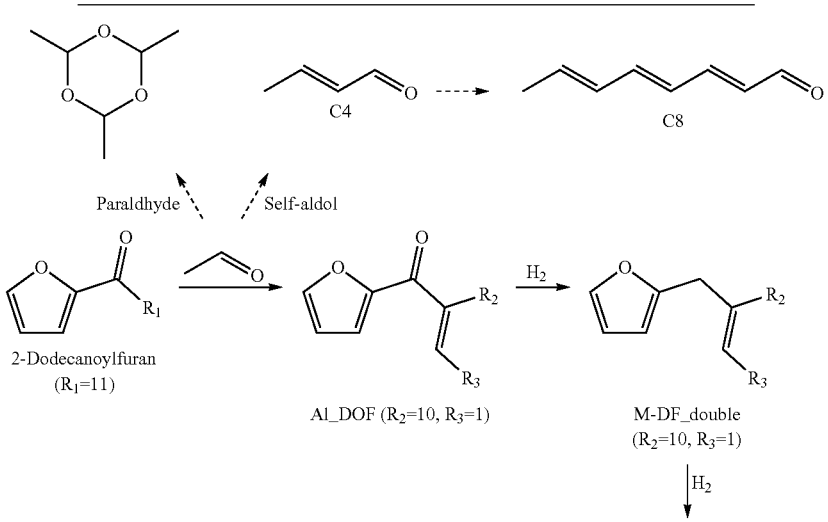

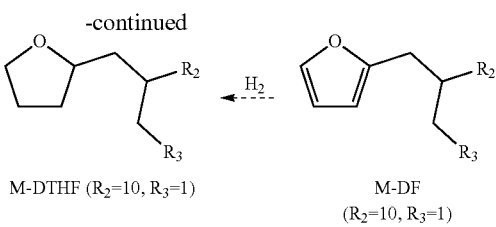

M-DTHF (R₂=10, R₃=1)     M-DF (R₂=10, R₃=1)

Tables 18, 19 and 20 below shows the results of the aldol condensation using various acid and base catalysts.

TABLE 18

Summarized results for the aldol condensation of 2-dodecanoylfuran (DOF) with acetaldehyde over various acid and base catalysts.

| Conditions | Conversion (%) | | Selectivity (%) | | | | Yield (%) Al_DOF |
|---|---|---|---|---|---|---|---|
| | Acetaldehyde | DOF | C4 | C8 | Paraldehyde | Al_DOF | |
| Al-BEA (200° C., 6 h) | 74.7 | 17.2 | 4.6 | 1.2 | 0.05 | 47.2 | 8.1 |
| KBEA (200° C., 6 h) | 62.3 | 12.0 | 9.5 | 1.3 | 0.03 | 75.5 | 9.1 |
| HY (200° C., 6 h) | 73.5 | 17.4 | 10.2 | 1.4 | 0.04 | 58.1 | 10.1 |
| Mg—Zr—O (200° C., 6 h) | 99.5 | 12.3 | 0.08 | 0.9 | 0.01 | 9.0 | 1.1 |
| HY (220° C., 6 h) | 78.8 | 17.6 | 8.5 | 1.4 | 0.02 | 42.5 | 7.5 |
| HY (180° C., 6 h) | 73.7 | 13.8 | 8.3 | 0.7 | 0.06 | 80.9 | 11.2 |
| KY (180° C., 6 h) | 72.1 | 16.2 | 10.5 | 0.8 | 0.03 | 63.0 | 10.2 |
| HY (180° C., 24 h) | 85.2 | 34.7 | 7.1 | 1.7 | 0.02 | 58.5 | 20.3 |
| HY (180° C., 48 h) | 93.9 | 47.2 | 7.7 | 18.7 | 0.04 | 35.6 | 16.6 |

*Reaction Conditions: 200 psi (N₂), 0.054 mol of acetaldehyde and 0.0054 mol of 2-dodecanoylfuran in hexane (20 mL), 0.2 g catalyst.

TABLE 19

Summarized results for the aldol condensation of 2-dodecanoylfuran (DOF) with acetaldehyde over various acid and base catalysts.

| Catalysts | Conversion (%) | | Selectivity (%) | | | | Yield (%) Al_DOF |
|---|---|---|---|---|---|---|---|
| | Acetaldehyde | DOF | C4 | C8 | Paraldehyde | Al_DOF | |
| HY (1 g, 24 h) | 93.0 | 19.4 | 5.3 | 1.3 | 0.02 | 41.5 | 8.1 |
| HY (0.2 g, 24 h) | 85.2 | 34.7 | 7.1 | 1.7 | 0.02 | 58.5 | 20.3 |
| HY (0.1 g, 24 h) | 74.0 | 29.6 | 11.3 | 2.4 | 0.6 | 62.6 | 18.5 |
| Si-SPP (0.1 g, 24 h) | 82.0 | 27.4 | 8.1 | 3.5 | 0.06 | 63.3 | 17.3 |
| Al-SPP (0.1 g, 24 h) | 81.5 | 17.6 | 11.2 | 9.4 | 0.06 | 78.3 | 13.8 |
| Al-MWW (0.1 g, 24 h) | 90 | 20.6 | 3.8 | 3.2 | 0.05 | 70.9 | 14.6 |
| NaOH (0.1 g, 24 h) | 99 | 22.3 | 0.06 | 0.2 | 0.3 | 1.7 | 0.4 |
| No Cat. (24 h) | 72.3 | 33.0 | 7.8 | 1.1 | 0.2 | 70.8 | 23.4 |
| No Cat. (48 h) | 87.5 | 36.8 | 7.8 | 0.9 | 0.1 | 60.0 | 22.1 |
| No Cat. (72 h) | 93.1 | 58.3 | 4.1 | 0.6 | 0.04 | 24.5 | 14.3 |

*Reaction Conditions: 200 psi (N₂), 180° C., 0.054 mol of acetaldehyde and 0.0054 mol of 2-dodecanoylfuran in hexane (20 mL).

TABLE 20

Summarized results for the aldol condensation of 2-dodecanoylfuran (DOF) with acetaldehyde.

| Mole ratio of reactants (AA:DOF) | Conversion (%) | | Selectivity (%) | | | | Yield (%) Al_DOF |
|---|---|---|---|---|---|---|---|
| | Acetaldehyde | DOF | C4 | C8 | Paraldehyde | Al_DOF | |
| 15:1 | 60.4 | 32.6 | 16.2 | 2.0 | 0.5 | 67.1 | 21.9 |
| 10:1 | 72.3 | 33.0 | 7.8 | 1.1 | 0.2 | 70.8 | 23.4 |

TABLE 20-continued

Summarized results for the aldol condensation of 2-dodecanoylfuran (DOF) with acetaldehyde.

| Mole ratio of reactants (AA:DOF) | Conversion (%) | | Selectivity (%) | | | | Yield (%) |
|---|---|---|---|---|---|---|---|
| | Acetaldehyde | DOF | C4 | C8 | Paraldehyde | Al_DOF | Al_DOF |
| 5:1 | 72.8 | 17.0 | 7.9 | 0.5 | 0.2 | 70.9 | 12.1 |
| 1:1 | 70.0 | 4.0 | 1.4 | 0 | 0 | 57.2 | 2.3 |
| 1:2 | 82.7 | 11.1 | 0.9 | 0 | 0 | 61.2 | 6.8 |

*Reaction Conditions: 200 psi ($N_2$), 180° C., 24 h, (10:1) ratio: 0.054 mol of acetaldehyde and 0.0054 mol of 2-dodecanoylfuran in hexane (20 mL).

Figure 15A:
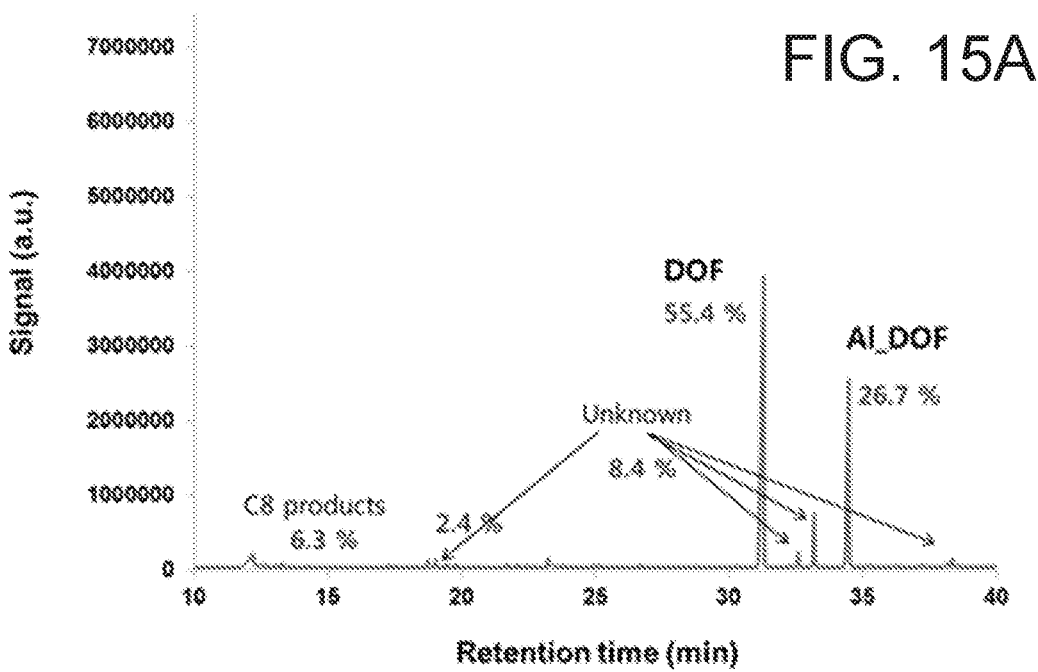

FIGS. 15A and 15B show typical GC profiles of product mixtures after aldol condensation—concentrated samples by rotary evaporator (FIG. 15A) and purified and separated by flash chromatography (FIG. 15B).

Separation of Furyl-2-Alkyl Ketone (Alkyl Chain=C12, C14, C18, and C8-C18 Mixture)

The acylation products were concentrated using a rotary evaporator (Hei-VAP/G5, Heidolph) with a liquid nitrogen condenser. Several batch reactions were conducted without the internal standard chemical (n-tridecane) to collect the product mixture. The rotary evaporator was operated at room temperature for 30 min under high vacuum to remove the light molecules (hexane, furan, trifluoroacetic anhydride and trifluoroacetic acid). The remaining mixture was further concentrated at 70° C. for 2 h under high vacuum.

Separation and Purification of 2-n-Alkylfuran (Alkyl Chain=C12, C14, C18, and C8-C18 Mixture) and M-DF The products after hydrogenation were purified by using rotary evaporator initially followed by flash chromatography. The rotary evaporator was operated at 50° C. for 1 h to evaporate the solvent and light molecules. Further purification was done by flash chromatography using a 12 inch length and 1 inch diameter column (CG-1189-07) packed with silica gel (230-400 mesh, particle size 40-63 μm). Hexane was used as the mobile phase to separate 2-n-dodecylfuran (DF) and M-DF (Scheme 5) from the product mixture, and a 50% acetone in hexane solution was used as the eluent to remove undesired products (eg. saturation of furan ring to form tetrahydrofuran based molecules such as M-DTHF as shown in Scheme 5 and some other unknown compounds).

Separation and Purification of the Aldol-Condensation Product (Al_DOF)

After aldol-condensation, the products, unreacted DOF and aldol-product, were concentrated and purified using rotary evaporator and flash chromatography. The rotary evaporator aided in the removal of all solvent and light molecules while, flash chromatography was used with a 1 inch diameter glass column, and 1,2-dichloroethane as the eluent to separate the desired products (DOF and Al_DOF) from all unknown chemicals.

During the process of separation and purification, the ratio of unreacted DOF to the aldol product (Al_DOF) changed from 77:23 to 70:30 due to losses during flash chromatography. Post hydrogenation, this ratio (DF:M-DF) changed to 66:34 which further reduced to 60:40 post purification.

FIGS. 15C and 15D show typical GC profiles of a reactant mixture (FIG. 15C) and products (FIG. 15D) in the hydrogenation of DOF and Al_DOF (DOF: 2-dodecanoylfuran, Al_DOF: aldol product, DF: 2-dodecylfuran, M-DF: monoethyl branched dodecylfuran).

Sulfonation

All prepared surfactant monomers (including reference standards such as 2-n-heptylfuran) were sulfonated and neutralized to make oleo-furan sulfonate surfactants (OFS-n, OFS-n-1/O, OFS-n-2/2H5), sodium 2-R-furan-5-sulfonate (R=different alkyl chains), by the following method. The synthesized monomers (13 mmol) were added to a slurry of sulfur trioxide-pyridine complex (13 mmol) in anhydrous acetonitrile (12 mL). The mixture was stirred at room temperature for 3 days. At the end of 72 h, 40 mL of water (70° C.) was introduced to the slurry, and the slurry was stirred for 1 h. The aqueous phase was separated by a separatory funnel after 1 h, and the aqueous solution was neutralized by using sodium carbonate till the pH was 7.0. The water was then evaporated off and the crystalline phase was collected by filtration and washed with iso-propanol (60° C., 50 mL, 5 times) (G. Trummlitz, E. Seeger, W. Engel, "4-5-Dimethyl-thieno[3,2-d]ISO-thiazolo-3(2H)-one-1,1-dioxides, compositions, and methods of use as a sweetener," U.S. Pat. No. 4,233,333, Nov. 11, 1980; and WO 2015084813).

Characterization (NMR, Particle Size Distribution of Micelles via DLS)

NMR

The synthesized surfactant monomers and oleo-furan sulfonate surfactants (OFS-n, OFS-n-1/O, OFS-12-2/C2H5) were analyzed by NMR spectroscopy (Bruker AX400, 400 MHz). The $^1$H and $^{13}$C NMR of the surfactant monomers was performed by dissolving ~20 μL of the compound in $CDCl_3$ containing 5 mM of tetramethylsilane (TMS) as an internal standard. The oleo-furan surfactants were also identified by NMR using DMSO-$d_6$ as the solvent. The results from NMR analysis are given below.

2-Dodecanoylfuran (Furyl-2-Dodecyl-Ketone)

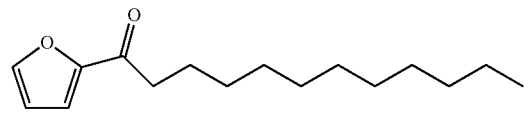 [SMILES: CCCCCCCCCCCC(=O)c1ccco1]

$^1$H-NMR (400 MHz, $CDCl_3$) δ 0.86-0.90 (t, 3H), 1.25 (brm, 16H), 1.67-1.75 (m, 2H), 2.80-2.84 (t, 2H), 6.53-6.54 (q, 1H), 7.20-7.21 (q, 1H), 7.58-7.59 (q, 1H) ppm.

$^{13}$C-NMR (100 MHz, $CDCl_3$) δ 14.11, 22.68, 24.50, 29.32, 29.37, 29.46, 29.60, 31.90, 38.52, 112.27, 117.49, 146.55, 152.69, 190.68 ppm.

GCMS (EI) m/z (relative intensity): 151 (3.4), 123 (20.1), 111 (10.9), 110 (99.9), 95 (31.6), 81 (2.6), 55 (5.5), 43 (4.4), 41 (6.2), 39 (3.6).

Figure 16A:
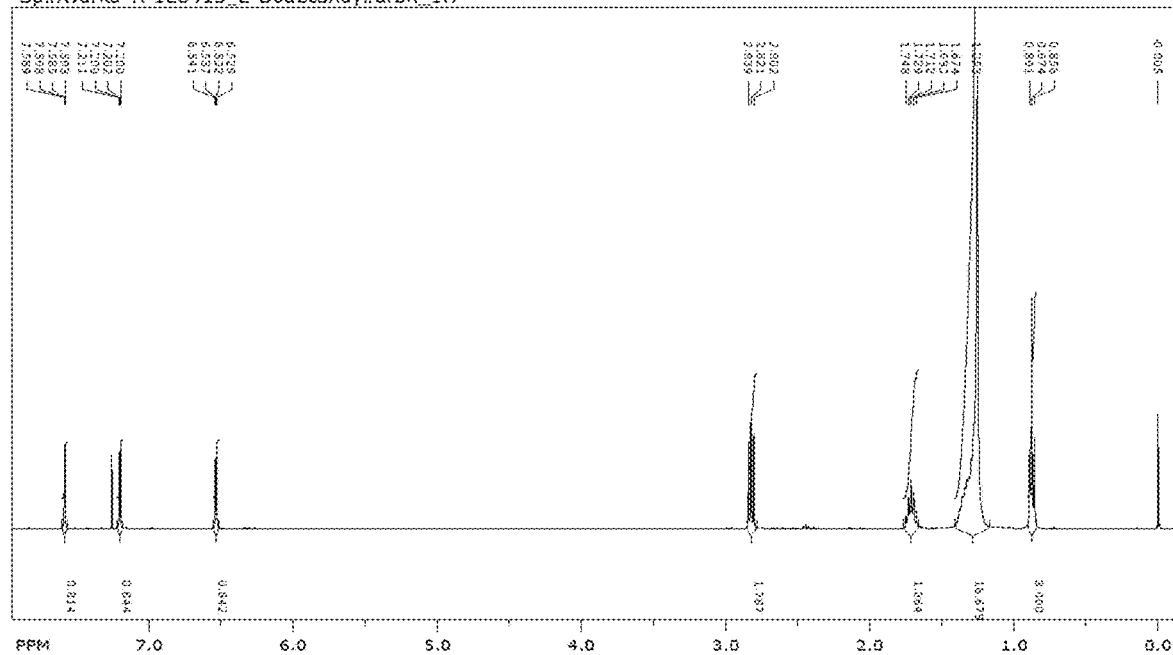
FIGS. 16A and 16B show the $^1$H NMR and $^{13}$C NMR of 2-dodecanoylfuran (furyl-2-dodecyl-ketone) in CDCl$_3$
Figure 16B:
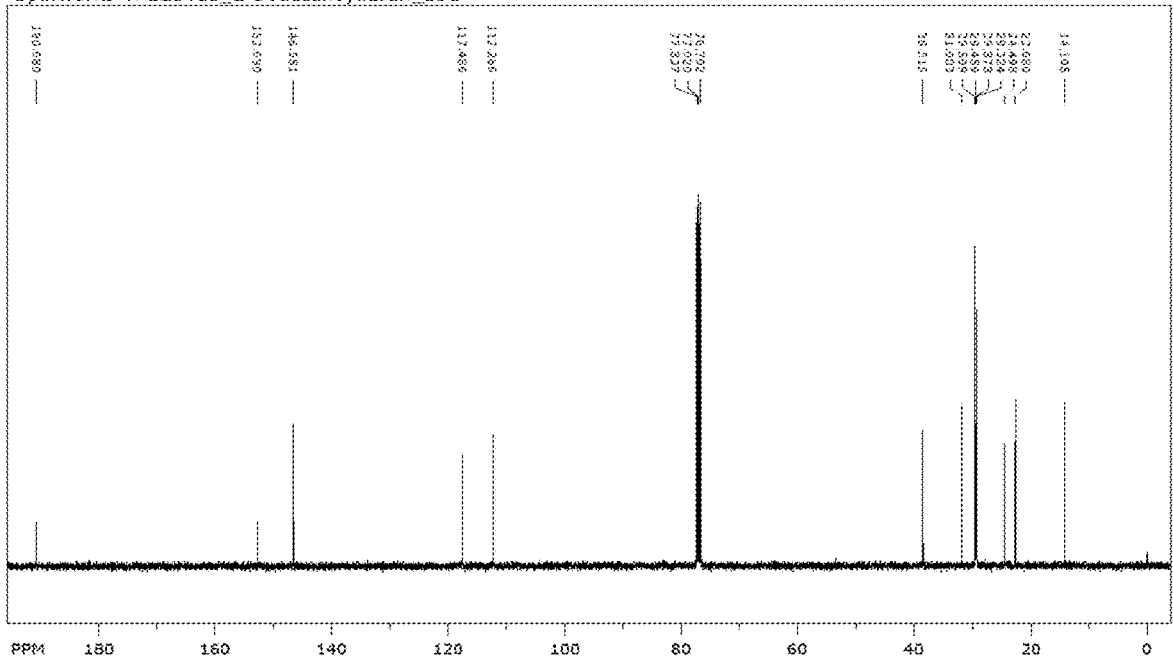

FIGS. 16A and 16B show the $^1$H NMR and $^{13}$C NMR of 2-dodecanoylfuran (furyl-2-dodecyl-ketone) in $CDCl_3$.

2-Tetradecanoylfuran (Furyl-2-Tetradecyl-Ketone)

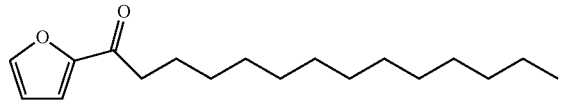 [SMILES: CCCCCCCCCCCCCC(=O)c1ccco1]

$^1$H-NMR (400 MHz, $CDCl_3$) δ 0.86-0.89 (t, 3H), 1.25 (brm, 20H), 1.67-1.75 (m, 2H), 2.78-2.82 (t, 3H), 6.51-6.52 (q, 1H), 7.16-7.17 (q, 1H), 7.56-7.57 (q, 1H)

$^{13}$C-NMR (100 MHz, $CDCl_3$) δ 14.11, 22.69, 24.36, 29.34, 29.40, 29.48, 29.61, 29.65, 29.67, 31.92, 38.54, 112.08, 116.75, 146.13, 152.89, 189.87 ppm GCMS (CI) m/z (relative intensity): 279.2 (100), 43.0 (26.8), 278.4 (19.5), 110.0 (19.5), 280.2 (18.4), 277.5 (13), 135.1 (6.2), 166.1 (4.4), 95.0 (4.4), 123.0 (3.8).

Figure 17A:
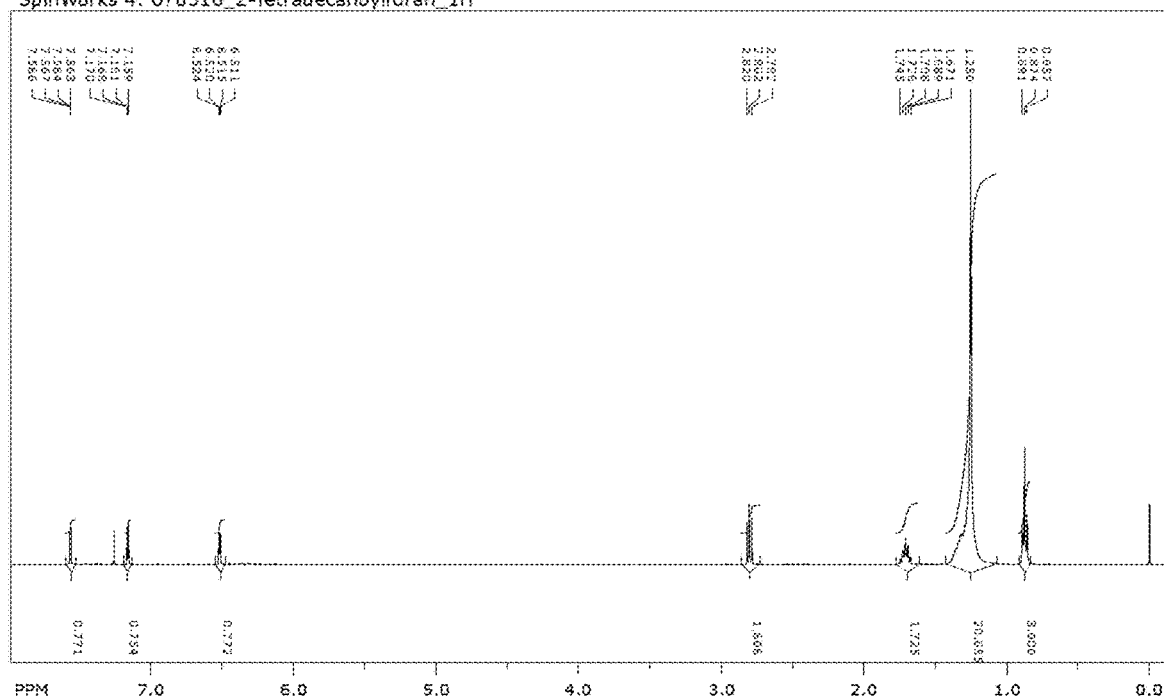
FIGS. 17A and 17B show the $^1$H NMR and $^{13}$C NMR of 2-tetradecanoylfuran (furyl-2-tetradecyl-ketone) in CDCl$_3$.
Figure 17B:
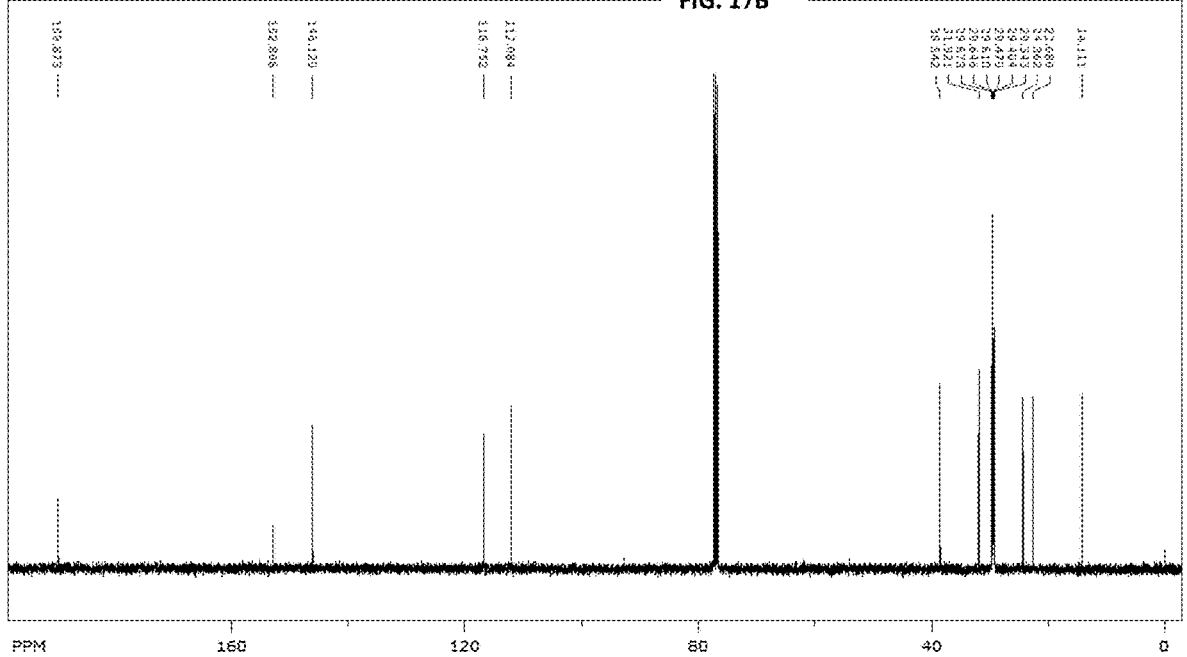

FIGS. 17A and 17B show the $^1$H NMR and $^{13}$C NMR of 2-tetradecanoylfuran (furyl-2-tetradecyl-ketone) in CDCl$_3$.

2-Octadecanoylfuran (Furyl-2-Octadecyl-Ketone)

$^1$H-NMR (400 MHz, CDCl$_3$) δ 0.86-0.90 (t, 3H), 1.26 (brm, 28H), 1.68-1.75 (m, 2H), 2.80-2.84 (t, 2H), 6.53-6.54 (q, 1H), 7.20-7.21 (d, 1H), 7.59 (d, 1H) ppm.

$^{13}$C-NMR (100 MHz, CDCl$_3$) δ 14.11, 22.69, 24.49, 29.33, 29.37, 29.47, 29.61, 29.67, 29.70, 31.93, 38.51, 112.26, 117.48, 146.54, 152.69, 190.67 ppm.

GCMS (CI) m/z (relative intensity): 335.3 (100), 43 (46.8), 334.6 (29.4), 336.3 (23.5), 110.0 (19.4), 333.7 (19.4), 42 (5.4), 135.1 (5.2), 123.0 (4.2).

Figure 18A:
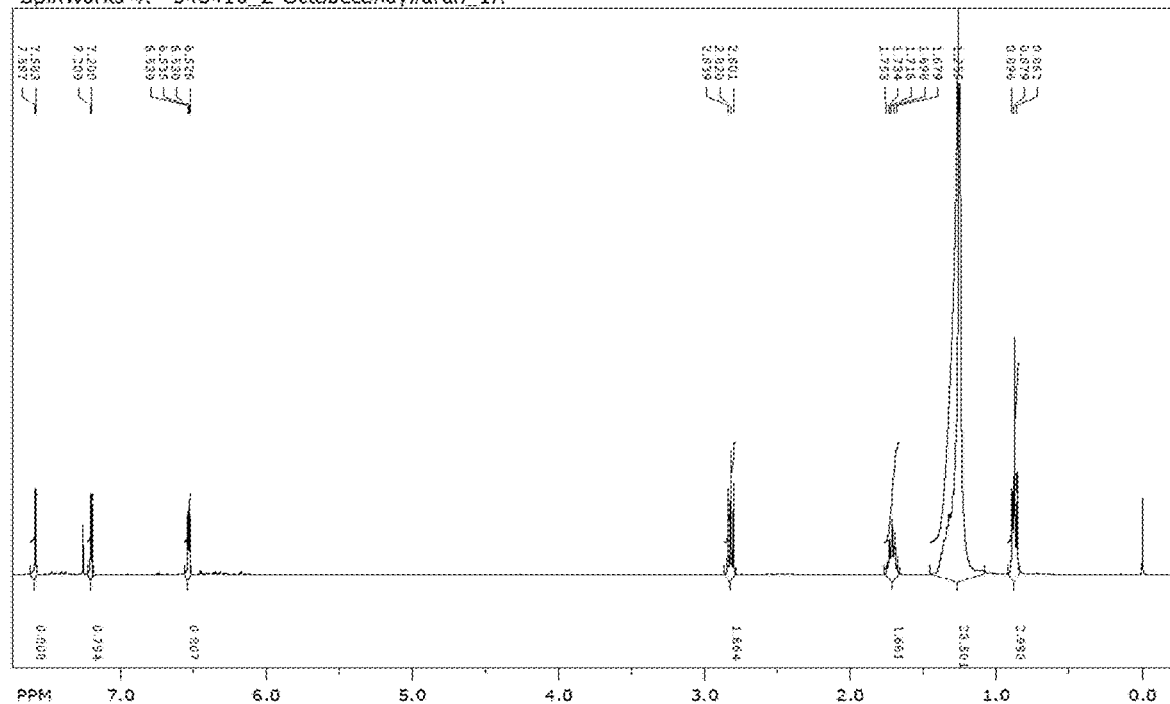
FIGS. 18A and 18B show the $^1$H NMR and $^{13}$C NMR of 2-octadecanoylfuran (furyl-2 octadecyl-ketone) in CDCl$_3$.
Figure 18B:
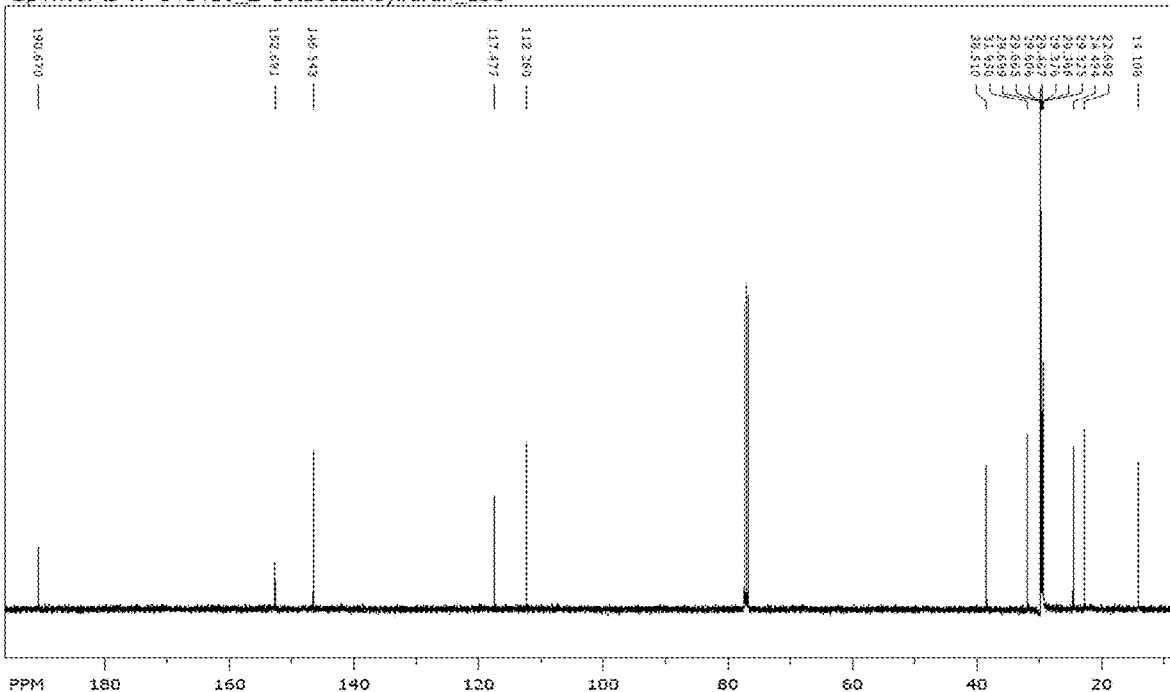

FIGS. 18A and 18B show the $^1$H NMR and $^{13}$C NMR of 2-octadecanoylfuran (furyl-2-octadecyl-ketone) in CDCl$_3$.

2-n-Dodecylfuran $^1$H-NMR (400 MHz, CDCl$_3$) δ 0.87-0.90 (t, 3H), 1.26 (brm, 18H), 1.60-1.67 (m, 2H), 2.59-2.63 (t, 2H), 5.96-5.97 (q, 1H), 6.27-6.28 (q, 1H), 7.29-7.30 (q, 1H) ppm.

$^{13}$C-NMR (100 MHz, CDCl$_3$) δ 14.12, 22.71, 27.99, 28.06, 29.21, 29.37, 29.38, 29.57, 29.65, 29.68, 31.94, 104.50, 110.02, 140.60, 156.66 ppm.

GCMS (EI) m/z (relative intensity): 236 (17.7), 123 (17.6), 96 (12.1), 95 (58.3), 94 (13.5), 82 (42.6), 81 (99.9), 53 (10.1), 43 (10.2), 41 (12.3).

Figure 19A:
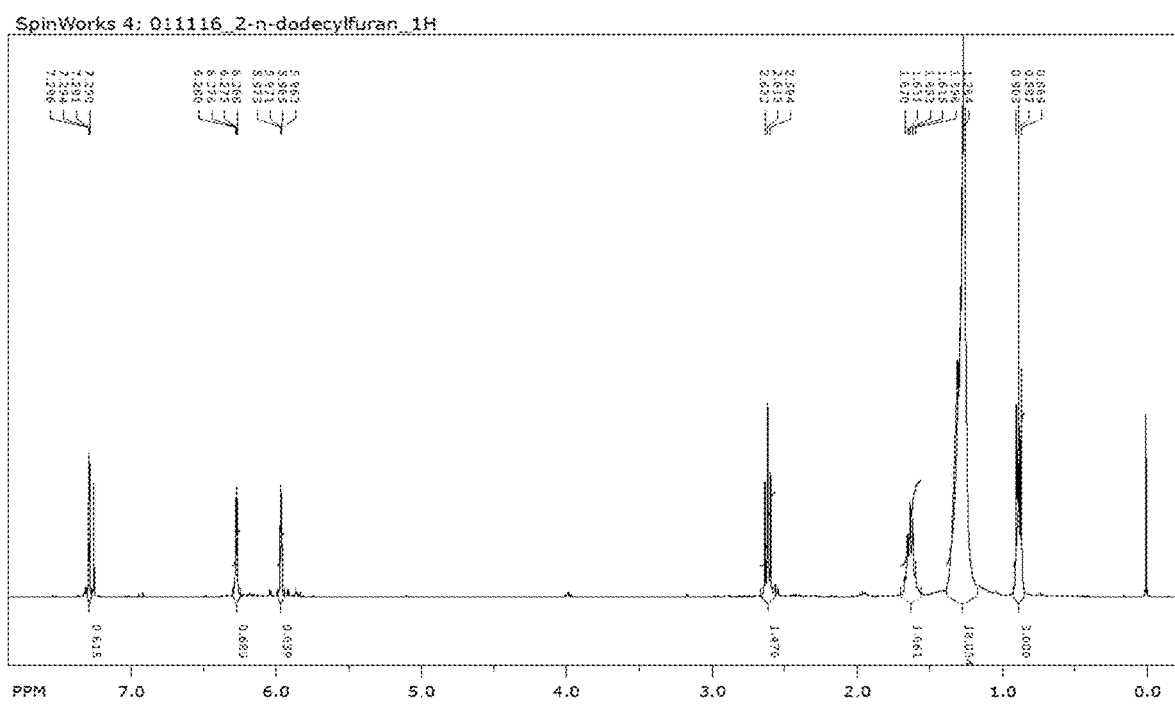
FIGS. 19A and 19B show the $^1$H NMR and $^{13}$C NMR of 2-n-dodecylfuran in CDCl$_3$.
Figure 19B:
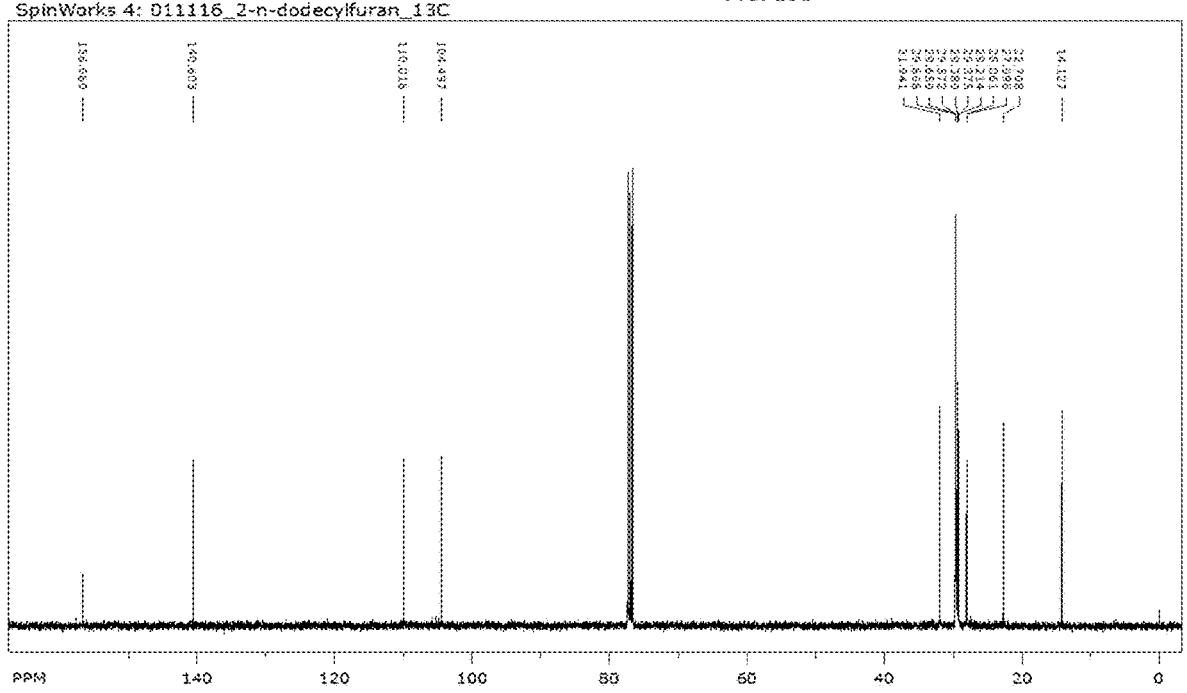

FIGS. 19A and 19B show the $^1$H-NMR and $^{13}$C NMR of 2-n-dodecylfuran in CDCl$_3$.

2-n-Tetradecylfuran $^1$H-NMR (400 MHz, CDCl$_3$) δ 0.87-0.90 (t, 3H), 1.26 (brm, 22H), 1.60-1.67 (m, 2H), 2.59-2.63 (t, 2H), 5.96-5.97 (d, 1H), 6.27-6.28 (q, 1H), 7.29 (d, 1H) ppm.

$^{13}$C-NMR (100 MHz, CDCl$_3$) δ 14.13, 22.71, 28.00, 28.06, 29.21, 29.38, 29.57, 29.66, 29.68, 29.70, 29.71, 31.95, 104.50, 110.02, 140.61, 156.66 ppm.

GCMS (CI) m/z (relative intensity): 265.2 (82.7), 43.0 (100), 81 (99.6), 95.0 (48.4), 263.5 (46), 264.5 (41), 305.4 (34.5), 307.4 (33), 345.2 (23.2), 82.1 (22.5), 266.4 (16), 123.1 (14.3), 42.1 (12), 137.2 (11.8).

Figure 20A:
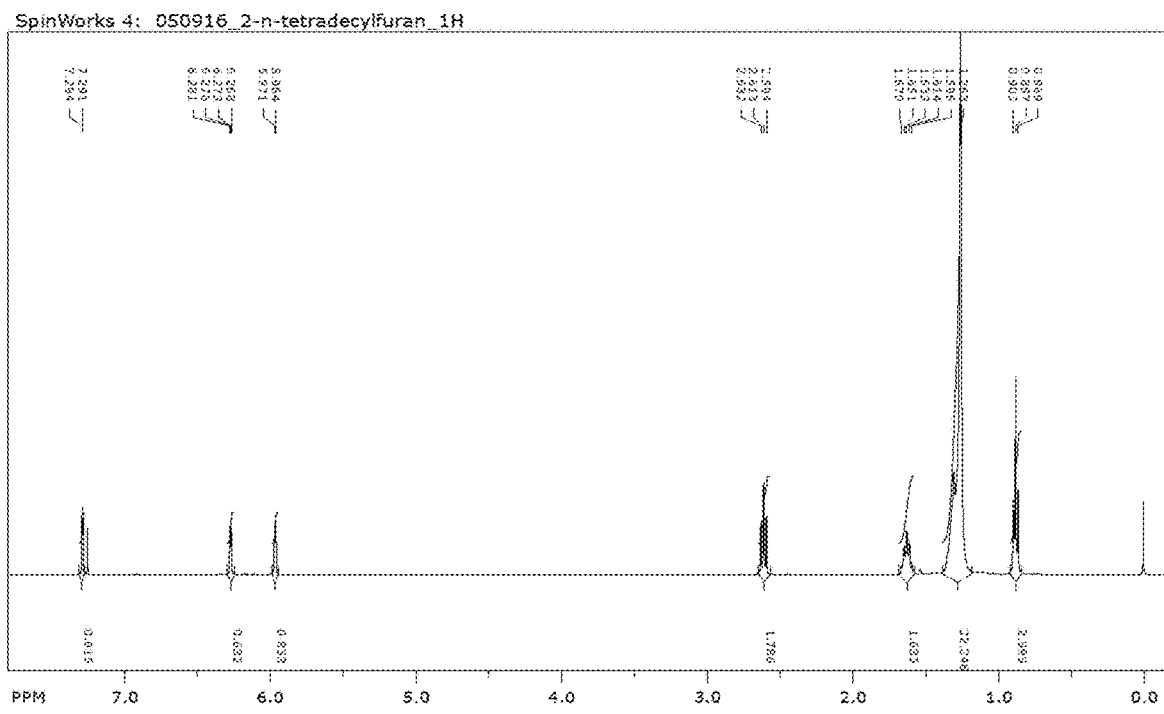
FIGS. 20A and 20B show the $^1$H NMR and $^{13}$C NMR of 2-n-tetradecylfuran in CDCl$_3$.
Figure 20B:
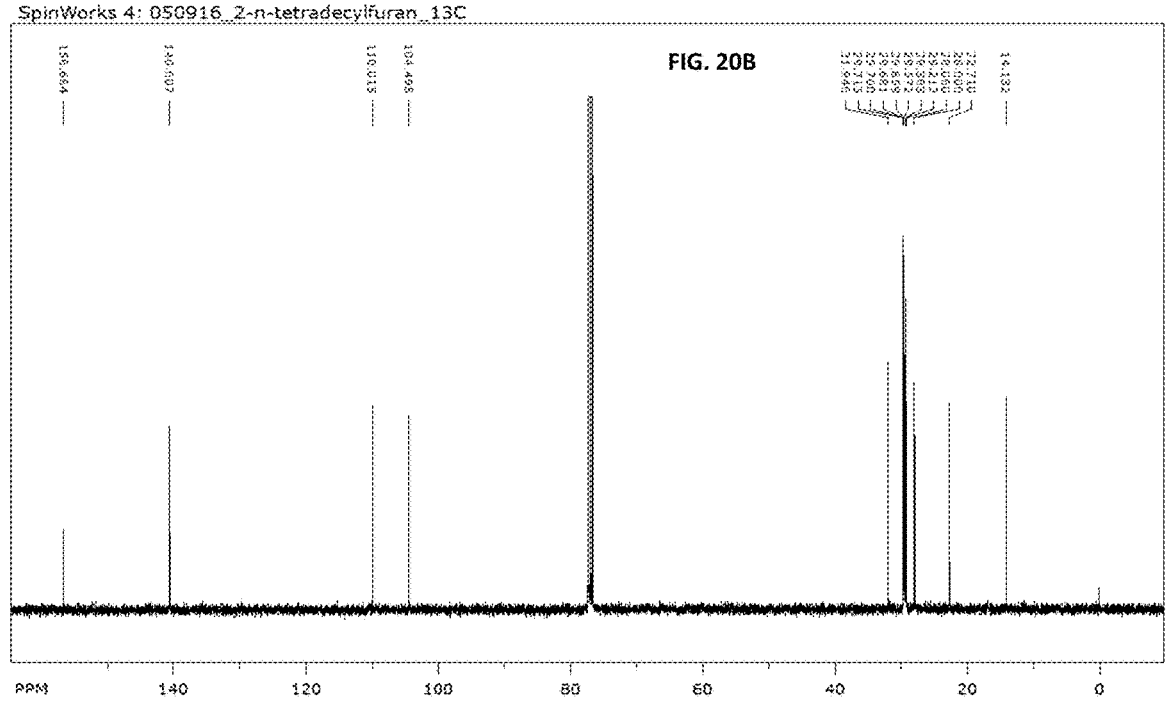

FIGS. 20A and 20B show the $^1$H NMR and $^{13}$C NMR of 2-n-tetradecylfuran in CDCl$_3$.

2-n-Octadecylfuran $^1$H-NMR (400 MHz, CDCl$_3$) δ 0.86-0.90 (t, 3H), 1.26 (brm, 30H), 1.59-1.66 (m, 2H), 2.59-2.63 (t, 2H), 5.96-5.97 (d, 1H), 6.26-6.27 (q, 1H), 7.28 (d, 1H) ppm.

$^{13}$C-NMR (100 MHz, CDCl$_3$) δ 14.13, 22.71, 27.99, 28.05, 29.21, 29.39, 29.50, 29.57, 29.66, 29.68, 29.72, 31.95, 104.49, 110.01, 140.61, 156.66 ppm.

GCMS (CI) m/z (relative intensity): 321.4 (22.6), 43.0 (100), 81.0 (61.7), 95.0 (55.6), 82.0 (29.2), 320.4 (21.8), 319.4 (17.9), 123.0 (11.7), 83.0 (11.3), 42.0 (11), 96.0 (10), 97.1 (10), 109.0 (9.2).

FIGS. 21A and 21B show the $^1$H-NMR and $^{13}$C NMR of 2-n-octadecylfuran in CDCl$_3$.

Mono Ethyl Branched 2-n-Dodecylfuran (Mixture with 60% of 2-n-Dodecylfuran)

$^1$H-NMR (400 MHz, CDCl$_3$) δ 0.86-0.90 (t, 3H), 0.87-0.91 (t, 3H), 1.26 (brm, 18H), 1.59-1.67 (q, 2H), 2.55-2.56 (d, 2H), 2.59-2.63 (t, 1H) 5.96-5.97 (t, 1H), 6.27-6.28 (q, 1H), 7.29-7.30 (q, 1H) ppm.

$^{13}$C-NMR (100 MHz, CDCl$_3$) δ 10.86, 14.13, 22.71, 25.92, 26.66, 28.00, 28.06, 29.21, 29.38, 29.58, 29.67, 29.69, 29.99, 31.94, 32.02, 33.06, 38.75, 105.73, 110.00, 140.64, 155.65 ppm GCMS (EI) m/z (relative intensity): 264 (7.7), 235 (8.0), 123 (25.6), 82 (99.9), 81 (65.8), 71 (36.3), 57 (56.8), 43 (38.7), 41 (23.7), 28 (91.9).

Figure 22A:
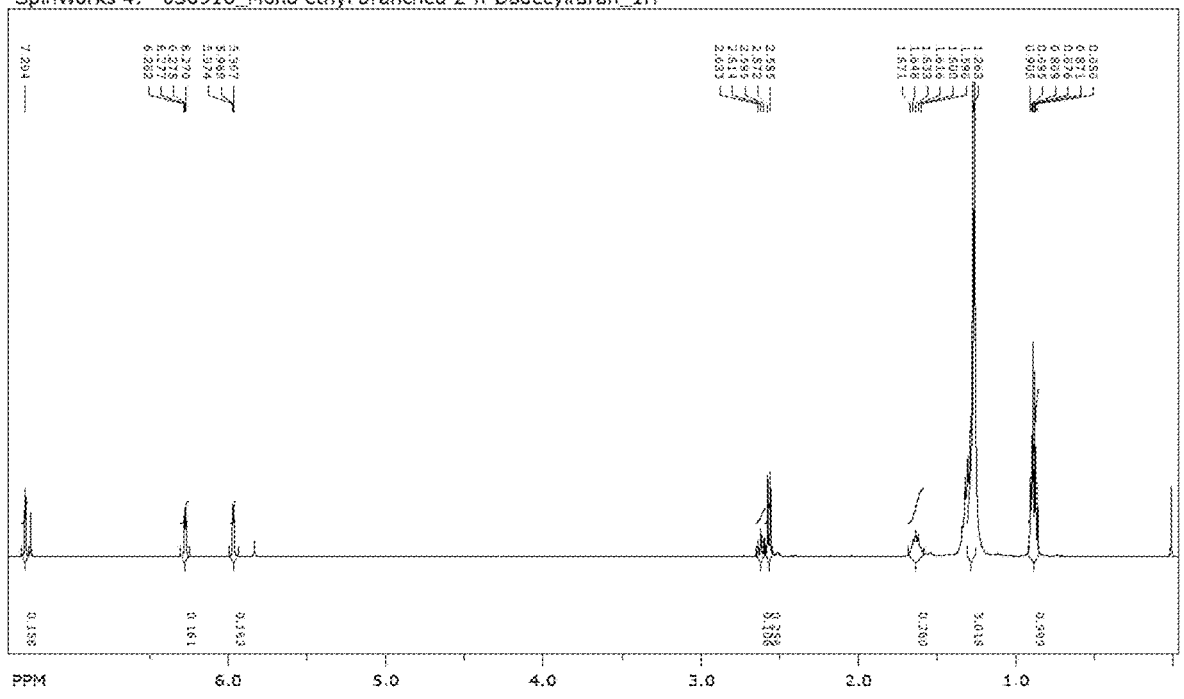
FIGS. 22A, 22B and 22C show the $^1$H NMR, $^{13}$C NMR and $^{13}$C-APT NMR of Mono ethyl branched 2-n-dodecyl-furan (Mixture with 60% of 2-n-dodecylfuran) in CDCl$_3$.
Figure 22B:
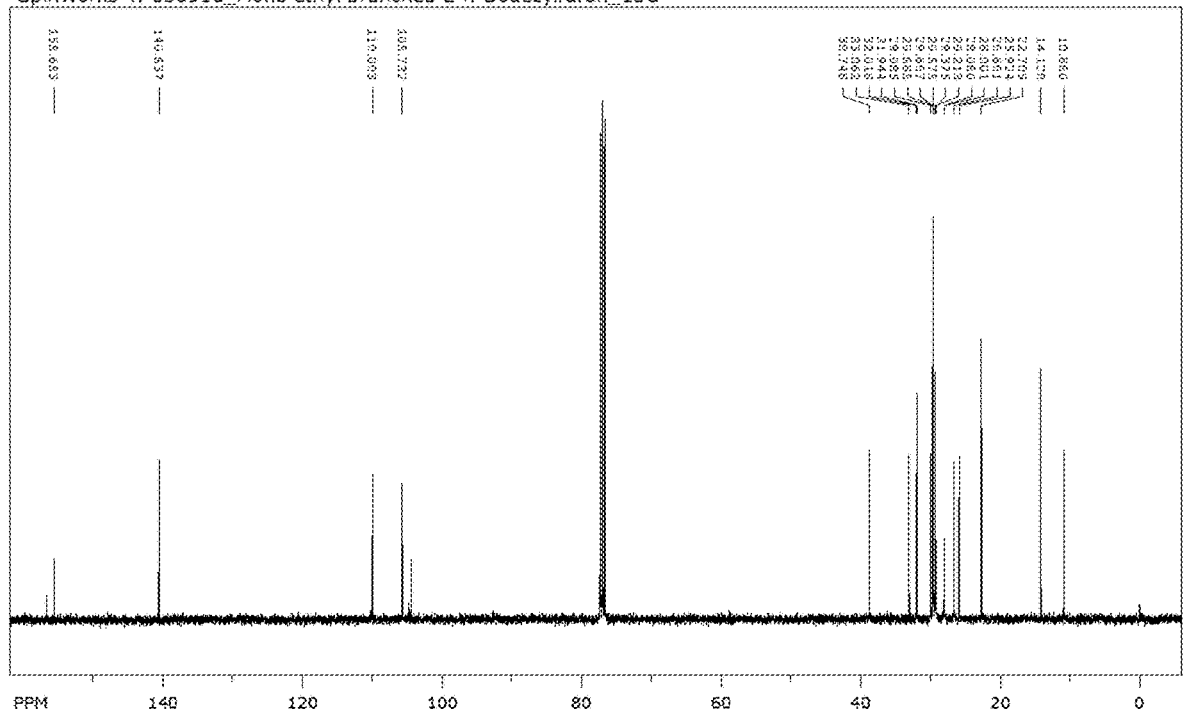
Figure 22C:
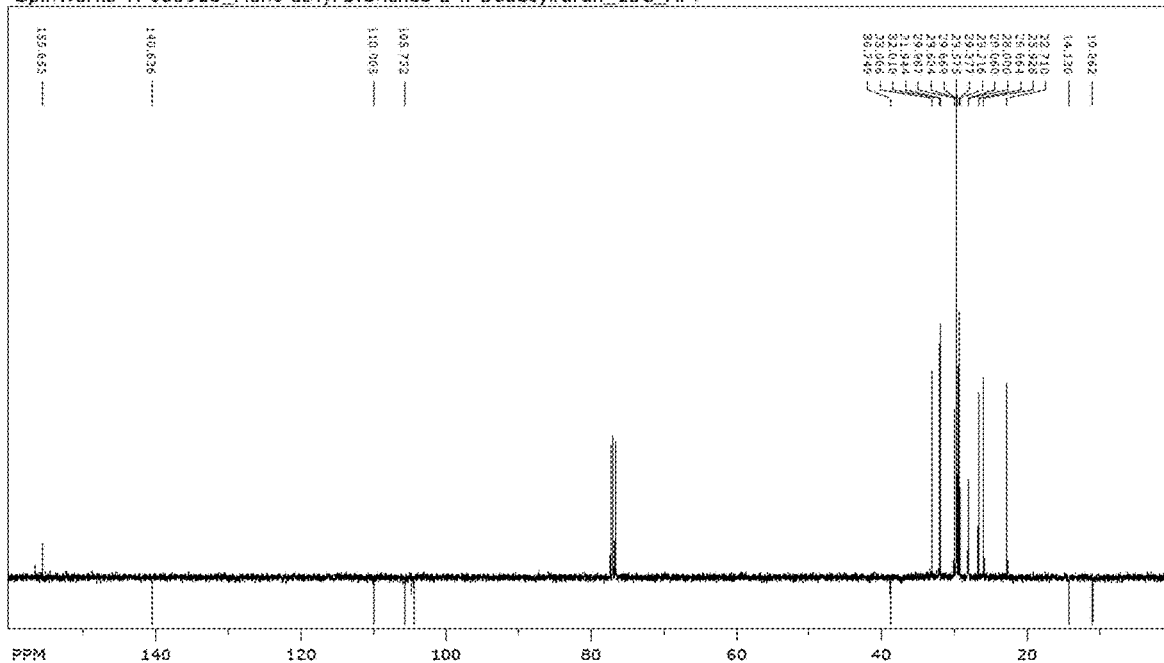

FIGS. 22A, 22B and 22C show the $^1$H NMR, $^{13}$C NMR and $^{13}$C-APT NMR of Mono ethyl branched 2-n-dodecylfuran (Mixture with 60% of 2-n-dodecylfuran) in CDCl$_3$.

OFS-7 (Sodium 5-Heptylfuran-2-Sulfonate)

$^1$H-NMR (400 MHz, DMSO-d$_6$) δ 0.84-0.88 (t, 3H), 1.26-1.28 (brm, 8H), 1.52-1.59 (m, 2H), 2.54-2.57 (t, 2H), 5.98-5.99 (d, 1H), 6.26-6.27 (d, 1H) ppm.

$^{13}$C-NMR (100 MHz, DMSO-d$_6$) δ 13.95, 22.08, 27.41, 27.55, 28.41, 28.54, 31.21, 105.07, 108.32, 155.15, 155.43 ppm.

Figure 23A:
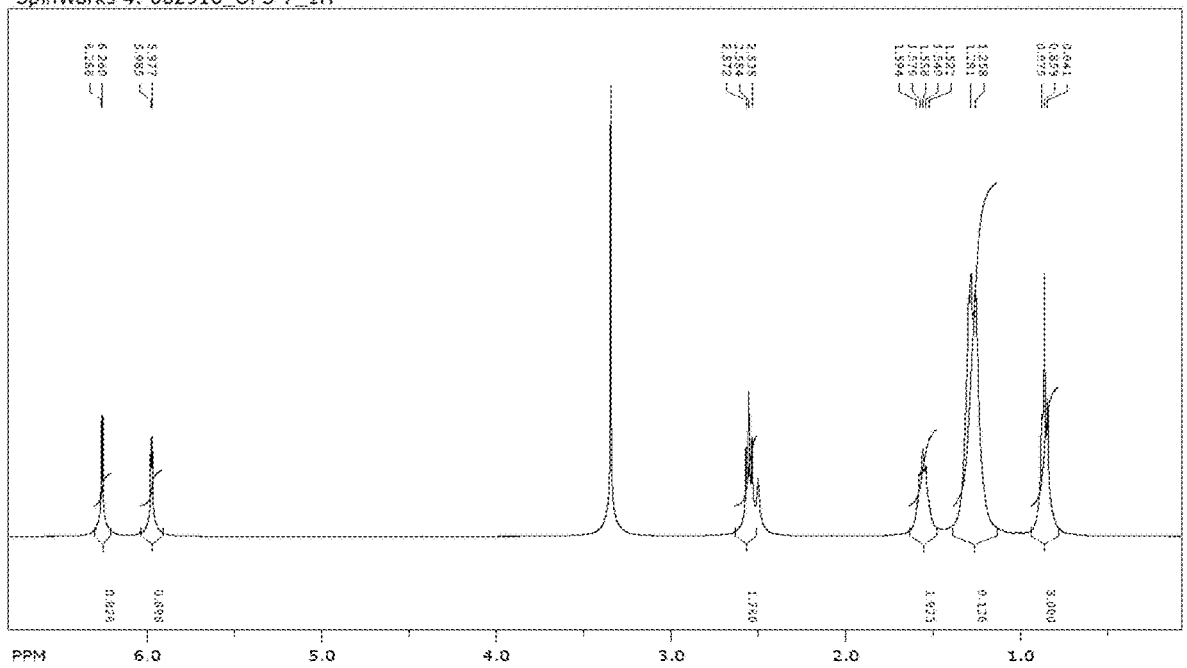
FIGS. 23A and 23B show the $^1$H NMR and $^{13}$C NMR of OFS-7 (Sodium 5-heptylfuran-2-sulfonate) in CDCl$_3$
Figure 23B:
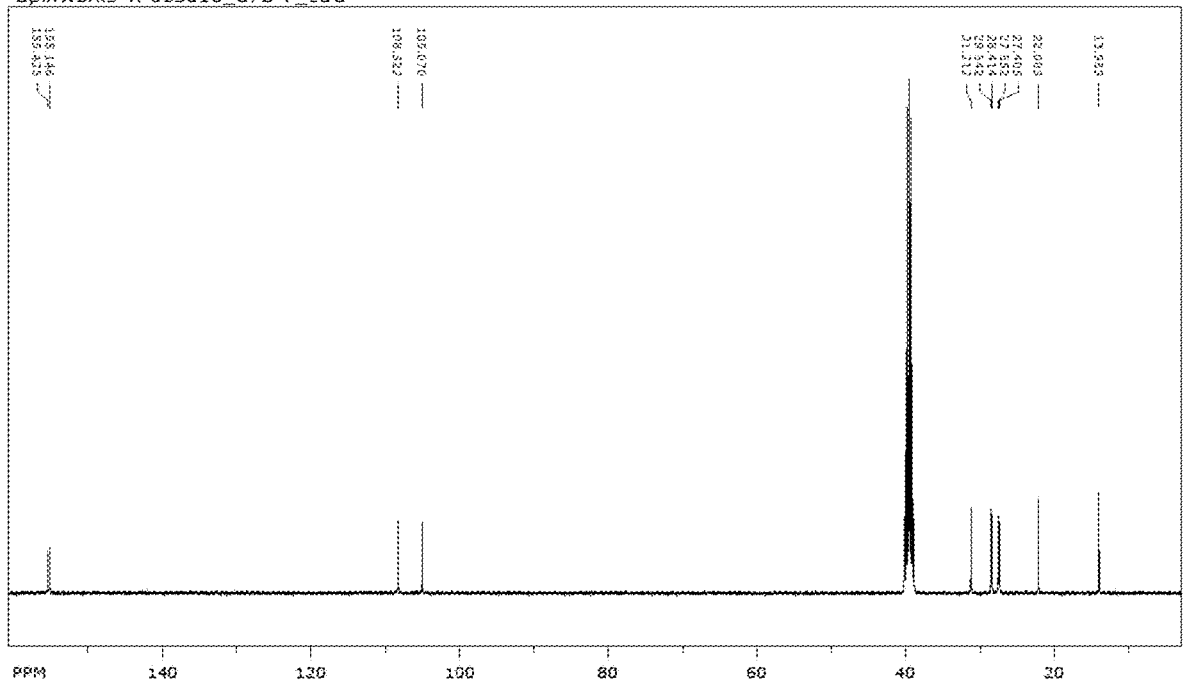

FIGS. 23A and 23B show the $^1$H NMR and $^{13}$C NMR of OFS-7 (Sodium 5-heptylfuran-2-sulfonate) in CDCl$_3$.

OFS-12 (Sodium 5-Dodecylfuran-2-Sulfonate)

$^1$H-NMR (400 MHz, DMSO-d$_6$) δ 0.84-0.87 (t, 3H), 1.24 (brm, 22H), 1.53-1.59 (m, 2H), 2.53-2.57 (t, 2H), 5.96-5.97 (d, 1H), 6.23-6.24 (d, 1H) ppm.

$^{13}$C-NMR (100 MHz, DMSO-d$_6$) δ 13.95, 22.09, 27.39, 27.54, 28.58, 28.70, 28.74, 28.97, 29.00, 29.03, 31.28, 104.98, 108.09, 154.98, 155.69 ppm.

Figure 24A:
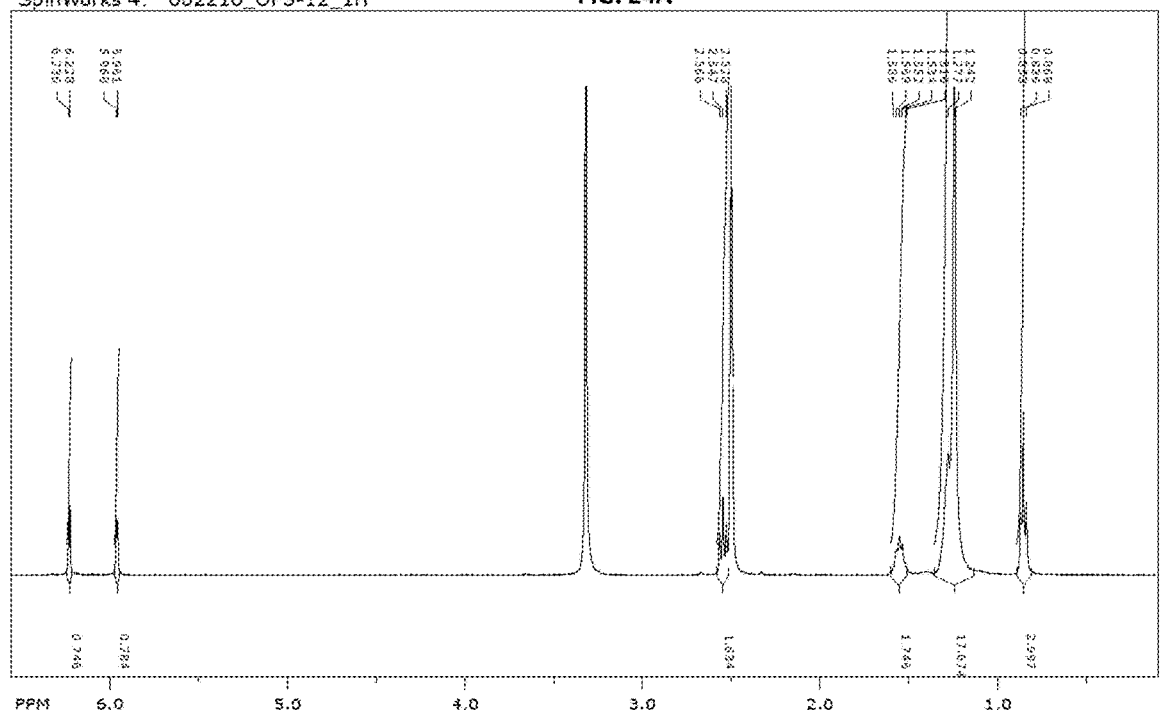
FIGS. 24A and 24B show the $^1$H NMR and $^{13}$C NMR of OFS-12 (Sodium 5-dodecylfuran-2-sulfonate) in CDCl$_3$
Figure 24B:
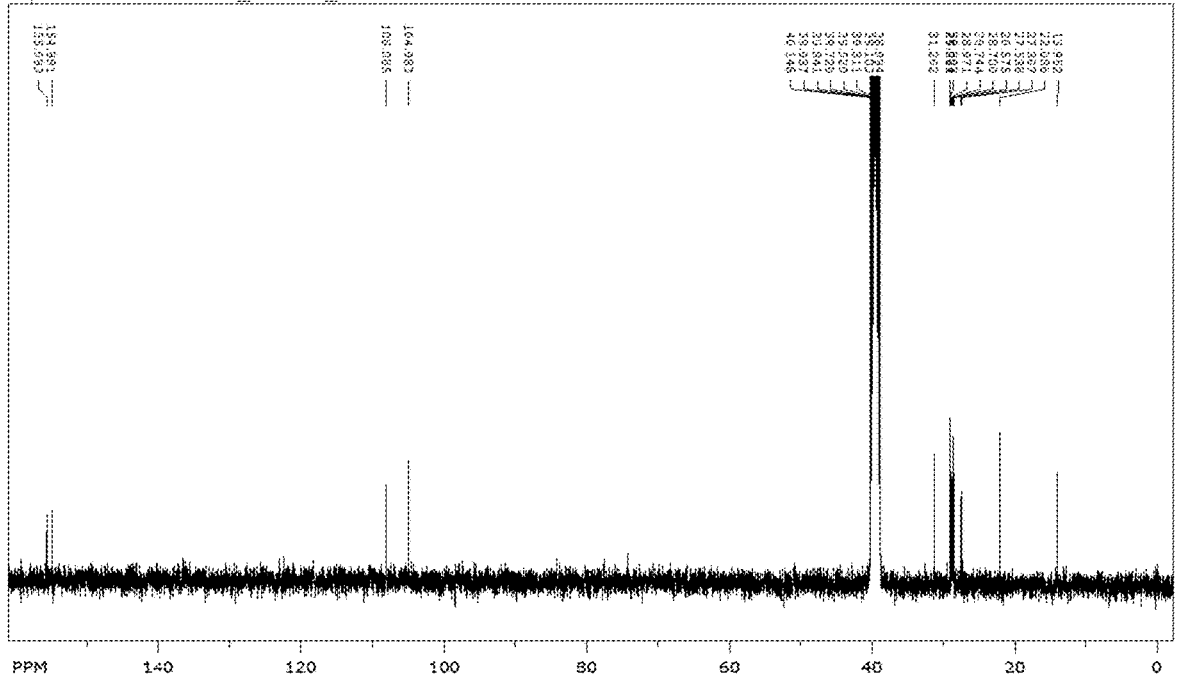

FIGS. 24A and 24B show the $^1$H NMR and $^{13}$C NMR of OFS-12 (Sodium 5-dodecylfuran-2-sulfonate) in CDCl$_3$.

OFS-14 (Sodium 5-Tetradecylfuran-2-Sulfonate)

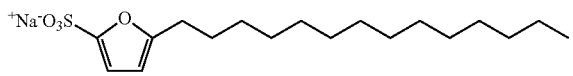

$^1$H-NMR (400 MHz, DMSO-$d_6$) δ 0.84-0.87 (t, 3H), 1.24 (brm, 22H), 1.52-1.59 (m, 2H), 2.53-2.57 (t, 2H), 5.96-5.97 (d, 1H), 6.24 (d, 1H) ppm.

$^{13}$C-NMR (100 MHz, DMSO-$d_6$) δ 13.96, 22.10, 27.40, 27.55, 28.59, 28.71, 28.76, 28.99, 29.01, 29.05, 31.30, 105.00, 108.15, 155.03, 155.63 ppm.

Figure 25A:
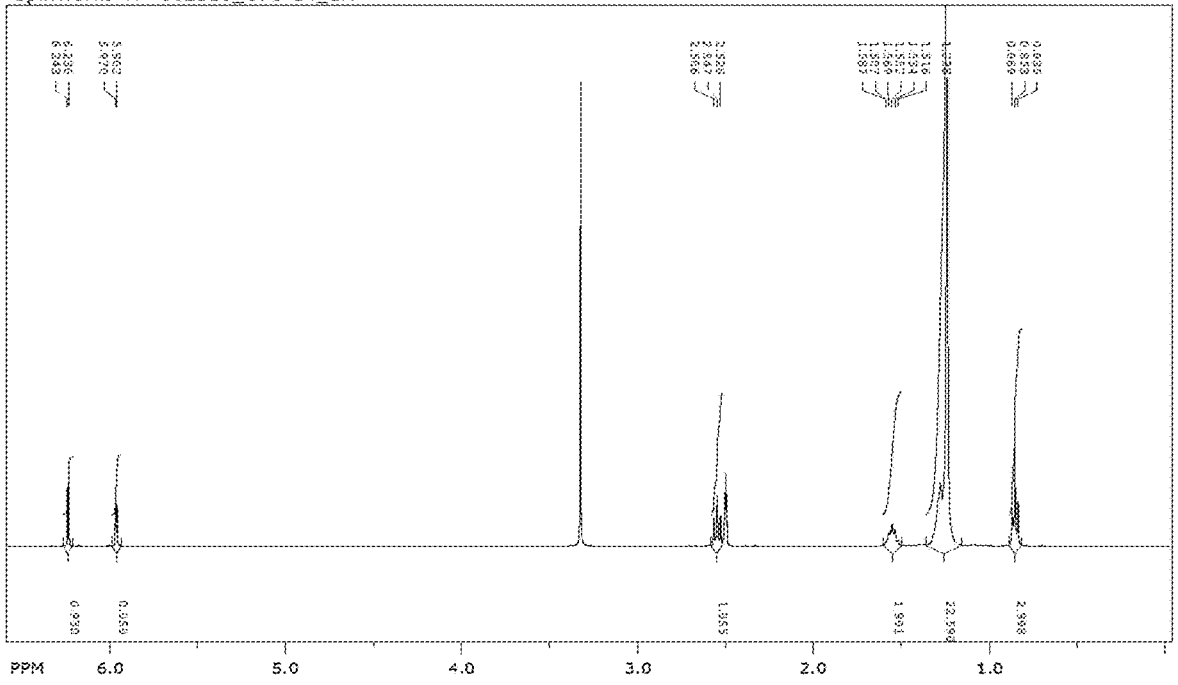
FIGS. 25A and 25B show the $^1$H NMR and $^{13}$C NMR of OFS-14 (Sodium 5-tetradecylfuran-2-sulfonate) in CDCl$_3$
Figure 25B:
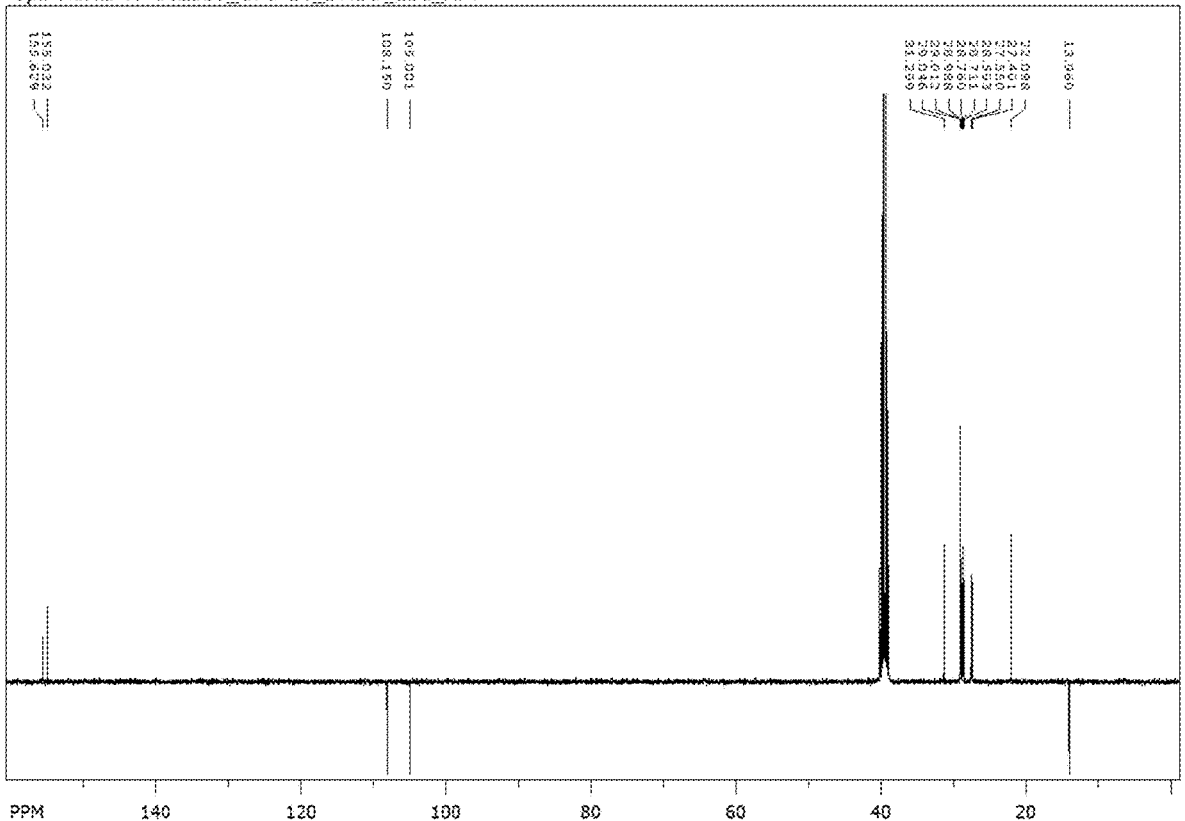

FIGS. 25A and 25B show the $^1$H-NMR and $^{13}$C NMR of OFS-14 (Sodium 5-tetradecylfuran-2-sulfonate) in CDCl$_3$.
Particle Size Distribution of Micelles Via Dynamic Light Scattering (DLS)

Figure 26A:
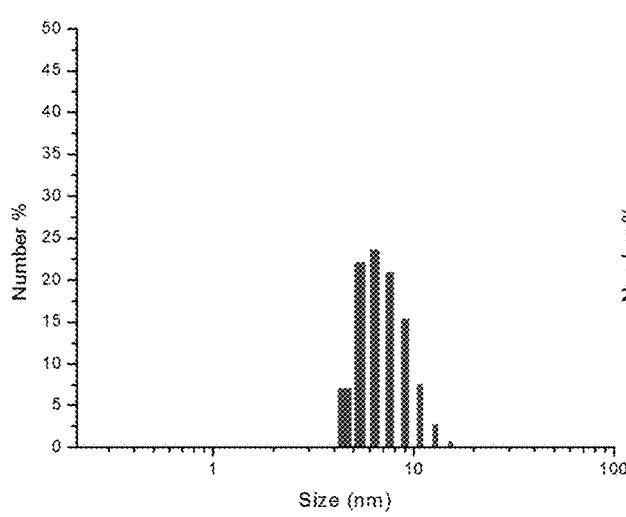
FIGS. 26A and 26B show particle size (number) distribution for micelles in OFS-12 surfactant solution with concentration 5.0×CMC (average size, 7.41 nm) (FIG. 26A) and 10.0×CMC (average size, 6.29 nm) (FIG. 26B).
Figure 26B:
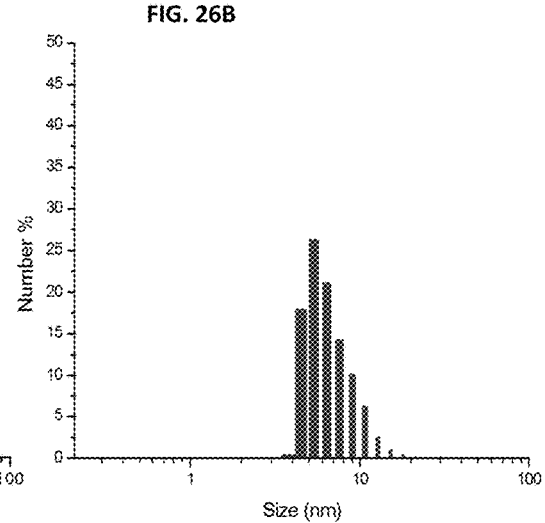

Dynamic Light Scattering (DLS) has been used in the past for studying surfactant aggregates (N. Vlachy, M. Drechsler, J.-M. Verbavatz, D. Touraud, W. Kunz, Role of surfactant headgroup on the counterion specificity in the micelle-to-vesicle transition through salt addition. *J. Colloid Interface Sci.* 319, 542-548 (2008)). Micelle size distribution studies of the OFS-12 surfactant was performed using the Microtrac NANO-flex analyzer which employs a 180° scattering angle DLS technique. Two different surfactant concentration samples were prepared (5.0 and 10×CMC, 0.35 and 0.7 wt %) by dissolving the required amount of surfactant in deionized water and filtering the solution after surfactant dissolution using a 0.2μ micropore filter to remove any dust particles. Prior to each sample run, a blank solution (DI water) was used to set the baseline to zero. FIGS. 26A and 26B show the average particle size distribution plots for the surfactant solutions. The average values were computed based on five individual trials each lasting 120 sec.

Evaluation of the Surfactants

Evaluation of surfactant performance was carried out by analyzing properties of surfactants in solution such as critical micelle concentration (CMC), Krafft point, 'foaminess', wettability (Draves index) and hard water stability (hardness tolerance).

Critical Micelle Concentration (CMC)

CMC is an important property of a surfactant and is the concentration above which the surfactant forms micelles and any additional surfactant added to the solution will also form micelles. The value of CMC of the surfactant was measured by recording the decrease in surface tension with increasing surfactant concentration. 6-8 samples with increasing surfactant concentration were prepared by dissolving the required amount of surfactant in deionized water. The solution temperature was kept high enough to ensure that all of the surfactant is in solution i.e. the solution temperature was kept above the Krafft point of the surfactant. Surface tension measurements were made using the Krüss digital tensiometer K10ST via the Wilhelmy plate method. In this method, the force exerted on the wetted perimeter of the platinum plate immersed into a surfactant solution was correlated with its surface tension via the formula:

$$\sigma = \frac{F}{L \cdot \cos\theta} \quad (1)$$

where σ is the surface tension, F is the force exerted, L is the wetted length and θ is the contact angle.

The temperature of the solution was monitored during the course of measurement. The surface tension of each concentration was measured three times and CMC was reported as the value of concentration corresponding to the point of intersection of two straight lines drawn to fit the plot of surface tension vs. ln(surfactant concentration).

FIGS. 27A, 27B, 27C and 27D show plots of surface tension versus surfactant concentration of commercial surfactants: sodium Lauryl Sulfate (SLS) (FIG. 27A), Methyl Ester Sulfonate (MES) (FIG. 27B), Linear Alkylbenzene Sulfonate (LAS) (FIG. 27C) and, Sodium Lauryl Ether Sulfate (SLES) (FIG. 27D). The point of intersection of the two dashed lines in the surface tension vs ln(C) plot yields the value of CMC.

FIGS. 28A, 28B, 28C and 28D show plots of surface tension versus surfactant concentration of renewable OFS-n-1/O surfactants: OFS-12-1/O (FIG. 28A), OFS-14-1/O (FIG. 28B), OFS-18-1/O (FIG. 28C) and OFS-Cocinic-1/O, n=8-18 (FIG. 28C). The point of intersection of the two dashed lines in the surface tension vs ln(C) plot yields the value of CMC.

FIGS. 29A, 29B, 29C, 29D, 29E, 29F and 29G show plots of surface tension versus surfactant concentration of renewable OFS-n surfactants: OFS-7 (FIG. 29A), OFS-12 (FIG. 29B), OFS-14 (FIG. 29C), OFS-18 (FIG. 29D), OFS-Cocinic, n=8-18 (FIG. 29E), 40:60 mol % OFS-12-2/C2H5:OFS-12 (FIG. 29F) and, 85:15 mol % OFS-12-1/O:OFS-12 (FIG. 29G). The point of intersection of the two dashed lines in the surface tension vs ln(C) plot yields the value of CMC.

Table 21 shows the CMC values for all surfactants tested.

TABLE 21

Summary of CMC values for all surfactants in ppm and mmol/L (mM).

| Surfactant | CMC[a] | |
|---|---|---|
| | [ppm] | mmol/L |
| Commercial | | |
| SLS, Sodium Lauryl Sulfate | 2010 | 6.97 |
| MES, Methyl Ester Sulfonate | 130 | 0.41 |
| LAS, Linear Alkylbenzene Sulfonate | 460 | 1.33 |
| SLES, Sodium Lauryl Ether Sulfate | 380 | 1.01 |
| OFS, Oleo-Furan Sulfonates | | |
| OFS-12-1/O | 11520 | 33.11 |
| OFS-14-1/O | 3127 | 8.26 |
| OFS-18-1/O | 1156 | 2.65 |
| OFS-Cocinic-1/O | 4890 | 14.01 |
| OFS-7 | 2669 | 9.99 |
| OFS-12 | 720 | 2.13 |
| OFS-14 | 267 | 0.72 |
| OFS-18 | 316 | 0.75 |
| OFS-Cocinic | 512 | 1.51 |
| 40:60 mol % OFS-12-2/C2H5:OFS-12 | 496 | 1.43 |
| 85:15 mol % OFS-12-1/O:OFS-12 | 2445 | 7.01 |

[a]Critical Micelle Concentration, measured above Krafft point

Krafft Point/Temperature

Krafft point or Krafft temperature is the minimum temperature at which surfactants form micelles. Below Krafft point, the surfactants precipitate out of solution and remain in the crystalline phase. FIG. 30 depicts the apparatus utilized for the measurement of Krafft points. A 1.0 wt % solution of surfactant in deionized water was prepared for all surfactants except in the case of OFS-12-1/O where a 2.0 wt % solution was used instead, since its CMC is roughly about 1.1 wt %. 50 mL of the prepared solution was poured into a beaker surrounded by a freezing mixture of ice and salt (sodium chloride) mounted on a laboratory hot plate with magnetic stirring. The Krafft point (TK) of the surfactants was measured by estimating the degree of counterion dissociation using a conductivity meter (COND 6+, Oakton/Eutech Instruments) immersed in the surfactant solution capable of measuring both, conductivity and temperature. The magnetic stirring speed was set to 650 rpm and the solution was first allowed to cool to 0° C. Upon attainment of this temperature, the solution was slowly heated and the conductivity was measured in every 0.5° C. increments until it reached a steady value. The Krafft point was taken as the temperature where the conductivity vs. temperature plot exhibited a sharp change in slope. Visually, this corresponded to the surfactant solution transitioning from a turbid system due to the precipitated surfactant crystals below the Krafft point to a clear solution indicating the dissolution of surfactants and the formation of micelles in water.

Figure 31A:
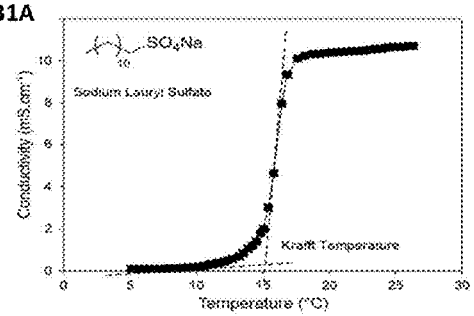
FIGS. 31A, 31B, 31C, 31D, 31E, 31F and 31G show conductivity versus temperature of 1.0 wt % surfactant solutions for determination of Krafft point: Sodium Lauryl Sulfate (SLS) (FIG. 31A), Linear Alkylbenzene Sulfonate (LAS) (FIG. 31B), OFS-12 (FIG. 31C), OFS-14 (FIG. 31D), OFS-18 (FIG. 31E), 40:60 mol % OFS-12-2/C2H5:OFS-12 (FIG. 31F) and OFS-Cocinic, n=8-18 (FIG. 31G).
Figure 31B:
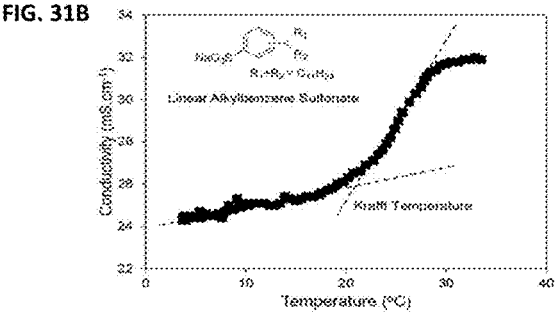
Figure 31C:
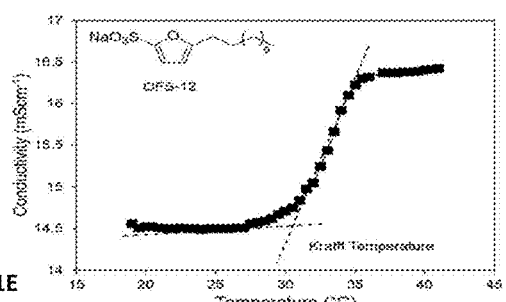
Figure 31D:
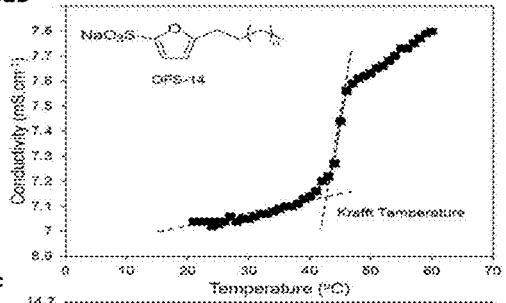
Figure 31E:
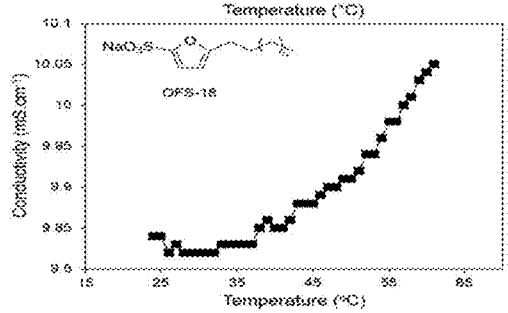
Figure 31F:
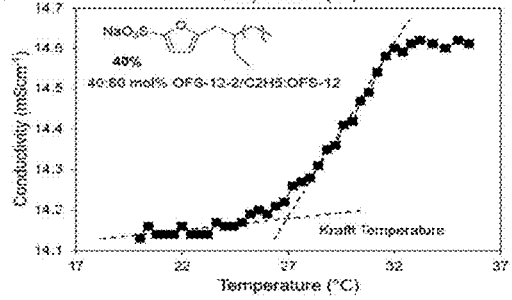
Figure 31G:
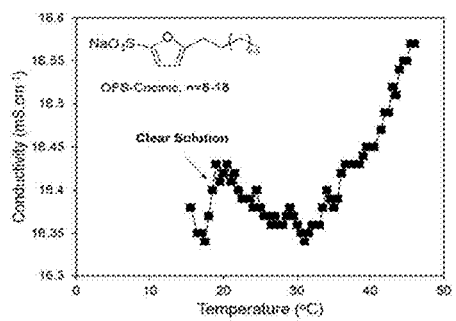

FIGS. 31A, 31B, 31C, 31D, 31E, 31F and 31G show conductivity versus temperature of 1.0 wt % surfactant solutions for determination of Krafft point: Sodium Lauryl Sulfate (SLS) (FIG. 31A), Linear Alkylbenzene Sulfonate (LAS) (FIG. 31B), OFS-12 (FIG. 31C), OFS-14 (FIG. 31D), OFS-18 (FIG. 31E), 40:60 mol % OFS-12-2/C2H5:OFS-12 (FIG. 31F) and OFS-Cocinic, n=8-18 (FIG. 31G).

In the case of OFS-18, maximum temperature operation limits of the conductivity probe did not allow the estimation of Krafft point, and thus the value is reported as >50° C. For the OFS-Cocinic, n=8-18 surfactant, the conductivity vs temperature plot was erratic, which is attributed to the presence of 6 different surfactants in the mixture. The solution changed from turbid to clear at approximately 18.5° C. which was, therefore, reported as the Krafft point. Methyl Ester Sulfonate (MES), Sodium Lauryl Ether Sulfate (SLES), OFS-7 and all OFS-n-1/O surfactant solutions remained clear even at 0° C.; the Krafft point was thus reported as <0° C.

Table 22 shows a summary of the Krafft point measurements for the illustrative surfactants.

TABLE 22

Summary of Krafft points for all surfactants.

| Surfactant | Krafft Point[a] [° C.] |
|---|---|
| Commercial | |
| SLS, Sodium Lauryl Sulfate | 15.0 ± 1.2 |
| MES, Methyl Ester Sulfonate | <0 |
| LAS, Linear Alkylbenzene Sulfonate | 20.0 ± 2.5 |
| SLES, Sodium Lauryl Ether Sulfate | <0 |
| OFS, Oleo-Furan Sulfonates | |
| OFS-12-1/O | <0 |
| OFS-14-1/O | <0 |
| OFS-18-1/O | <0 |
| OFS-Cocinic-1/O | <0 |
| OFS-7 | <0 |
| OFS-12 | 30.0 ± 1.0 |
| OFS-14 | 41.5 ± 0.9 |
| OFS-18 | >50 |
| OFS-Cocinic | 18.5 ± 0.5 |
| 40:60 mol % OFS-12-2/C2H5:OFS-12 | 25.7 ± 0.5 |
| 85:15 mol % OFS-12-1/O:OFS-12 | <0 |

[a]Measured at 1.0 wt % surfactant in water except for OFS-12-1/O

Surfactant Foaming

Figure 32:
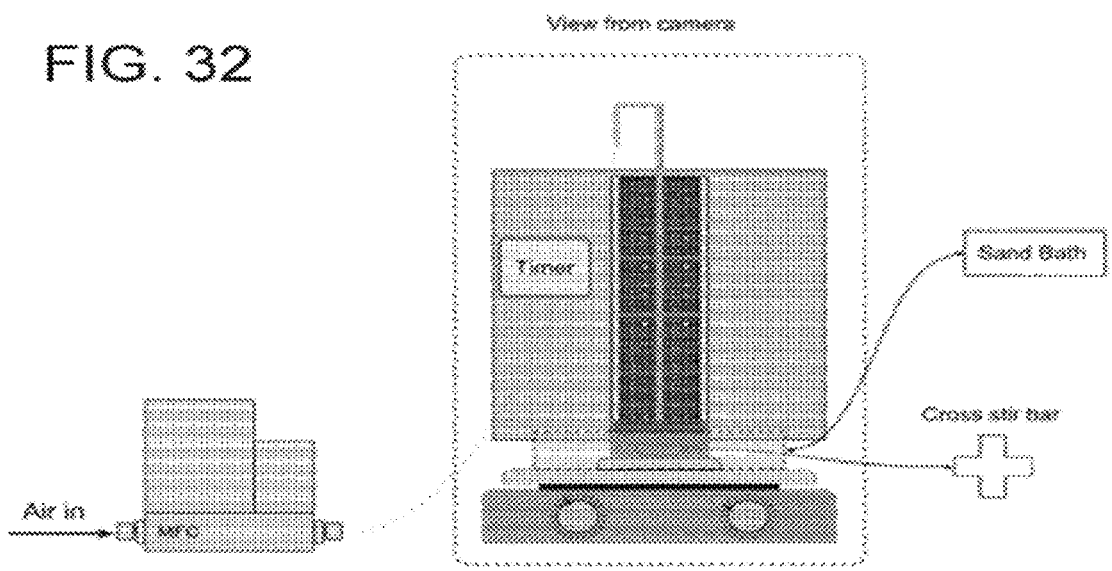
FIG. 32 shows a schematic of the foaming apparatus utilized to measure foaming of the surfactants.
Figure 33:
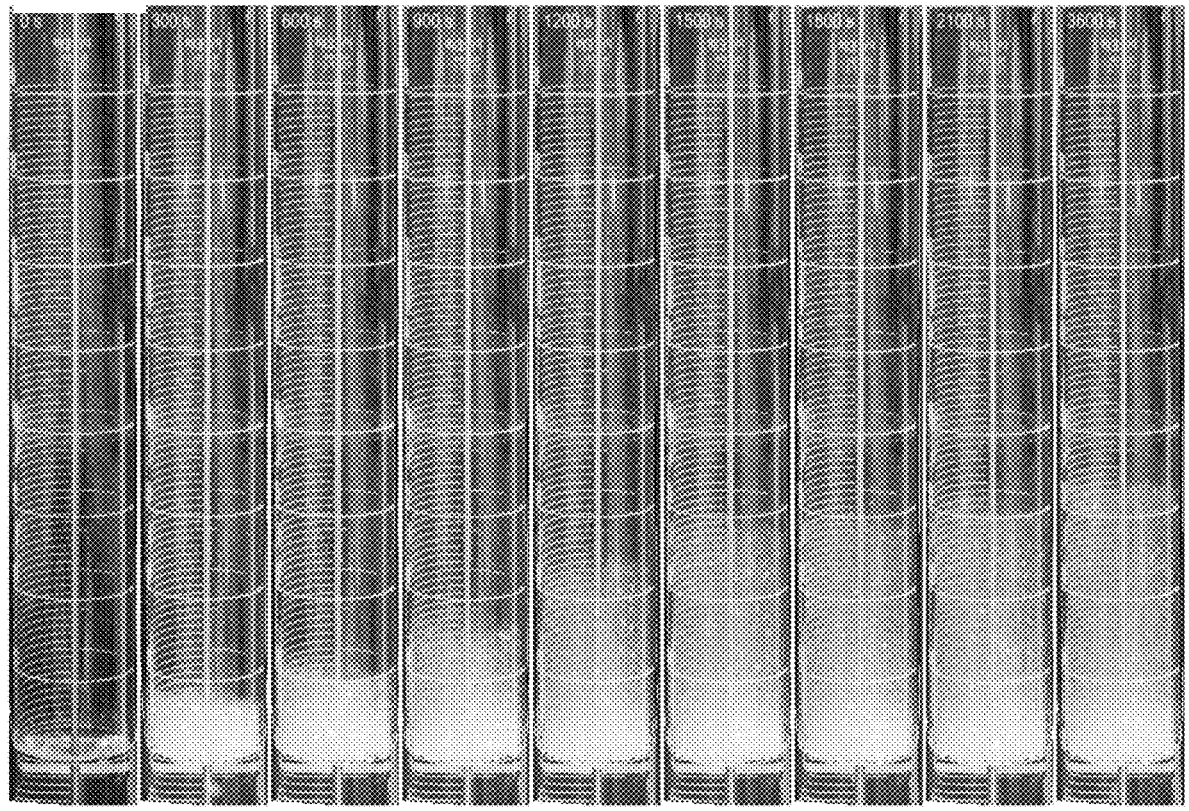
FIG. 33 show from left to right, at 0 seconds (s), 300 s, 600 s, 900 s, 1200 s, 1500 s, 1800 s, 2100 s and 3600 s (one hour) the foam growth of a 0.5 wt % solution of Sodium Lauryl Sulfate (SLS).
Figure 34:
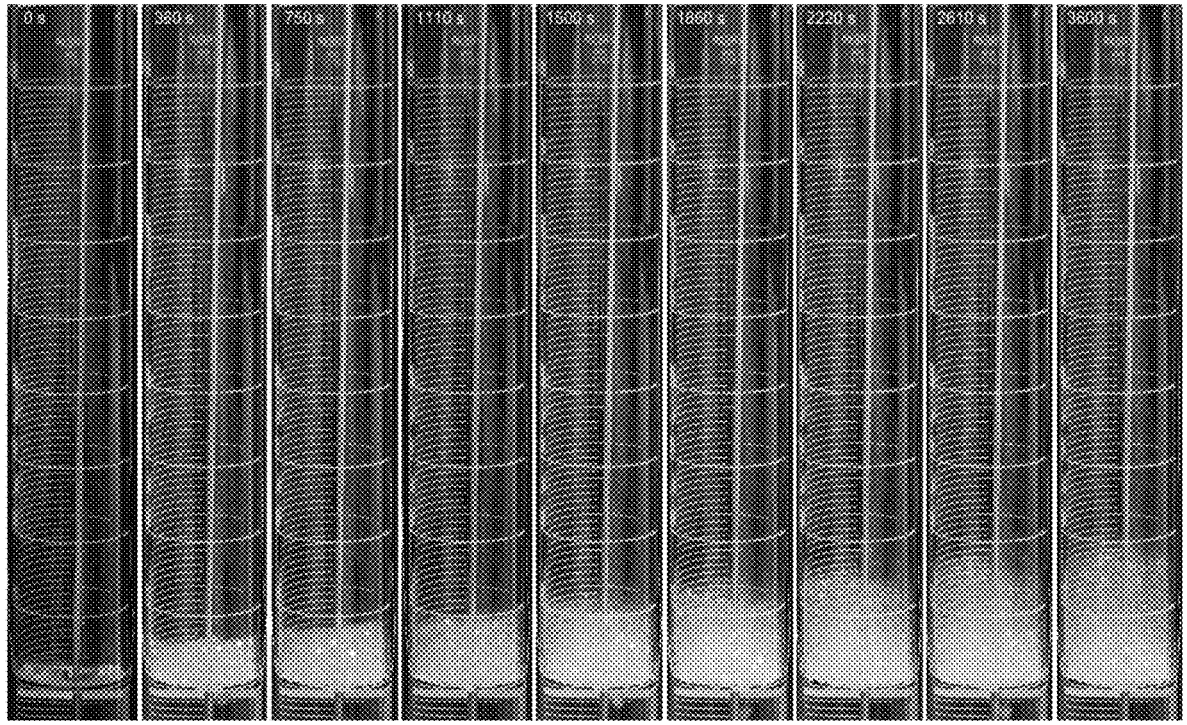
FIG. 34 show from left to right, at 0 seconds (s), 300 s, 600 s, 900 s, 1200 s, 1500 s, 1800 s, 2100 s and 3600 s (one hour) the foam growth of a 0.5 wt % solution of Methyl Ester Sulfonate (MES).
Figure 35:
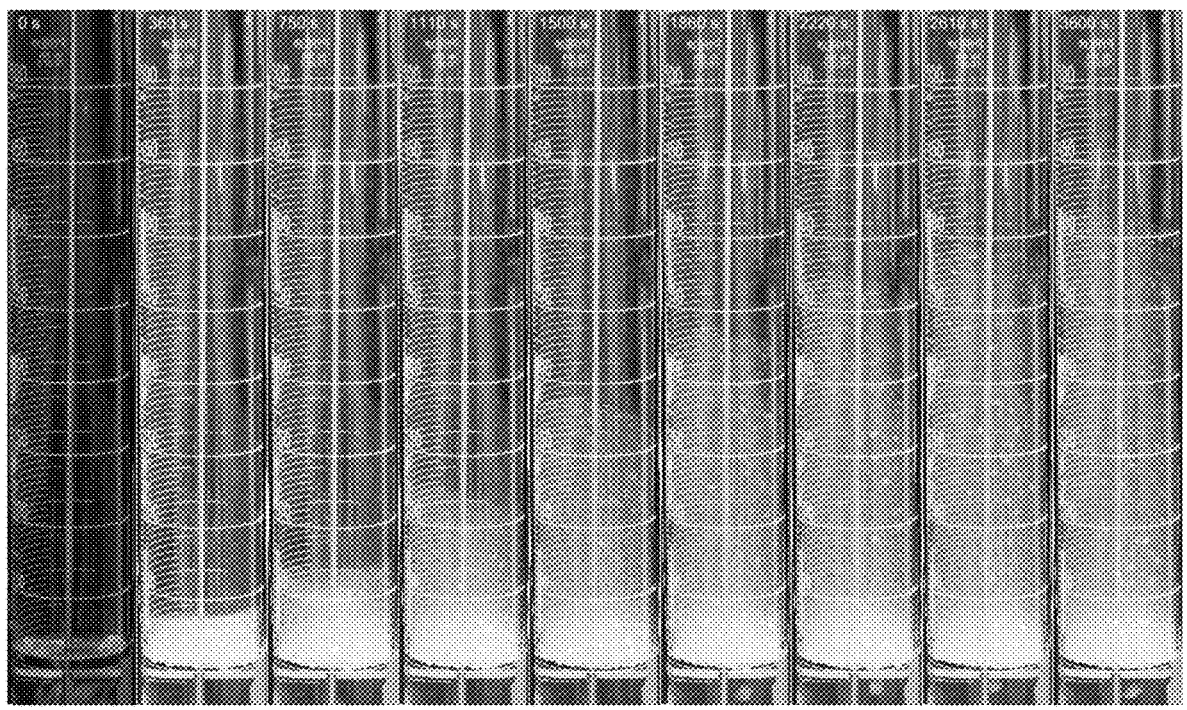
FIG. 35 show from left to right, at 0 seconds (s), 300 s, 600 s, 900 s, 1200 s, 1500 s, 1800 s, 2100 s and 3600 s (one hour) the foam growth of a 0.5 wt % solution of Linear Alkylbenzene Sulfonate (LAS).
Figure 36:
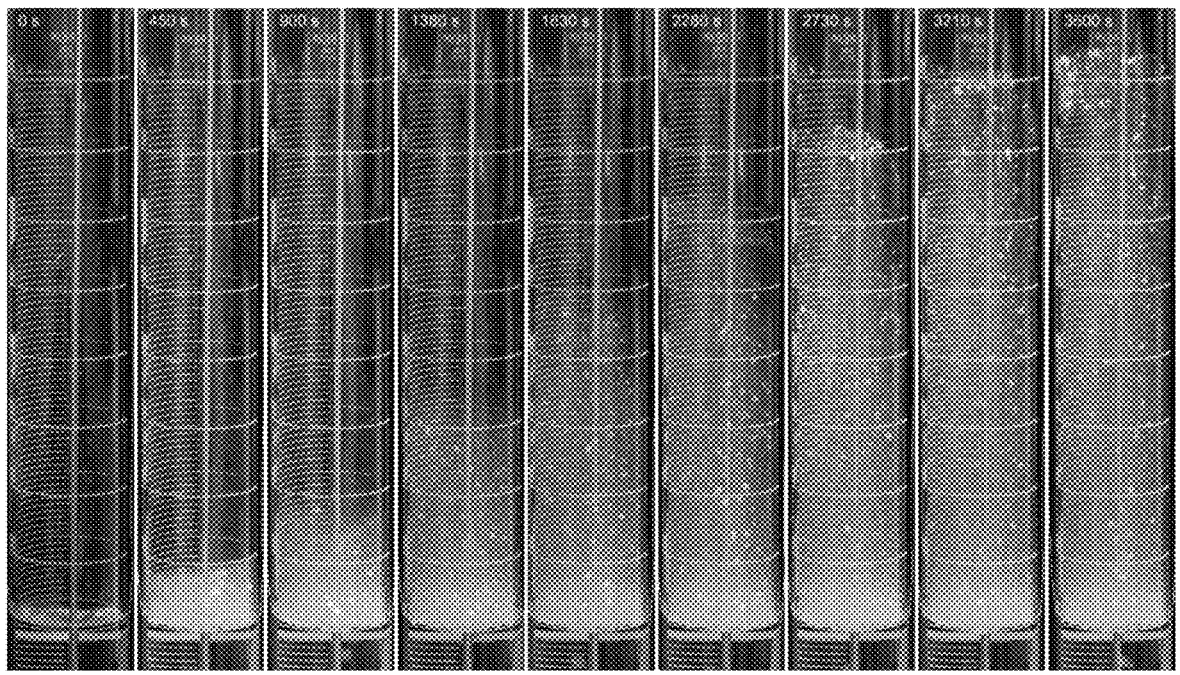
FIG. 36 show from left to right, at 0 seconds (s), 300 s, 600 s, 900 s, 1200 s, 1500 s, 1800 s, 2100 s and 3600 s (one hour) the foam growth of a 0.5 wt % solution of Sodium Lauryl Ether Sulfate (SLES).
Figure 37:
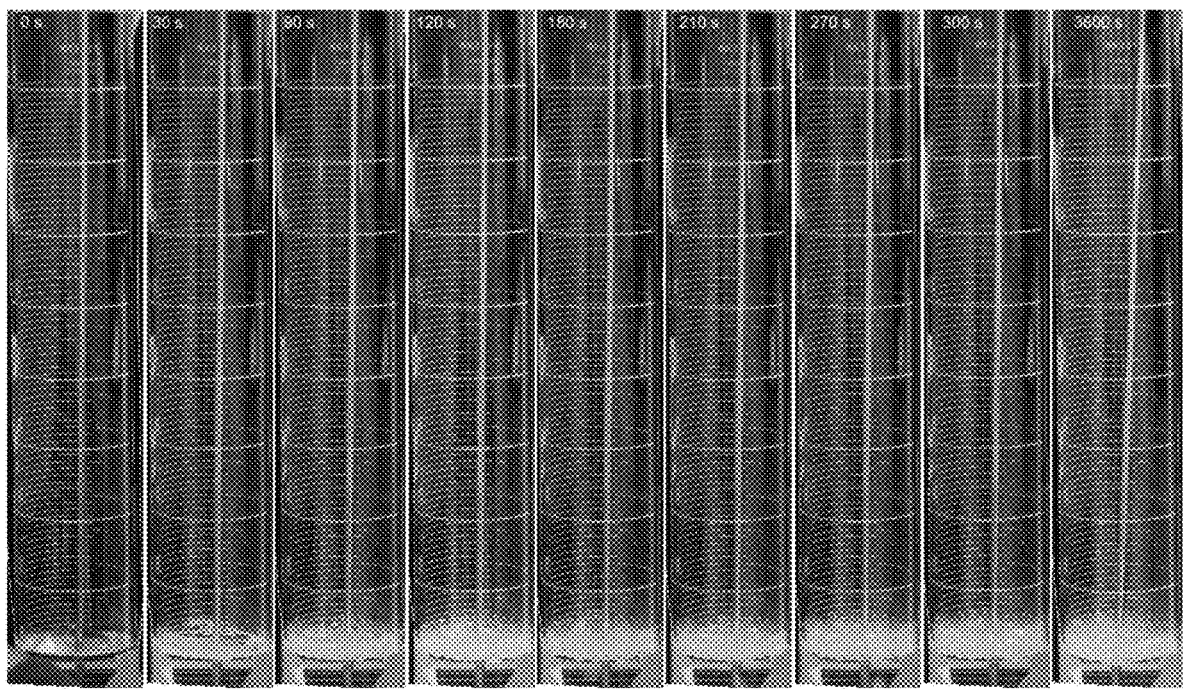
FIG. 37 show from left to right, at 0 seconds (s), 300 s, 600 s, 900 s, 1200 s, 1500 s, 1800 s, 2100 s and 3600 s (one hour) the foam growth of a 0.5 wt % solution of OFS-7.
Figure 38:
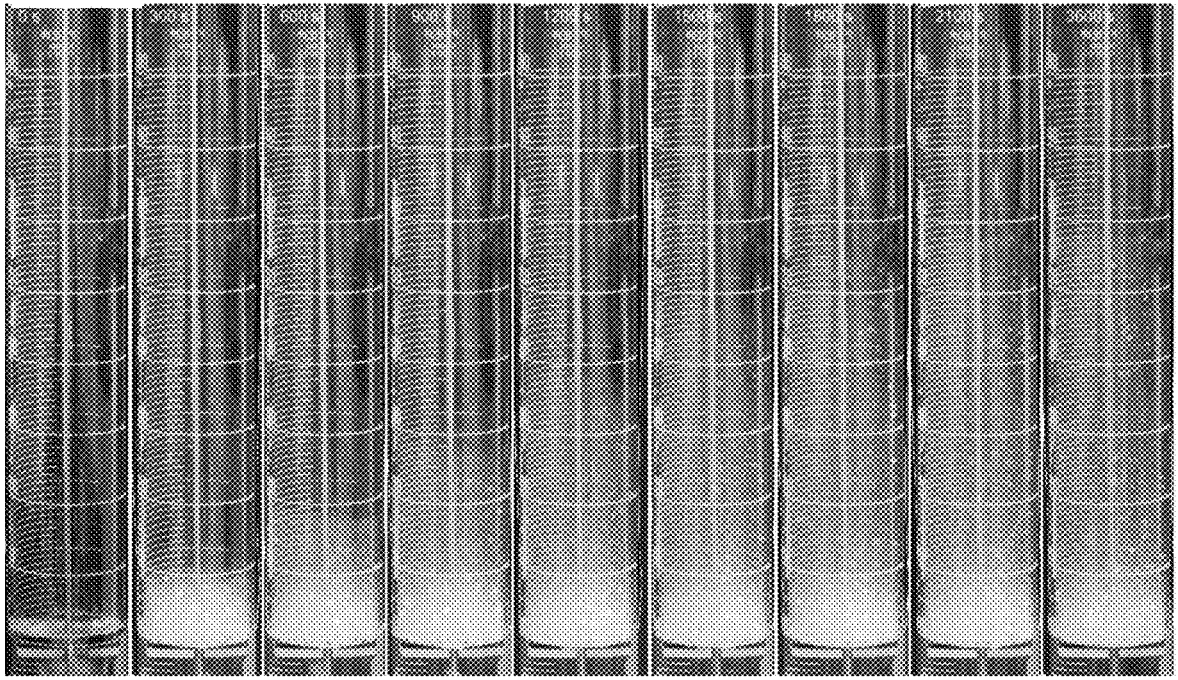
FIG. 38 show from left to right, at 0 seconds (s), 300 s, 600 s, 900 s, 1200 s, 1500 s, 1800 s, 2100 s and 3600 s (one hour) the foam growth of a 0.5 wt % solution of OFS-12.
Figure 39:
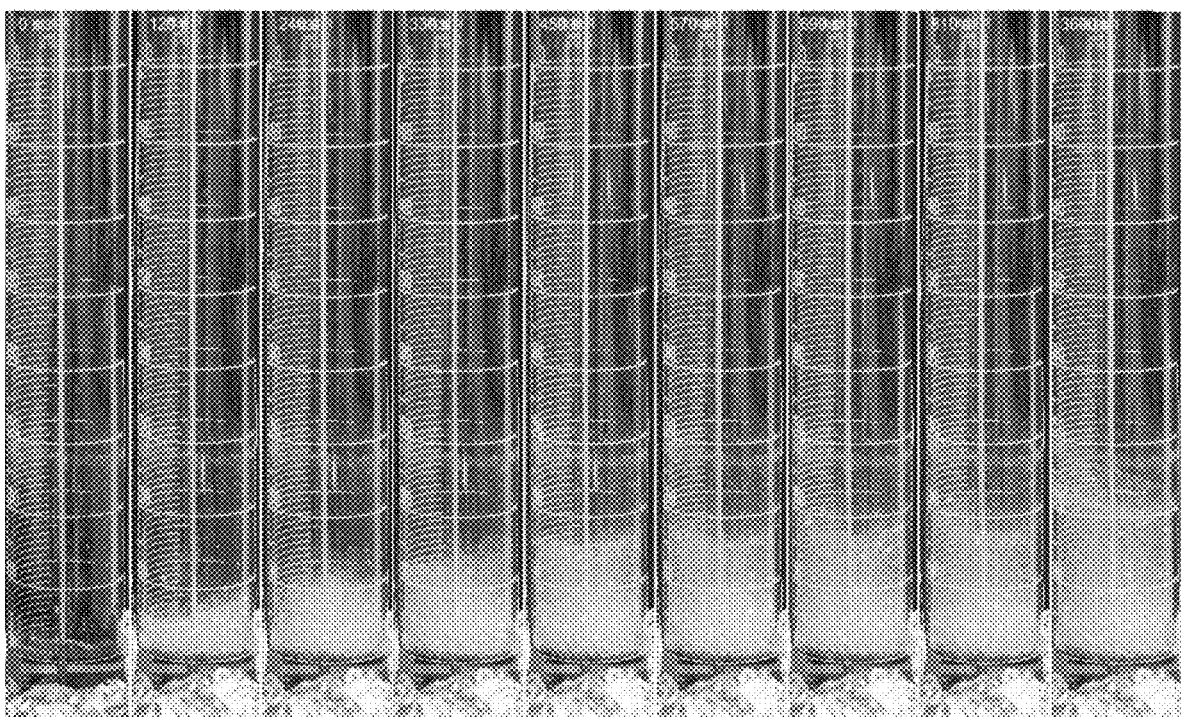
FIG. 39 show from left to right, at 0 seconds (s), 300 s, 600 s, 900 s, 1200 s, 1500 s, 1800 s, 2100 s and 3600 s (one hour) the foam growth of a 0.5 wt % solution of OFS-14.
Figure 40:
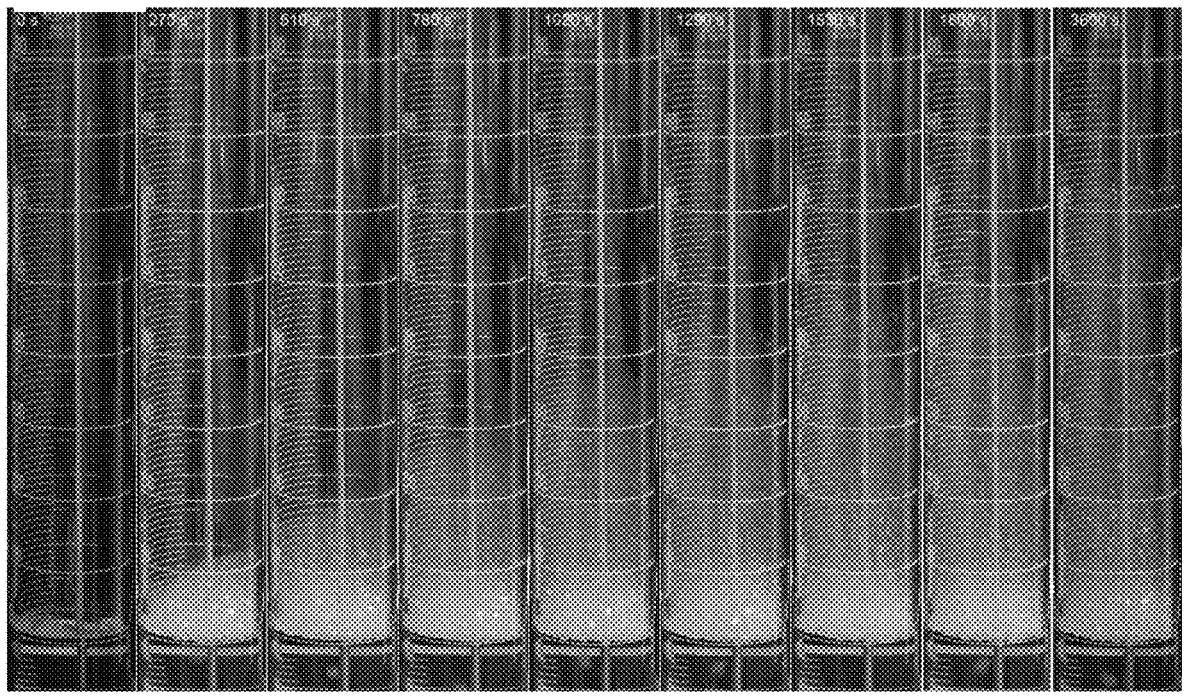
FIG. 40 show from left to right, at 0 seconds (s), 300 s, 600 s, 900 s, 1200 s, 1500 s, 1800 s, 2100 s and 3600 s (one hour) the foam growth of a 0.5 wt % solution of OFS-Cocinic-n=8-18.
Figure 41:
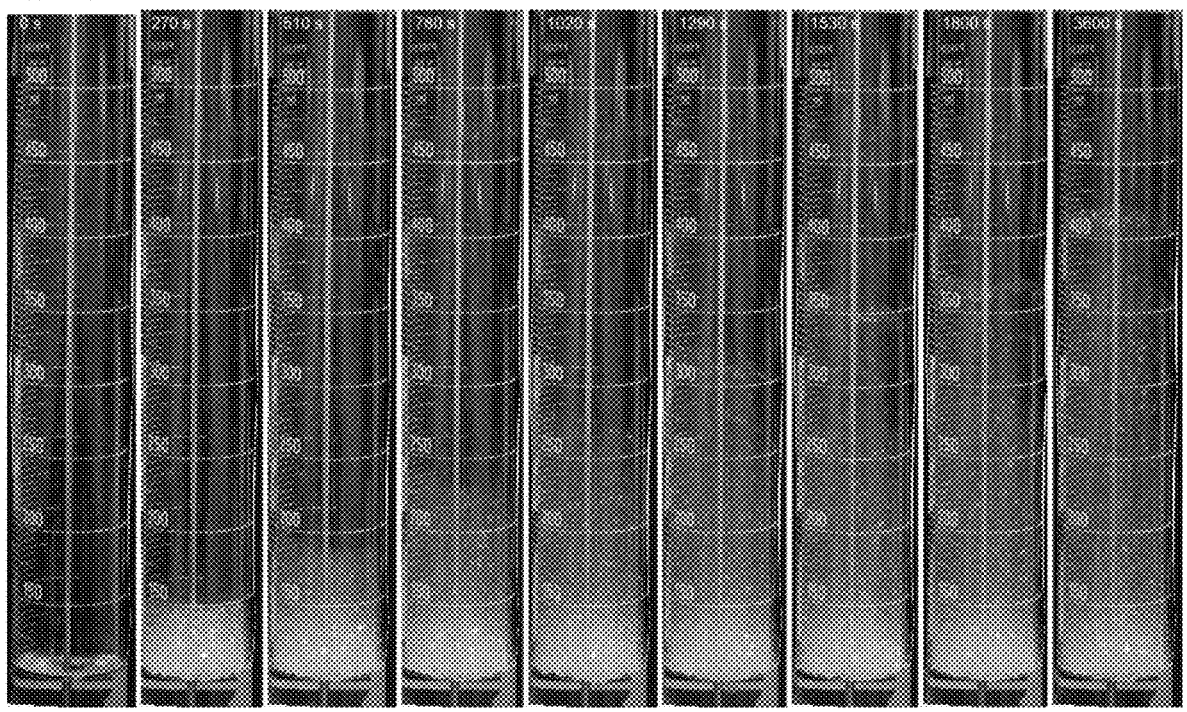
FIG. 41 show from left to right, at 0 seconds (s), 300 s, 600 s, 900 s, 1200 s, 1500 s, 1800 s, 2100 s and 3600 s (one hour) the foam growth of a 0.5 wt % solution of 40:60 mol % OFS-12-2/C2H5:OFS-12.
Figure 42:
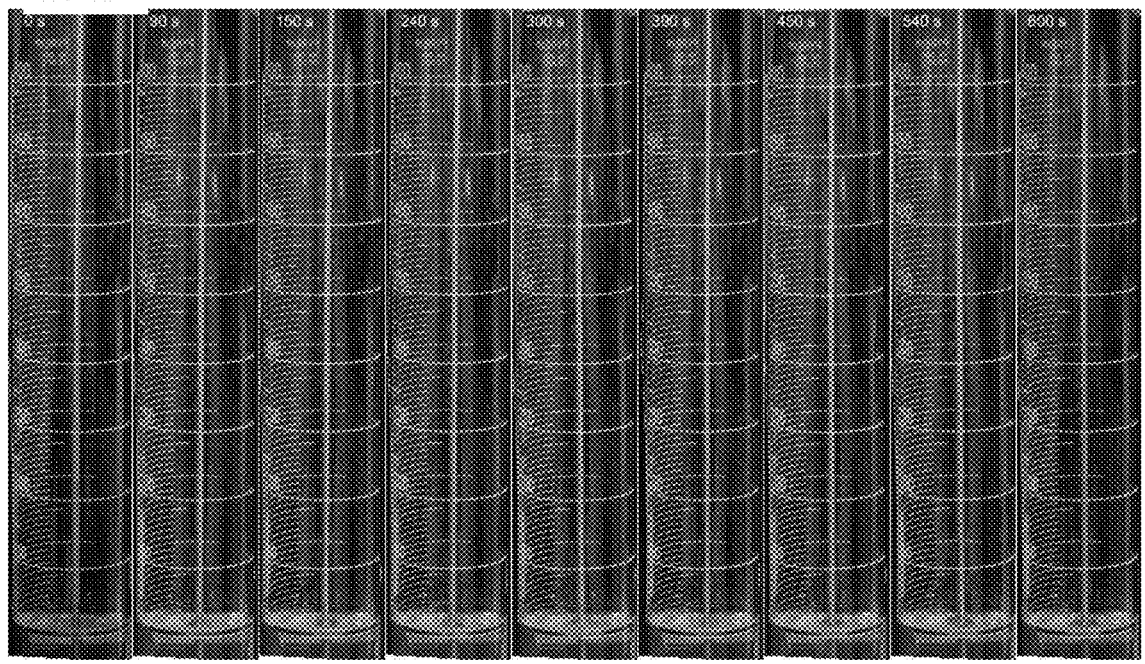
FIG. 42 show from left to right, at 0 seconds (s), 300 s, 600 s, 900 s, 1200 s, 1500 s, 1800 s, 2100 s and 3600 s (one hour) the foam growth of a 0.5 wt % solution of OFS-18-1/O.

The foaming properties of the surfactants were studied by bubbling air through a 0.5 wt % surfactant solution in 100 mL of deionized water. The apparatus utilized for the measurements is depicted in FIG. 32. The surfactant solution was poured into a 500 mL glass graduated cylinder. Air was bubbled through a ⅛ inch diameter and 16 inch length SS 316 tubing, which was immersed in the solution. A clearance of 1 inch was maintained between the end of the tubing and the bottom of the cylinder. The air flow rate was maintained at 30 sccm using a Brooks 5850E mass flow controller. The cylinder was mounted on a laboratory hot plate with magnetic stirring. A magnetic stirrer rotating at 380 rpm was also used to ensure uniform distribution of bubbles. All measurements were done above the Krafft point of the surfactant solutions. For those surfactants with a Krafft point above room temperature (OFS-12, OFS-14), the graduated cylinder was surrounded by a heated sand bath mounted on the hot plate. The temperature of the sand bath was set such that the solution temperature is just above its Krafft point. Air was bubbled through the solution until the foam height reached a steady value and the height was recorded every thirty seconds by means of a camera. The initial rate of foam growth was measured by calculating the slope of the linear region of the height vs. time plot before it attained equilibrium. The height of the foam column is indicative of the foaming capacity of the surfactant; the foam height after 60 min of air bubbling was, thus, used as a parameter to report foaming capacity. All surfactant foam heights reached an equilibrium value within 60 min with sodium lauryl ether sulfate (SLES) being an exception. For the purpose of comparison, Sodium Lauryl Sulfate (SLS) was chosen as a 'reference' surfactant and the initial foam growth rates and 60 min foam heights of all other surfactants were normalized with respect to SLS i.e. foam growth rate metric is reported as ratio of slope of linear region of surfactant i to that of SLS ($r_i/r_{SLS}$) and the foam height metric is reported as the ratio of foam height of surfactant i after 60 min (3600 s) to that of SLS ($h_{i\text{-}60}/h_{i\text{-}SLS}$) as shown in Table 23

Figure 43A:
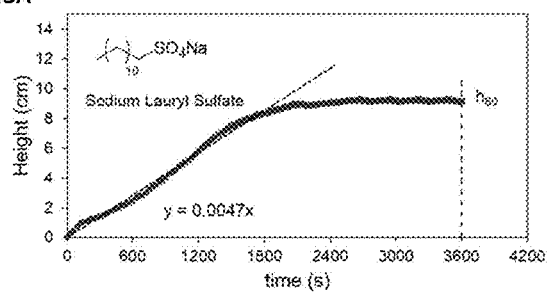
FIGS. 43A to 43D show foam height vs. time of 0.5 wt % commercial surfactant solutions: Sodium Lauryl Sulfate (SLS) (FIG. 43A), Methyl Ester Sulfonate (MES) (FIG. 43B), Linear Alkylbenzene Sulfonate (LAS) (FIG. 43C) and, Sodium Lauryl Ether Sulfate (SLES) (FIG. 43D).
Figure 43B:
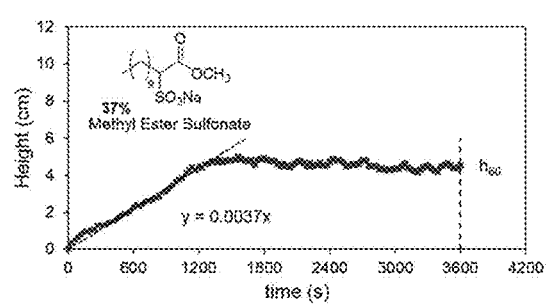
Figure 43C:
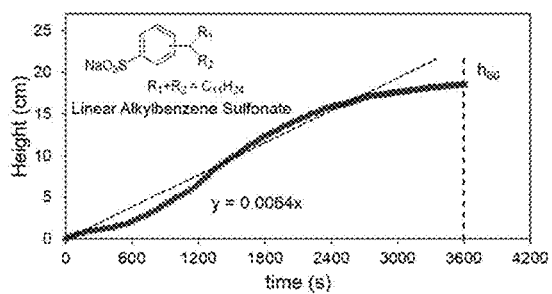
Figure 43D:
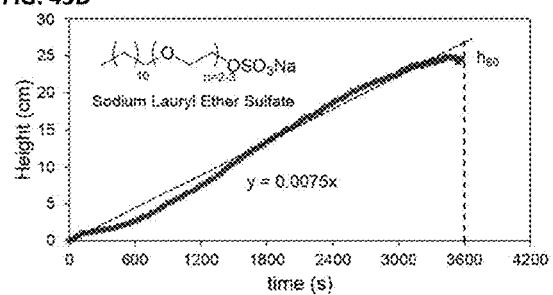
Figure 44A:
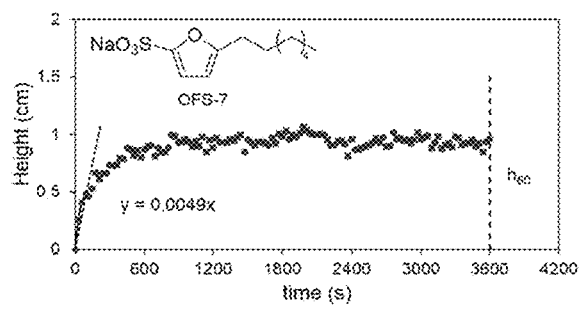
FIGS. 44A to 44E show foam height versus time of 0.5 wt % renewable OFS-n surfactant solutions: OFS-7 (FIG. 44A), OFS-12 (FIG. 44B), OFS-14 (FIG. 44C), OFS-Cocinic, n=8-18 (FIG. 44D) and 40:60 mol % OFS-12-2/C2H5:OFS-12 (FIG. 44E).
Figure 44B:
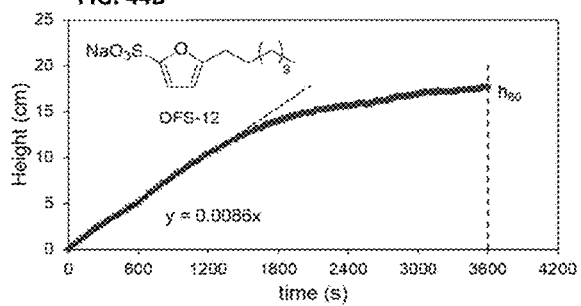
Figure 44C:
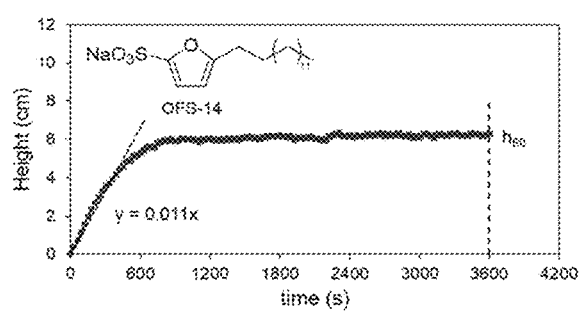
Figure 44D:
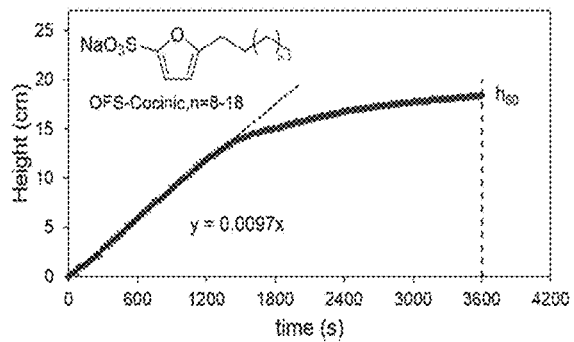
Figure 44E:
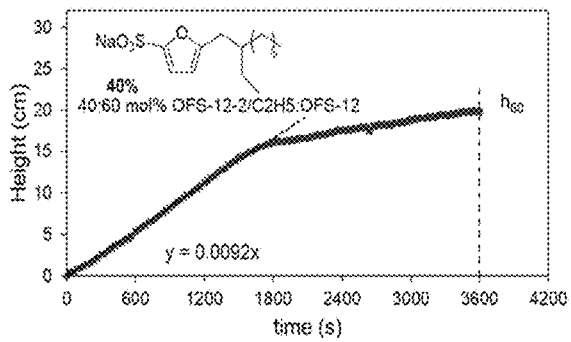

FIGS. 33 to 42 show images of the column at 0 seconds (s), 300 s, 600 s, 900 s, 1200 s, 1500 s, 1800 s, 2100 s and 3600 s (one hour) for 0.5 wt % solutions of sodium lauryl sulfate (SLS), methyl ester sulfonate (MES), linear alkylbenzene sulfonate (LAS), sodium lauryl ether sulfate (SLES), OFS-7, OFS-12, OFS-14, OFS-Cocinic-n=8-18, 40:60 mol % OFS-12/C2H5:OFS-12 and OFS-18-1/O respectively. FIGS. 43A to 43D show foam height vs. time of 0.5 wt % commercial surfactant solutions: Sodium Lauryl Sulfate (SLS) (FIG. 43A), Methyl Ester Sulfonate (MES) (FIG. 43B), Linear Alkylbenzene Sulfonate (LAS) (FIG. 43C) and, Sodium Lauryl Ether Sulfate (SLES) (FIG. 43D). The slope of the linear region (dashed line) represents the initial foam growth rate (r) while the height of the foam column ($h_{60}$), after 60 min (3600 s), is used as a foaming capacity indicator. FIGS. 44A to 44E show foam height versus time of 0.5 wt % renewable OFS-n surfactant solutions: OFS-7 (FIG. 44A), OFS-12 (FIG. 44B), OFS-14 (FIG. 44C), OFS-Cocinic, n=8-18 (FIG. 44D) and 40:60 mol % OFS-12-2/C2H5:OFS-12 (FIG. 44E). The slope of the initial linear region represents the initial foam growth rate (r) while the height of the foam column ($h_{60}$), after 60 min (3600 s), is used as a foaming capacity indicator.

Table 23 summarizes the results of the foaming tests.

TABLE 23

Summary of foaming parameters of all surfactants; normalized initial growth rates and foam heights after 60 min with respect to SLS.

| Surfactant | Foam Growth Rate[a] $r_i/r_{SLS}$ [-] | Foam Height$_{60}$[a,b] $h_{i\text{-}60}/h_{i\text{-}SLS}$ [-] |
|---|---|---|
| Commercial | | |
| SLS, Sodium Lauryl Sulfate | 1.00 | 1.00 |
| MES, Methyl Ester Sulfonate | 0.79 | 0.54 |
| LAS, Linear Alkylbenzene sulfonate | 1.36 | 2.20 |
| SLES, Sodium Lauryl Ether Sulfate | 1.60 | 2.94 |
| OFS, Oleo-Furan Sulfonates | | |
| OFS-12-1/O | 0 | 0 |
| OFS-14-1/O | 0 | 0 |
| OFS-18-1/O | 0 | 0 |
| OFS-Cocinic-1/O | 0 | 0 |
| OFS-7 | 1.04 | 0.12 |
| OFS-12 | 1.83 | 2.11 |
| OFS-14 | 2.34 | 0.75 |
| OFS-18 | — | — |
| OFS-Cocinic | 2.06 | 2.19 |
| 40:60 mol % OFS-12-2/C2H5:OFS-12 | 1.96 | 2.37 |
| 85:15 mol % OFS-12-1/P:OFS-12 | — | — |

[a]Measured at 0.5 wt % in water. [b]After 60 min (3600 s).

Draves Wetting Index

Figure 45A:
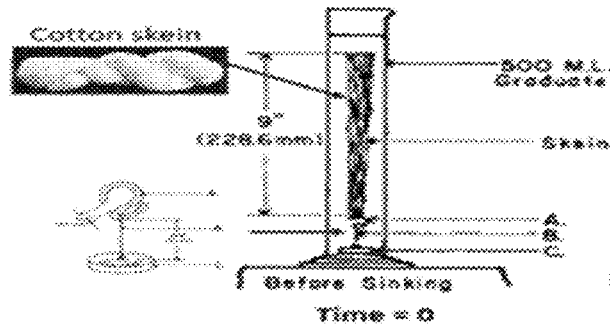
FIGS. 45A and 45B depict the apparatus utilized to measure the Draves Wetting Index.
Figure 45B:
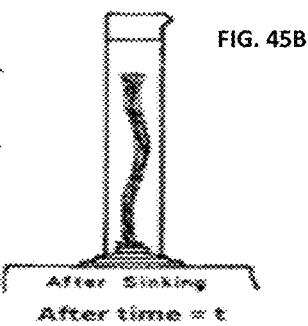
Figure 46A:
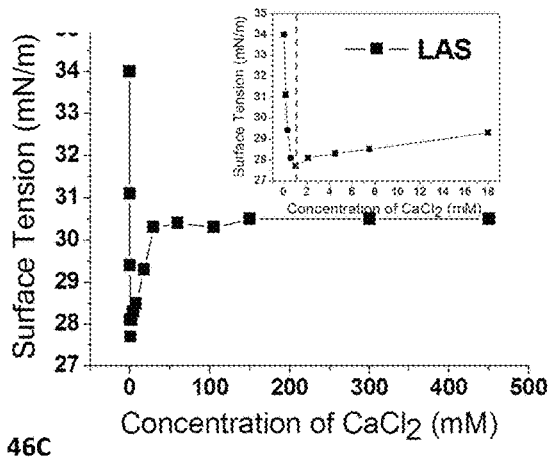
FIGS. 46A to 46D show surface tension versus CaCl$_2$ concentration of the standard commercial surfactants, LAS (FIG. 46A), SLS (FIG. 46B), MES (FIG. 46C), and SLES (FIG. 46D) (Concentration of the surfactant: Twice CMC, Hardness tolerance/micelle stability concentration: Calcium concentration at the increasing point of the surface tension indicated by the red dashed line).
Figure 46B:
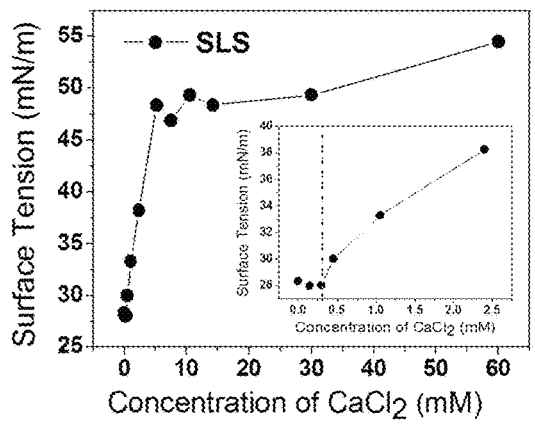
Figure 46C:
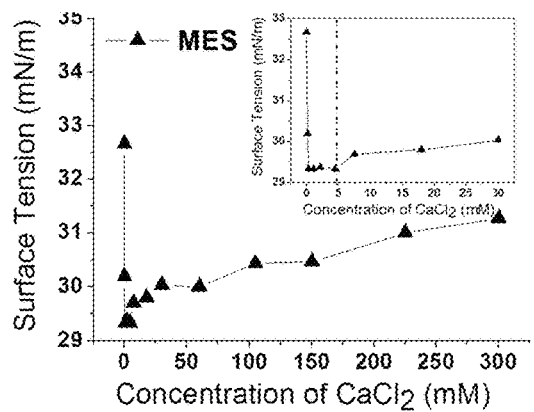
Figure 46D:
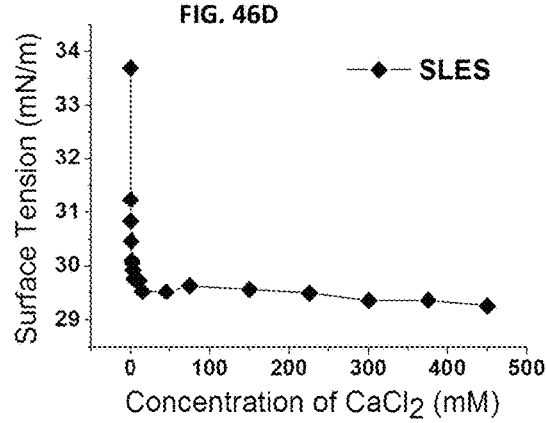

The wettability or the wetting properties of the surfactant were measured according to the ASTM D2281 standard (ASTM D2281-10, "Standard test method for evaluation of wetting agents by the skein test," ASTM International, West Conshohocken, Pa., 2010, DOI: 10.1520/D2281-10, www.astm.org). The apparatus utilized for testing is depicted in FIGS. 45A and 45B. 500 mL of 0.25 wt % surfactant solution was poured slowly into a 500 mL graduated cylinder to ensure that no foam was created while pouring. Any foam that was created was removed using a bulb-pipet. The temperature of the surfactant solution was maintained around its Krafft point by employing a heated sand bath throughout the course of the experiment.

A cotton skein (Test Fabrics, Item# 1203007), weighing approximately 5 g, was folded and fastened to an S-shaped 3 g copper hook tied to a 40 g lead anchor (lead slug) using a fine linen thread ¾ inch long (Test Fabrics, Item# WEIGHT & HOOK), see FIG. 45A. The ends of the skein were cut at the opposite end and the skein was made compact by drawing the cut skein through fingers before testing the surfactant. The skein is just immersed into the solution at t=0 seconds. The skein sinks after wetting time $T_D$. It was then dropped into the graduated cylinder containing the solution and the time taken for the thread to relax and the skein to sink to bottom was recorded as the wetting time ($T_D$) for 0.25 wt % solution, see FIG. 45B.

Table 24 shows the results of the Draves Wetting Test.

TABLE 24

Summary of Draves wetting time for all surfactants.

| Surfactant | Draves Wetting[a] [s] |
|---|---|
| Commercial | |
| SLS, Sodium Lauryl Sulfate | 6.3 ± 2.7 |
| MES, Methyl Ester Sulfonate | 15.1 ± 3.8 |
| LAS, Linear Alkylbenzene Sulfonate | 4.9 ± 3.2 |
| SLES, Sodium Lauryl Ether Sulfate | 15.4 ± 4.0 |
| OFS, Oleo-Furan Sulfonates | |
| OFS-12-1/O | >3600 |
| OFS-14-1/O | >3600 |
| OFS-18-1/O | >3600 |
| OFS-Cocinic-1/O | >3600 |
| OFS-7 | >3600 |
| OFS-12 | 48.9 ± 13.3 |
| OFS-14 | 39.4 ± 7.0 |
| OFS-18 | — |
| OFS-Cocinic | 58.0 ± 9.4 |
| 40:60 mol % OFS-12-2/C2H5:OFS-12 | 18.5 ± 1.9 |
| 85:15 mol % OFS-12-1/O:OFS-12 | — |

[a]Measured at 0.25 wt % surfactant in water

Hardness Tolerance

Precipitation of the anionic surfactant from hard water is an undesired process in detergency. The tendency of the anionic surfactants to precipitate is quantified by analyzing hardness tolerance. Hardness tolerance is the minimum concentration of counterion, such as, $Ca^{2+}$ and $Mg^{2+}$, precipitating with surfactant, resulting in deactivation of the surfactant performance (C. H. Rodriguez, L. H. Lowery, J. F. Scamehorn, J. H. Harwell, Kinetics of precipitation of surfactants. I. Anionic surfactants with calcium and with cationic surfactants. *Journal of Surfactants and Detergents* 4, 1-14 (2001); C. H. Rodriguez, C. Chintanasathien, J. F. Scamehorn, C. Saiwan, S. Chavadej, Precipitation in solutions containing mixtures of synthetic anionic surfactant and soap. I. Effect of sodium octanoate on hardness tolerance of sodium dodecyl sulfate. *Journal of Surfactants and Detergents* 1, 321-328 (1998); and J. F. Scamehorn, "Precipitation of mixtures of anionic surfactants" in mixed Surfactant systems ACS Symposium Series (American Chemical Society: Washington D.C., 1992), pp. 392-401). Calcium chloride was used as a divalent counterion, and surface tension of the surfactant solution was measured with increasing concentration of $CaCl_2$ from 1 mM to 450 mM. The value of calcium concentration above which the surface tension of the surfactant solution increased was recorded as the tolerance value of the surfactant towards calcium as indicated by the dashed red line in FIGS. 46A to 49B. For the OFS-n surfactants, a momentary turbidity was observed in the surfactant solution upon addition of $CaCl_2$ due to localized concentration gradients which disappeared upon stirring unlike the OFS-n-1/O, LAS and SLS surfactants where the turbidity/precipitation continued to persist even upon vigorous stirring.

Figure 47A:
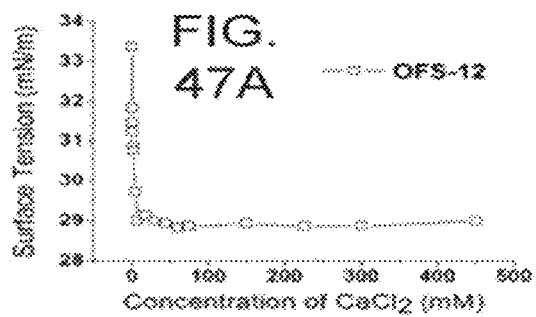
FIGS. 47A to 47D show surface tension vs. CaCl$_2$ concentration of the linear OFS-n surfactants: OFS-12 (FIG. 47A), OFS-14 (FIG. 47B), OFS-18 (FIG. 47C) and OFS-Cocinic (FIG. 47D).
Figure 47B:
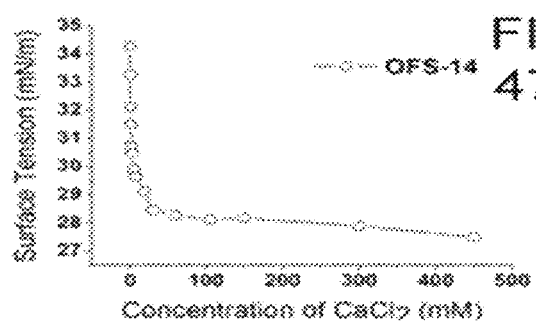
Figure 47C:
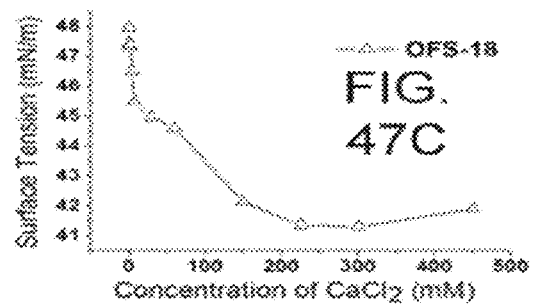
Figure 47D:
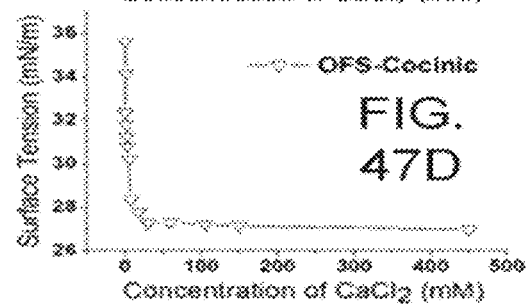
Figure 48A:
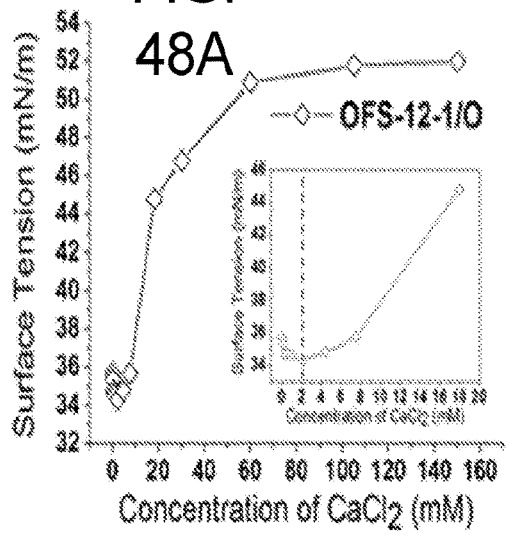
FIGS. 48A to 48D show surface tension versus CaCl$_2$ concentration of the OFS-n-1/O surfactants: OFS-12-1/O (FIG. 48A), OFS-14-1/O (FIG. 48B), OFS-18-1/O (FIG. 48C) and OFS-Cocinic-1/O (FIG. 48D).
Figure 48B:
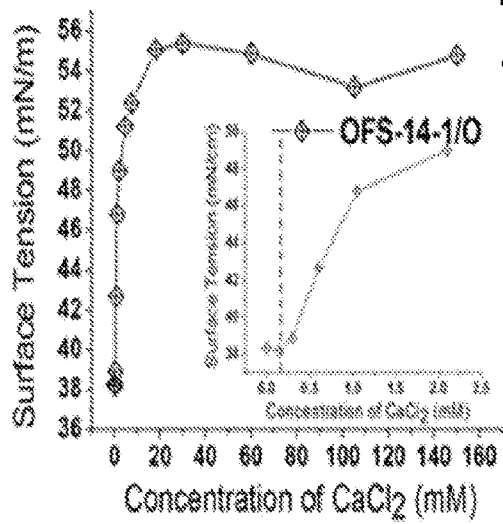
Figure 48C:
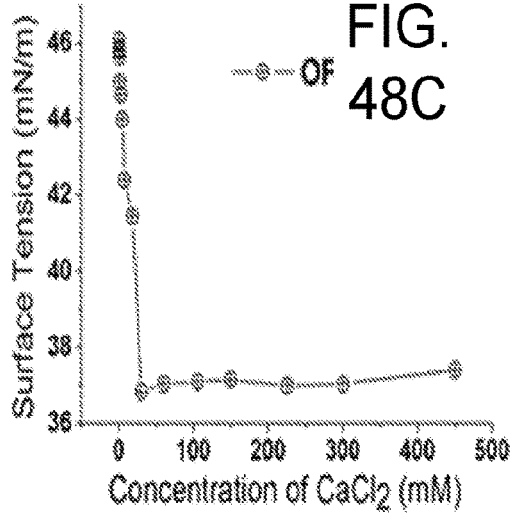
Figure 48D:
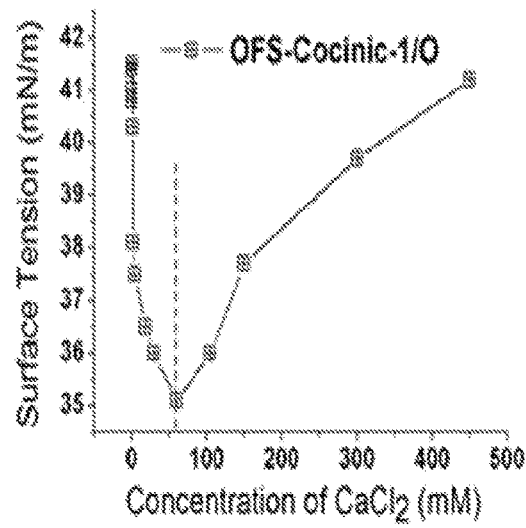
Figure 49A:
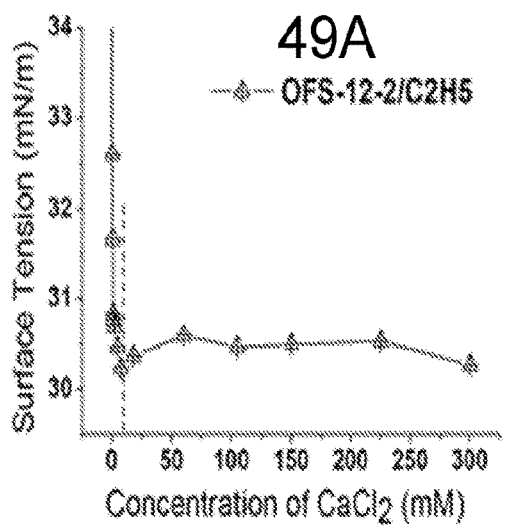
FIGS. 49A and 49B show surface tension versus CaCl$_2$ concentration of OFS-12-2/C2H5 (FIG. 49A) and OFS-7 (FIG. 49B).
Figure 49B:
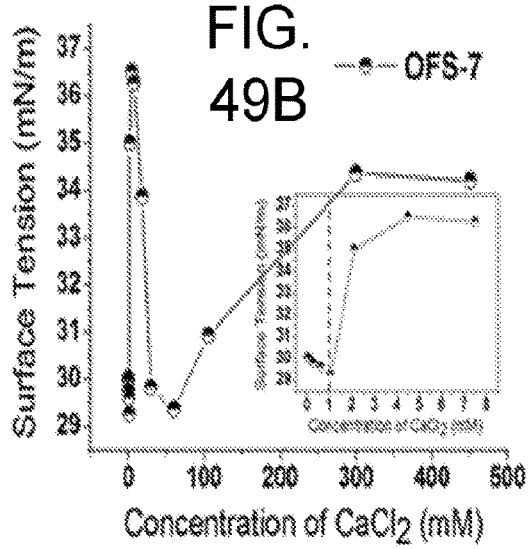

FIGS. 46A to 46D shows surface tension versus $CaCl_2$ concentration of the standard commercial surfactants, LAS (FIG. 46), SLS (FIG. 46B), MES (FIG. 46C), and SLES (FIG. 46D) (Concentration of the surfactant: Twice CMC, Hardness tolerance/micelle stability concentration: Calcium concentration at the increasing point of the surface tension indicated by the red dashed line). FIGS. 47A to 47D show surface tension vs. $CaCl_2$ concentration of the linear OFS-n surfactants: OFS-12 (FIG. 47A), OFS-14 (FIG. 47B), OFS-18 (FIG. 47C) and OFS-Cocinic (FIG. 47D). (Concentration of the surfactant: Twice CMC, Hardness tolerance/micelle stability concentration: Calcium concentration at the increasing point of the surface tension). FIGS. 48A to 48D show surface tension versus $CaCl_2$ concentration of the OFS-n-1/O surfactants: OFS-12-1/O (FIG. 48A), OFS-14-1/O (FIG. 48B), OFS-18-1/O (FIG. 48C) and OFS-Cocinic-1/O (FIG. 48D). (Concentration of the surfactant: Twice CMC, Hardness tolerance/micelle stability concentration: Calcium concentration at the increasing point of the surface tension indicated by the red dashed line). FIGS. 49A and 49B show surface tension versus $CaCl_2$ concentration of OFS-12-2/C2H5 (FIG. 49A) and OFS-7 (FIG. 49B) (Concentration of the surfactant: Twice CMC, Hardness tolerance/micelle stability concentration: Calcium concentration at the increasing point of the surface tension indicated by the red dashed line). At the tolerance value, the $Ca^{2+}$ ions disrupt the micelle structure and this value of calcium concentration is referred to as micelle stability.

Figure 50A:
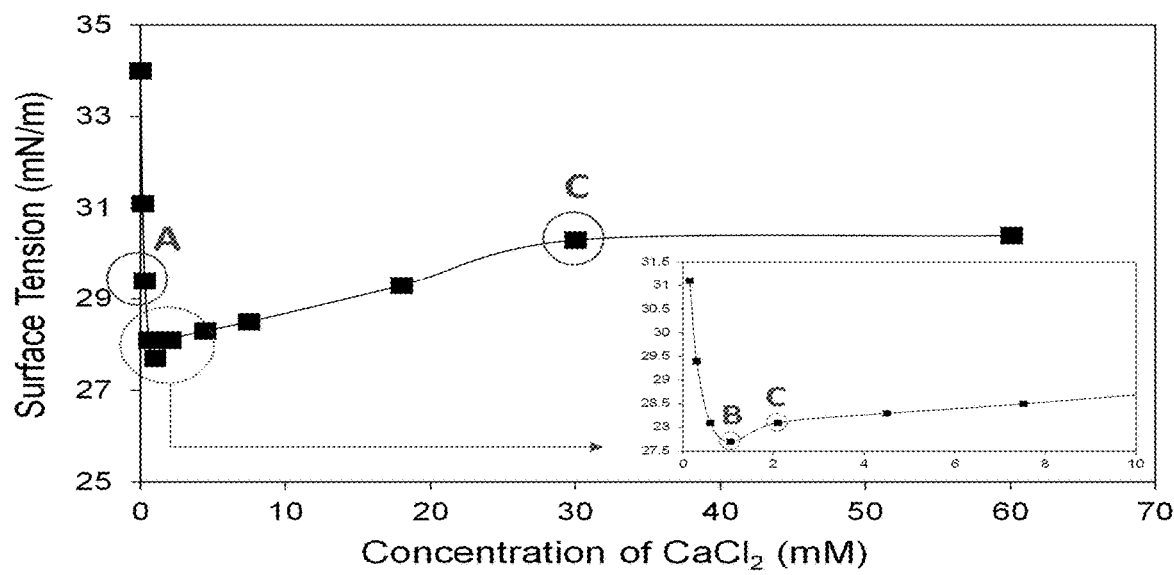
FIGS. 50A to 50E show a graph of the concentration of CaCl$_2$ (mM) versus surface tension (mN/m) for the four solutions depicted in FIGS. 50B to 50E: a clear solution at low calcium concentration (33 ppm, corresponding to soft water conditions) (FIG. 50B), a LAS solution at 100 ppm of Ca$^{2+}$ corresponding to the tolerance value (micelle stability) (FIG. 50C) a cloudy solution at the turbid concentration (230 ppm, corresponding to hard water conditions) (FIG. 50D) and a cloudy solution with the formation of calcium precipitates (3300 ppm, corresponding to extreme hard water conditions) (FIG. 50E).
Figure 50B:
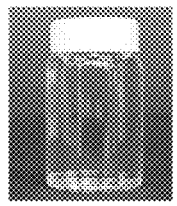
Figure 50C:
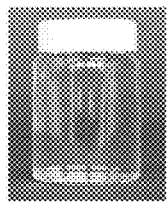
Figure 50D:
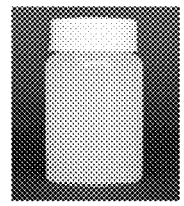
Figure 50E:
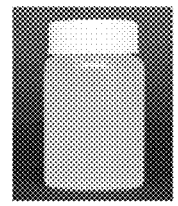
Figure 51:
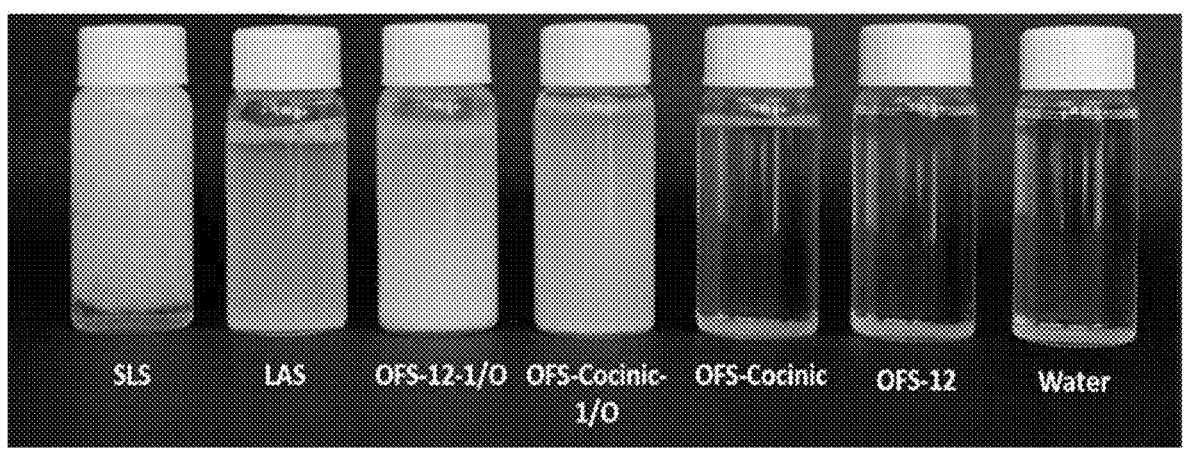
FIG. 51 shows surfactant solutions after addition of $CaCl_2$ (Surfactant concentration: Twice CMC, Concentration of $CaCl_2$: 50,000 ppm). Image was taken two weeks after the solution was made.

All experiments were carried out at a concentration equal to twice CMC of each surfactant, and the point of transition from a clear solution to a turbid one was also monitored. FIGS. 50A to 50E illustrate this effect for a linear alkylbenzene sulfonate (LAS) solution. Below the turbid point, the surfactant solution was clear as shown by FIGS. 50B and 50C which changed to a cloudy solution at calcium concentrations equal to and greater than the turbid point (FIG. 50D and FIG. 50E). The point of micelle stability was marked by an increase in the surface tension of the surfactant solution with an increase in calcium concentration. FIG. 50C corresponds to the micelle stability concentration and FIG. 50D corresponds to the turbid concentration. Micelle stability is defined as the calcium concentration at the increasing point of surface tension, and turbid concentration marks the onset of turbidity in the surfactant solution The solution transitions from clear to turbid as shown in FIGS. 50B to 50E FIG. 51 shows the surfactant solutions with $CaCl_2$ added (Surfactant concentration: Twice CMC, Concentration of $CaCl_2$: 50,000 ppm) two weeks after the solutions were made.

Table 25 shows a summary of the hard water stability testing.

TABLE 25

Summary of hard water stability tests for all surfactants.

| Surfactant | Micelle stability conc. [ppm of $CaCl_2$][a] | Turbid conc. [ppm of $CaCl_2$][a] |
|---|---|---|
| Commercial | | |
| SLS, Sodium Lauryl Sulfate | 33 | 33 |
| MES, Methyl Ester Sulfonate | 500 | >50,000 |
| LAS, Linear Alkylbenzene Sulfonate | 100 | 230 |
| SLES, Sodium Lauryl Ether Sulfate | >50,000 | >50,000 |
| OFS, Oleo-Furan Sulfonates | | |
| OFS-12-1/O | 230 | 230 |
| OFS-14-1/O | 33 | 66 |
| OFS-18-1/O | >50,000 | 2,000 |
| OFS-Cocinic-1/O | 6,600 | 500 |
| OFS-7 | 110 | 230 |
| OFS-12 | >50,000 | 10,000 |
| OFS-14 | >50,000 | 2,000 |
| OFS-18 | 33,000 | 2,000 |

TABLE 25-continued

Summary of hard water stability tests for all surfactants.

| Surfactant | Micelle stability conc. [ppm of $CaCl_2$][a] | Turbid conc. [ppm of $CaCl_2$][a] |
|---|---|---|
| OFS-Cocinic | >50,000 | 10,000 |
| 40:60 mol % OFS-12-2/C2H5:OFS-12 | 2,000 | 2,000 |
| 85:15 mol % OFS-12-1/O:OFS-12 | — | — |

[a]Measured at twice CMC of the surfactants

Thus, embodiments of aromatic surfactants are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

The invention claimed is:

1. A compound of formula 3

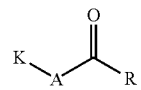

wherein K comprises a sulfate group or a sulfonate group, A is a furan, pyrrole, or imidazole, aromatic moiety optionally substituted and R is a linear or branched main alkyl chain having from 6 to 26 carbon atoms and optionally substituted with a $C_1$ to $C_6$ alkyl chain branched from the main alkyl chain.

2. The compound according to claim 1 selected from:

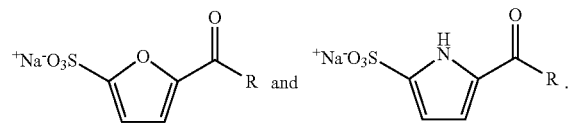

3. The compound according to claim 1 selected from:

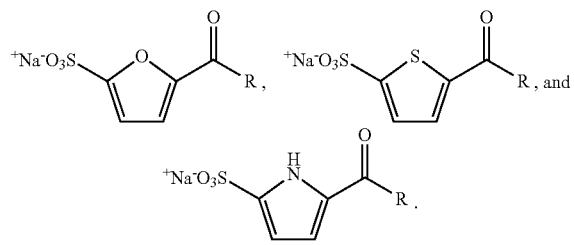

4. The compound according to claim 1, wherein the branched alkyl chain is methyl ($CH_3$), ethyl ($CH_2CH_3$), or n-propyl ($CH_2CH_2CH_3$).

5. The compound according to claim 1, wherein A is a functionalized or non-functionalized furan moiety.

6. The compound according to claim 1, wherein A is pyrrole, or imidazole.

7. The compound according to claim 1, wherein K is selected from
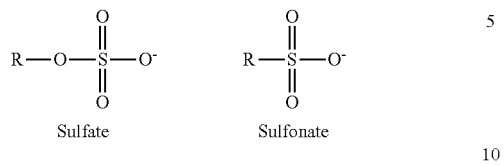
Sulfate    Sulfonate
wherein in the above structures,
R can denote either the point of attachment to the ion to A in formula I or a hydrocarbon chain with or without heteroatoms attached to A.
* * * * *